(12) United States Patent
Dickinson et al.

(10) Patent No.: US 10,413,583 B2
(45) Date of Patent: Sep. 17, 2019

(54) SYNTHETIC SUBSTRATES FOR ENZYMES THAT CATALYZE REACTIONS OF MODIFIED CYSTEINES AND RELATED METHODS

(71) Applicant: The University of Chicago, Chicago, IL (US)

(72) Inventors: Bryan C. Dickinson, Chicago, IL (US); Rahul S. Kathayat, Chicago, IL (US); Michael W. Beck, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 15/827,497

(22) Filed: Nov. 30, 2017

(65) Prior Publication Data

US 2018/0147250 A1 May 31, 2018

Related U.S. Application Data

(60) Provisional application No. 62/556,873, filed on Sep. 11, 2017, provisional application No. 62/428,034, filed on Nov. 30, 2016.

(51) Int. Cl.

| | |
|---|---|
| *C07D 493/10* | (2006.01) |
| *A61K 38/05* | (2006.01) |
| *A61K 31/35* | (2006.01) |
| *A61K 31/365* | (2006.01) |
| *C07K 5/062* | (2006.01) |
| *A61K 31/4375* | (2006.01) |
| *C07K 5/068* | (2006.01) |
| *A61K 31/498* | (2006.01) |

(52) U.S. Cl.
CPC ............ *A61K 38/05* (2013.01); *A61K 31/35* (2013.01); *A61K 31/365* (2013.01); *A61K 31/4375* (2013.01); *A61K 31/498* (2013.01); *C07D 493/10* (2013.01); *C07K 5/0606* (2013.01); *C07K 5/06086* (2013.01)

(58) Field of Classification Search
CPC .................................................. C07D 493/10
See application file for complete search history.

(56) References Cited

U.S. PATENT DOCUMENTS

| | | | | |
|---|---|---|---|---|
| 4,559,328 A | * | 12/1985 | Smerbeck ............... | A61K 31/05 514/159 |
| 4,855,287 A | * | 8/1989 | Watanabe ............... | C07H 15/12 514/41 |
| 5,280,027 A | * | 1/1994 | Andrew ............... | C07D 239/90 514/266.2 |
| 5,628,984 A | | 5/1997 | Boucher, Jr. | |
| 2010/0189660 A1 | | 7/2010 | Hannoush | |
| 2017/0137443 A1 | | 5/2017 | Wang et al. | |

FOREIGN PATENT DOCUMENTS

JP 2004203872 A * 7/2004

OTHER PUBLICATIONS

Macht, D. Journal of Pharmacology and Experimental Therapeutics Apr. 1, 1918, 11 (3) 263-279 (Year: 1918).*
CAS Registry Entry for Registry No. 73167-51-8, which entered STN on Nov. 16, 1984 (Year: 1984).*
Kathayat et al. Nat Chem Biol. Feb. 2017; 13(2): 150-152 (Year: 2016).*
Qiu et al. Biochemistry 2018, 57, 221-225 (Year: 2017).*
Naithani et al. International Congress Series, 1978, 468, 36-40 (Year: 1978).*
Bridges et al. Biochem. J. 1965, 96, 872-878 (Year: 1965).*
Taniguchi et al. Photochemistry and Photobiology 2018, 94, 290-327 (Year: 2018).*
Nikolaev, A. Abstracts of OSU International Symposium on Molecular Spectroscopy 2000-2009, Rotationally Resolved Fluorescence Excitation Spectroscopy of Benzyl Alcohol, 2000 (Year: 2000).*
Babler and Spina (1983) Stereochemistry of the dealkoxycarbonylation of methl α-cyanocinnamate and of the decarboxylation of the corresponding cyanoacid: a facile stereoselective route to Z-cinnamonitrile. Tetrahedron Letters 24(36):3835-3838.
Dekker et al. (2010) Small-molecule inhibition of APT1 affects Ras localization and signaling. Net Chem Biol 6(6):449-456.
Eisenberg et al. (2013) The role of palmitoylation in regulating Ras localization and function. Biochem Soc Trans 41(1):79-83.
Gormer et al. (2012) Chemical-biological exploration of the limits of the Ras de- and repalmitoylating machinery. Chembiochem 13:1017-1023.
Hernandez et al. (Jan. 19, 2017) APT2 Inhibition Restores Scribble Localization and S-Palmitoylation in Snail-Transformed Cells. Cell Chem Biol 24(1):89-97.
Kim et al. (2014) Ratiometric fluorescence probes based on a Michael acceptor type of coumarin and their application for the multichannel imaging of in vivo glutathione. RSC Advances 4:18731-18736.
Kwon et al. (2011) Coumarin—malonitrile conjugate as a fluorescence turn-on probe for biothiols and its cellular expression. Chem Comrnun (Comb) 47:1773-1775.

(Continued)

*Primary Examiner* — Matthew P Coughlin
(74) *Attorney, Agent, or Firm* — Jenkins, Wilson, Taylor & Hunt, P.A.

(57) ABSTRACT

Synthetic probes for detecting the activity of enzymes that catalyze reactions of post-translationally modified cysteine residues are described. The probes include "turn-on" probes that include a carbamate linkage that is cleaved via an intramolecular reaction with a free thiol produced by an enzyme catalyzed activity. The probes also include ratiometric, Michael addition-based probes that respond to enzymatic activity by a change in structure that results in a change in fluorescence properties. Methods of using the probes to detect enzymatic activity and disease are described. For example, the probes can be used to detect enzymatic activity in a variety of samples, including live cells and heterogeneous tissues. In addition, prodrugs that can be activated by enzymes that catalyze reactions of post-translationally modified cysteine residues and methods of using the prodrugs to treat disease are described.

13 Claims, 30 Drawing Sheets
Specification includes a Sequence Listing.

(56) References Cited

OTHER PUBLICATIONS

Lanyon-Hogg et al. (Jul. 2017) Dynamic Protein Acylation: New Substrates, Mechanisms, and Drug Targets. 42(7):566-581.
Linder and Deschenes (2007) Palmitoylation: policing protein stability and traffic. Nat Rev Mol Cell Biol. 8(1):74-84.
Liu et al. (2015) A Reversible Fluorescent Probe for Real-Time Quantitative Monitoring of Cellular Glutathione. Angew Chem Int Ed Engl 56(21):5812-5816.
Nissar et al. (2015) Palmitic acid induced lipotoxicity is associated with altered lipid metabolism, enhanced CYP450 2E1 and intracellular calcium mediated ER stress in human hepatomoa cells. Toxicol Res 4:1344-1358.
Park et al. (2009) The relationship between solid-state fluorescence intensity and molecular packing of coumarin dyes. Dyes and Pigments 82(3):258-26.
Qu et al. (2016) A phenazine-based near-infrared (NIR) chemodosimeter for cysteine obtained via a carbonyl-assisted cycloaddition process. RSC Advances 6:22389-22394.
Rohrig and Schulze (2016) The multifaceted roles of fatty acid synthesis in cancer. Nat Rev Cancer 16:732-749.
Rusch et al. (2011) Identification of acyl protein thioesterases 1 and 2 as the cellular targets of the Ras-signaling modulators palmostatin B and M. Angew Chem Int Ed Engl 50:9838-9842.
Sato et al. (2011) Long-term expansion of epithelial organoids from human colon, adenoma, adenocarcinoma, and Barrett's epithelium. Gastroenterology 141:1762-1772.
Sauers et al. (1987) Shaping the absorption and fluorescence bands of a class of efficient, photoactive chromophores: synthesis and properties of some new 3H-xanthen-3. Dyes and Pigments 8:35-53.
Smith et al. (1993) The design and properties of a series of calcium indicators which shift from rhodamine-like to fluorescein-like fluorescence on binding calcium. Journal of the Chemical Society, Perkin Transactions 2, 6:1195-1204.
Adibekian et al. (2012) Confirming target engagement for reverisble inhibitors in vivo by kinetically tuned activity-based probes. J Am Chem Soc. 134(25):10345-8.
Aicart-Ramos et al. (2011) Protein palmitoylation and subcellular trafficking. Biochim Biophys Acta 1808(12)298-2994.
Baldwin et al. (2012) A role for aberrant protein palmitoylation in FFA-induced ER stress and β-cell death. Am J Physiol Endocrinol Metab 302(11):E1390-E1398.
Chan et al. (Apr. 2016) Autopalmitoylation of TEAD proteins regulates transcriptional output of the Hippo pathway. Net Chem Biol 12(4)282-289.
Chent et al. (2010) MolProbity: all-atom structure validation for macromolecular crystallographt.. Acta Crystallogr D Biol Crystallogr 66(Pt 1):12-21.
Chen et al. (2013) Tunable Thioesters as "Reduction" Responsive Functionality for Traceless Reverisble Protein PEGylation. Am. Chem. Soc. 135:10938-10941.
Corey and Fraenkel (1953) The Existence of a 1,2-Addition, 1,2-Elimination Mechanism for Decarboxylation. J Am Chem Soc 75:1168-1172.
Creaser and Peterson (2002) Sensitive and Rapid Analysis of Protein Palmitoylation with a Synthetic Cell-Permeable Mimic of Src Oncoproteins. J. Am. Chem. Soc. 124(11)2444-2445.
Cunha (2008) Initiation and execution of lipotoxic ER stress in pancreatic β-cells. J Cell Sci 121(14):2308-2318.
Davda and Martin (2014) Acyl protein thioesterase inhibitors as probes of dynamic S-palmitoylation. Medchemcomm 5(3):268-276.
Dekker and Hedberg (2011) Small molecule inhibition of protein depalmitoylation as a new approach tolwards downregulation of oncogenic Ras signalling. Bioorg Med Chem 19:1376-1380.
Dickinson and Chang (2008) A Targetable Fluorescent Probe for Imaging Hydrogen Peroxide in the Mitochondria of Living Cells. J Am Chem Soc 130:9638-9639.
El-Husseini et al. (2002) Synaptic strength regulated by palmitate cycling on PSD-95. Cell 108(6):849-863.

Fröhlich et al. (2014) S-palmitoylation represents a novel mechanism regulating the mitochondrial targeting of BAX and initiation of apoptosis. Cell Death Dis 5:e1057:1-9.
Fukata et al. (2004) Identification of PSD-95 palmitoylating enzymes. Neuron 44(6):987-996.
Hanwell et al. (2012) Avogadro: an advanced semantic chemical editor, visualization, and analysis platform. J Cheminform 4(1):1-17.
Hernandez et al (2013) Profiling and inhibiting reversible palmitoylation. Currnent Opinion in Chemical Biology 17(1):20-26.
Howell et al. (2006) Cell Biology of Membrane Trafficking in Human Disease. International Review of Cytology 252:1-69.
Kathayat et al. (Feb. 2017) A fluorescent probe for cysteine depalmitoylation reveals dynamic APT signaling. Nat Chem Biol 13(2):150-152. (Published online Dec. 19, 2016).
Kong et al. (2013) Dynamic palmitoylation links cytosol-membrane shuttling of acyl-protein thioesterase-1 and acyl-protein thioesterase-2 with that of proto-oncogene H-ras product and growth-associated protein-43.
Krenske et al. (Dec. 2, 2016) Kinetics and Thermodynamics of Reversible Thiol Additions to Mono- and Diactiated Michael Acceptors: Implications for the Design of Drugs That Bind Covalently to Cysteines. J Org Chem 81(23):11726-11733.
Krishnan et al. (2014) Design of Reversible, Cysteine-Targeted Michael Acceptors Guided by Kinetic and Computational Analysis. J Am Chem Soc 136(36):12624-12630.
Lee et al. (2010) A Two-Photon Fluorescent Probe for Thiols in Live Cells and Tissues. J Am Chem Soc 132(4):1216-1217.
Lin et al. (2012) Protein Lysine Acylation and Cysteine Succination by Intermediates of Energy Metabolism. American Chemical Society 7:947-960.
Lin and Conibear (2015) ABHD17 proteins are novel protein depalmitoylases that regulate N-Ras palmitate turnover and subcellular localization. eLife 4(e11306):1-14.
Long and Cravatt (2011) The Metabolic Serine Hydrolases and Their Functions in Mammalian Physiology and Disease. Chem. Rev. 111(10):6022-3063.
Martin et al. (2011) Global profiling of dynamic protein palmitoylation. Nat Methods 9(1):84-89.
Moffat et al. (2006) A Lentiviral RNAi Library for Human and Mouse Genes Applied to an Arrayed Viral High-Content Screen. Cell 124(6):1283-1298.
Morris et al. (2009) AutoDock4 and AutoDockTools4: Automated docking with selective receptor flexibility. J Comput Chem 30(16):2785-2791.
Noland et al. (Jan. 5, 2016) Palmitoylation of TEAD Transcription Factors Is Required for Their Stability and Function in Hippo Pathway Signaling. Structure 24(1):179-186.
O'Boyle et al. (2011) Open Babel: An open chemical toolbox. J Cheminform 3:33.
Rocks et al. (2010) The palmitoylation machinery is a spatially organizing system for peripheral membrane proteins. Cell 141(3):458-471.
Paulsen and Carroll (2013) Cysteine-Mediated Redox Signaling: Chemistry, Biology, and Tools for Discovery. Chemical Reviews 113:4633-4679.
Peng et al. (Feb. 2016) Proteomic analysis of fatty-acylated proteins. Curr Opin Chem Biol 30:77-86.
Peng et al. (2012) Thiol Reactive Probes and Chemosensors. Sensors 12:15907-15946.
Ponimaskin et al. (2008) Fibroblast growth factor-regulated palmitoylation of the neural cell adhesion molecule determines neuronal morphogenesis. J. Neurosci. 3(28):8897-8907.
Qui et al. (Oct. 12, 2017) A Fluorescent Probe with Improved Water Solubility Permits the Analysis of Protein S-Depalmitoylation Activity in Live CellsBiochemistry. Biochemistry 1-5.
Rooker and Buccella (2015) Real-time detection of histone deacetylase activity with a small molecule fluorescent and spectrophotometric probe. Chem Sci 6:6456-6461.
Sanders et al. (2015) Curation of the Mammalian Palmitoylome Indicates a Pivotal Role for Palmitoylation in Diseases and Disorders of the Nervous System and Cancers. PLOS Computational Biology 1198):e1004405:1-20.

(56) References Cited

OTHER PUBLICATIONS

Serafimova et al. (20120 Reversible targeting of noncatalytic cysteines with chemically tuned electrophiles. Nat Chem Biol 8(5)471-476.
Topinka and Bredt (1998) N-terminal palmitoylation of PSD-95 regulates association with cell membranes and interaction with K+ channel Kv1.4. Neuron 20(1):125-34.
Trott and Olson (2010) AutoDock Vina: improving the speed and accuracy of docking with a new scoring function, efficient optimization and multithreading. J Comput Chem 31(2):455-461.
Verkruyse and Hofmann (1996) Lysosomal Targeting of Palmitoyl-protein Thioesterase, The Journal of Biological Chemistry 271(26):15831-15836.
Vippila et al. (2015) Synthesis and Antiproliferative Activity Evaluation of the Disulfide-Containing Cyclic Peptide Thiochondrilline C and Derivatives. J Nat Prod 78(10):2398-2404.
Won et al. (2016) Molecular Mechanism for Isoform-Selective Inhibition of Acyl Protein Thioesterases 1 and 2 (APT1 and APT2). ACS Chem. Biol. 11(12):3374-3382.
Zhang et al. (2010) Tandem fluorescence imaging of dynamic S-acylation and protein turnover. Proc Natl Acad Sci USA 107(19):8627-8632.
Zhang et al. (2012) Palmitic and linoleic acids induce ER stress and apoptosis in hepatoma cells. Lipids in Health and Disease 11:1-8.
Zheng et al. (2013) 2-Bromopalmitate Analogues as Activity-Based Probes to Explore Palmitoyl Acyltransferases. J. Am. Chem. Soc. 135(19):7082-7085.
Beck et al. (2017), "Michael addition-based probes for ratiometric fluorescence imaging of protein S-depalmitoylases in live cells and tissues," Chemical Science, vol. 8, pp. 7588-7592.
Li et al. (2012), "Photoactivatable fluorophores and techniques for biological imaging applications," Photochemical and Photobiological Sciences, vol. 11, No. 3, pp. 460-471.
Long and Cravatt (2011) The Metabolic Serine Hydrolases and Their Functions in Mammalian Physiology and Diseases. Chem. Rev. 111(10):6022-6063.
Lu and Hofmann (1995), "Depalmitoylation of CAXX Motif Proteins: Protein Structural Determinants of Palmitate Turnover Rate," J Biol Chem., vol. 270, No. 13, pp. 7251-7256.
Park et al. (2009) The relationship berween solid-state fluorescence intensity and molecular packing of coumarine dyes. Dyes and Pigments 83(3):258-267.
Qiu et al. (Oct. 12, 2017) A Fluorescent Probe with Improved Water Solubility Permits the Analysis of Protein S-Depalmitoylation Activity in Live Cells, Biochemistry, pp. 1-5.

\* cited by examiner

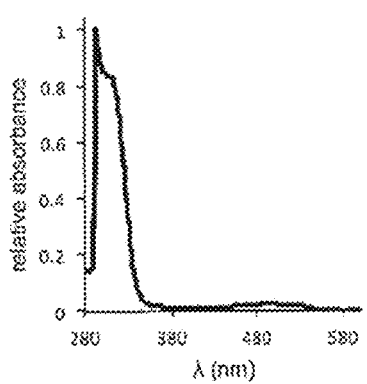 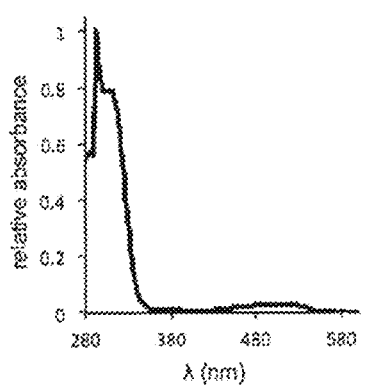
FIG. 3A  FIG. 3B
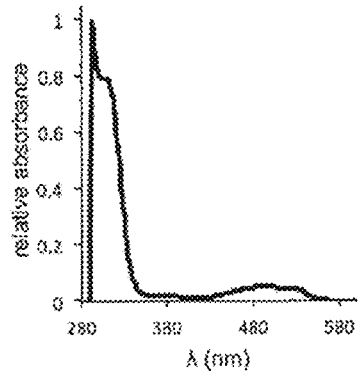 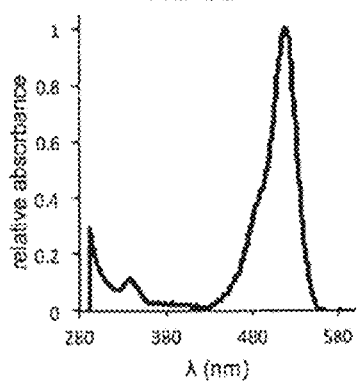
FIG. 3C  FIG. 3D

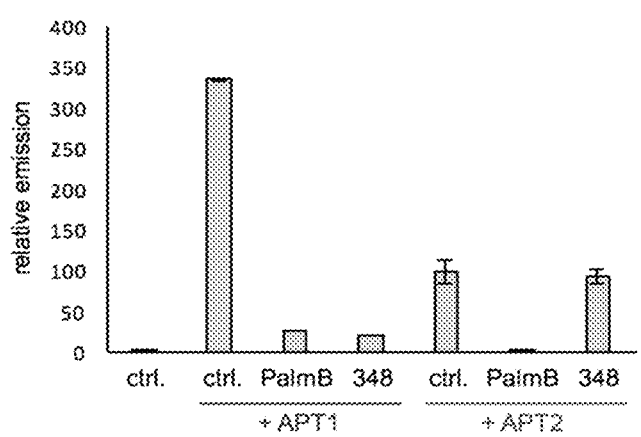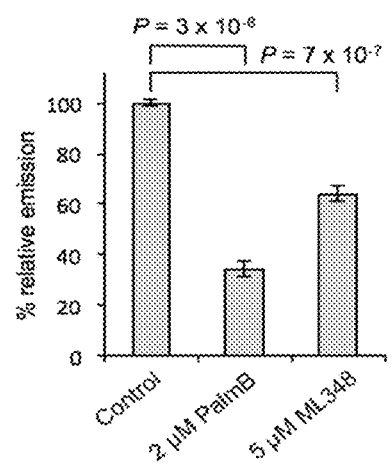
FIG. 7
FIG. 8

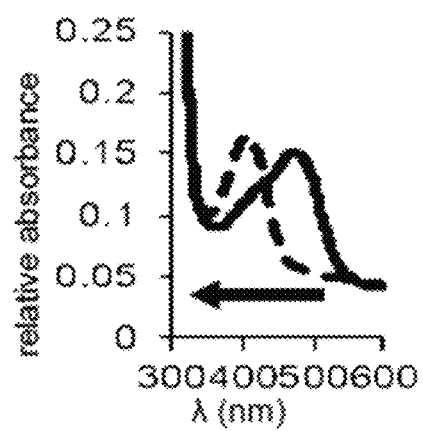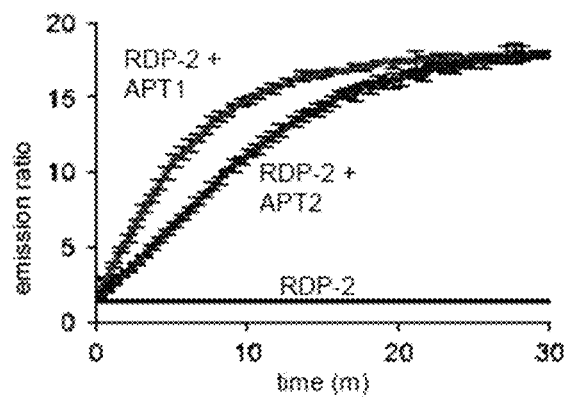
FIG. 20A
FIG. 20B

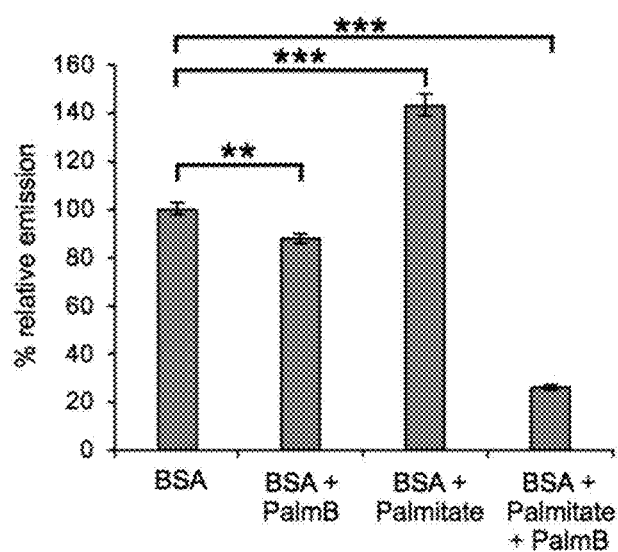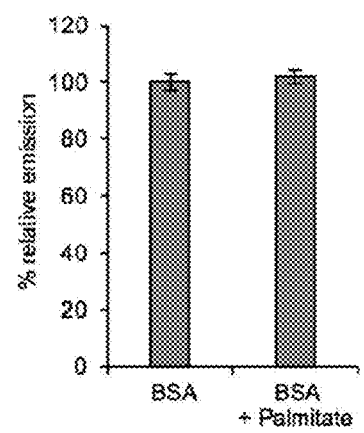
FIG. 39                    FIG. 40

SYNTHETIC SUBSTRATES FOR ENZYMES THAT CATALYZE REACTIONS OF MODIFIED CYSTEINES AND RELATED METHODS

RELATED APPLICATIONS

The presently disclosed subject matter claims the benefit of U.S. Provisional Patent Application Ser. No. 62/428,034, filed Nov. 30, 2016; and of U.S. Provisional Patent Application Ser. No. 62/556,873, filed Sep. 11, 2017, the disclosures of each of which are incorporated herein by reference in their entireties.

STATEMENT OF GOVERNMENT SUPPORT

This invention was made with government support under Grant No. R35-GM119840 awarded by the National Institutes of Health. The government has certain rights in the invention.

TECHNICAL FIELD

The presently disclosed subject matter relates to molecular probes that can detect the activity of enzymes (such as acyl protein thioesterases (APTs) that catalyze reactions of modified cysteine residues, as well as to prodrugs that can be converted to their parent drugs in the presences of such enzymes. The presently disclosed subject matter further provides methods of detecting the activity of enzymes that catalyze reactions of modified cysteine residues, and to methods of detecting and/or treating diseases associated with increased activity of such enzymes.

ABBREVIATIONS

° C.=degrees Celsius
%=percentage
$\lambda_{em}$=emission wavelength
$\lambda_{ex}$=excitation wavelength
μL=microliter
μm=microns
μM=micromolar
APT=acyl protein thioesterase
Boc=tert-butoxycarbonyl
BSA=bovine serum albumin
Cys=cysteine
DMSO=dimethylsulfoxide
DPP=depalmitoylation probe
EGF=epidermal growth factor
FITC=fluorescein isothiocyanate
g=grams
GSH=glutathione
h (or hr)=hours
m (or min)=minutes
mL=milliliter
mM=millimolar
MRI=magnetic resonance imaging
nm=nanometer
nM=nanomolar
PalmB=palmostatin B
PATs=protein acyltransferases
PTM=post-translational modification
RDP=ratiometric depalmitoylation probe
S=seconds
shRNA=short hairpin ribonucleic acid
siRNA=short interfering ribonucleic acid
Trt=triphenyl methane
UV-Vis=ultraviolet-visible

BACKGROUND

Palmitoylation and depalmitoylation of cysteine residues on target proteins plays a key role in regulating protein localization, trafficking, and resultant cell signaling. See Linder and Deschenes (2007) Nat Rev Mol Cell Biol 8, 74-84; Eisenberg et al. (2013) Biochem Soc Trans 41, 79-83; Topinka and Bredt (1998) Neuron 20, 125-134; and Chan et al. (2016) Nat Chem Biol 12, 282-289. Recent advances in mass spectrometry-based protein profiling techniques have greatly expanded the catalog of human proteins modified by S-palmitoylation to include hundreds of putative targets. See Peng et al. (2016) Curr Opin Chem Biol 30, 77-86; and Hernandez et al. (2013) Curr Opin Chem Biol 17, 20-26. There are 23 protein acyltransferases (PATs) in humans that act as the "writers" that install the lipid modification. See Zhenq et al. (2013) J Am Chem Soc 135, 70782-7085. Acyl protein thioesterases (APTs) are the "erasers" of S-palmitoylation (see Linder and Deschenes (2007) Nat Rev Mol Cell Biol 8, 74-84), including the lyosomal degradation enzyme protein palmitoylthioesterase-1 (see Verkruyse and Hofmann (1996) J Biol Chem 271, 15831-15836) and the putatively cytosolic proteins acyl protein thioesterase 1 (APT1) and acyl protein thioesterase 2 (APT2), which are part of the metabolic serine hydrolase (mSH) superfamily. See Long and Cravatt (2011) Chem Rev 111, 6022-6063. In addition, three previously uncharacterized enzymes, the α/β-hydrolase domain-containing protein 17 members A-C, were recently identified as regulators of N-Ras depalmitoylation and are potentially additional S-palmitoylation erasers. See Lin and Conibear (2015) Elife 4, e11306.

APT enzymes have been proposed to contain no substrate specificity and to act constitutively to depalmitoylate proteins universally from intracellular membranes. See Rocks et al. (2010) Cell 141, 458-471. However, several lines of evidence suggests that S-palmitoylation is, in fact, regulated and dynamic, including findings that PSD-95 is rapidly depalmitoylated following glutamate stimulation (see El-Husseini et al. (2002) Cell 108, 849-863), that activation of FGF receptors by FGF2 leads to palmitoylation of cell adhesion molecules in neurons (see Ponimaskin et al. (2008) J Neurosci 28, 8897-8907), and that T-cell activation induces accelerated palmitate cycling. See Zhang et al. (2010) Proc Natl Acad Sci USA 107, 8627-8632. Indeed, the APT enzymes themselves can be S-palmitoylated (see Kong et al. (2013) J Biol Chem 288, 9112-9125), potentially resulting in auto-regulatory mechanisms. To address the roles of APT activities in cell signaling, several classes of small molecule inhibitors have been developed, including the pan-depalmitoylase inhibitor palmostatin B (PalmB) and the APT1- and APT2-specific inhibitors ML348 and ML349. See Davda and Martin (2014) Medchemcomm 5, 268-276; Dekker et al. (2010) Nat Chem Biol 6, 449-456; Rusch et al. (2011) Angew Chem Int Ed Engl 50, 9838-9842; and Adibekian et al. (2012) J Am Chem Soc 134, 10345-10348.

Current approaches to study S-palmitoylation primarily involve proteomics, monitoring the trafficking of microinjected fluorescent substrates (see Dekker et al. (2010) Nat Chem Biol 6, 449-456; and Gormer et al. (2012) Chembiochem 13, 1017-1023), or the use of cell-permeable substrate mimetics. See Creaser and Peterson (2002) J Am Chem Soc 124, 2444-2445. These approaches reveal the balance between palmitoylation and depalmitoylation, but cannot reveal potential upstream regulatory mechanisms particularly related to the depalmitoylases.

Accordingly, there is an ongoing need for further methods for studying S-palmitoylation and other PTMs of cysteines. More particularly, there is an ongoing need for additional methods to study the regulation and dynamics of S-palmitoylation, such as methods that can monitor the activity levels of depalmitoylases in physiological relevant contexts, such as in live cells and heterogeneous tissues. There is also a need for additional synthetic molecular probes that can detect the activity of depalmitoylases and related enzymes. For example, there is the need for synthetic probes containing chemical linkers that can be cleaved in the presence of depalmitoylases or ratiometric probes that can undergo a change in detectable properties in the presence of depalmitoylases. There is also the need for synthetic molecular probes with good water solubility.

SUMMARY

In some embodiments, the presently disclosed subject matter provides a compound having a structure of Formula (Ia) or (Ib):

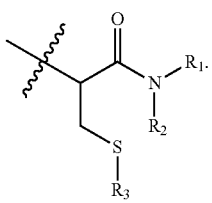
(Ia)

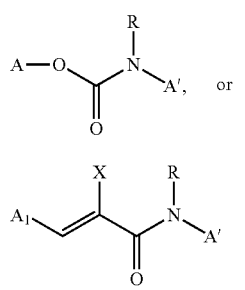
(Ib)

wherein: A is a residue of a compound A-OH, wherein A-OH is a pro-fluorescent, fluorescent, bio-luminescent, magnetic resonance imaging (MRI)-detectable or therapeutically active compound; $A_1$ is a residue of a compound $A_1$-H, wherein $A_1$-H is a fluorescent or bioluminescent compound; X is H or an electron-withdrawing moiety, wherein the electron-withdrawing moiety is selected from the group comprising CN, $NO_2$, —C(=O)H, keto, and amido; R is selected from the group comprising H, alkyl, substituted alkyl, aralkyl, substituted aralkyl, aryl, and substituted aryl; and A' is selected from the group comprising:

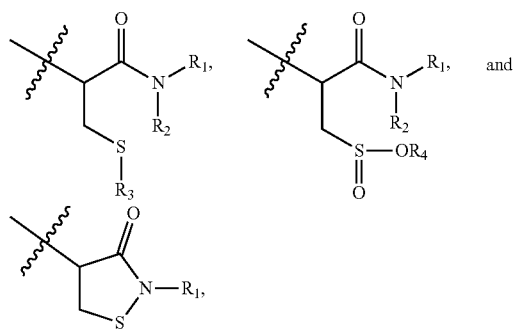

wherein: $R_1$ is selected from the group comprising H, alkyl, substituted alkyl, aralkyl, substituted aralkyl, aryl, and substituted aryl; and $R_2$ is selected from the group comprising H, alkyl, substituted alkyl, aralkyl, substituted aralkyl, aryl, and substituted aryl; or wherein $R_1$ and $R_2$ together with the nitrogen atom to which they are attached form an amino acid or peptidyl residue; $R_3$ is selected from the group comprising alkyl, substituted alkyl, aralkyl, substituted aralkyl, aryl, substitute aryl, —S(=O)$R_5$, —SH, —N(=O), S-glutathione, and —C(=O)$R_5$; $R_4$ is selected from H and $R_5$; and $R_5$ is selected from the group comprising alkyl, substituted alkyl, aralkyl, and substituted aralkyl; or a pharmaceutically acceptable salt thereof. In some embodiments, A' is

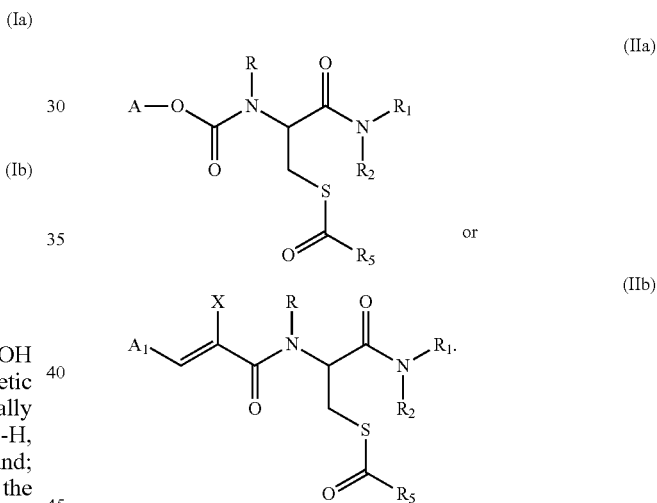

In some embodiments, the compound has a structure of Formula (IIa) or (IIb):

(IIa)

or (IIb)

In some embodiments, $R_5$ is —(CH$_2$)$_n$CH$_3$ wherein n is 1-18. In some embodiments, $R_1$ and $R_2$ together with the nitrogen atom to which they are attached form an amino acid or peptidyl residue and further wherein the amino acid or peptidyl residue comprises a positively charged amino acid residue.

In some embodiments, the compound has a structure of Formula (Ia) wherein A is a residue of a compound A-OH, wherein A-OH is a pro-fluorescent, fluorescent or a therapeutically active compound and wherein the OH of the compound A-OH is a phenolic group. In some embodiments, A-OH is a rhodol or a fluorescein derivative.

In some embodiments, A is a residue of a compound A-OH, wherein A-OH is a therapeutically active compound and wherein the compound of Formula (Ia) is a carbamate prodrug of the compound A-OH. In some embodiments, the presently disclosed subject matter provides a pharmaceutical composition comprising a carbamate prodrug of the compound A-OH (i.e., wherein the carbamate prodrug is a compound of Formula (Ia), wherein A is a residue of a compound A-OH, wherein A-OH is a therapeutically active compound); and a pharmaceutically acceptable carrier.

In some embodiments, the compound has a structure of Formula (Ib), wherein A is a residue of a compound $A_1$-H wherein $A_1$-H is a fluorescent compound. In some embodiments, $A_1$-H is a coumarin derivative. In some embodiments, X is CN.

In some embodiments, the compound is selected from the group comprising:

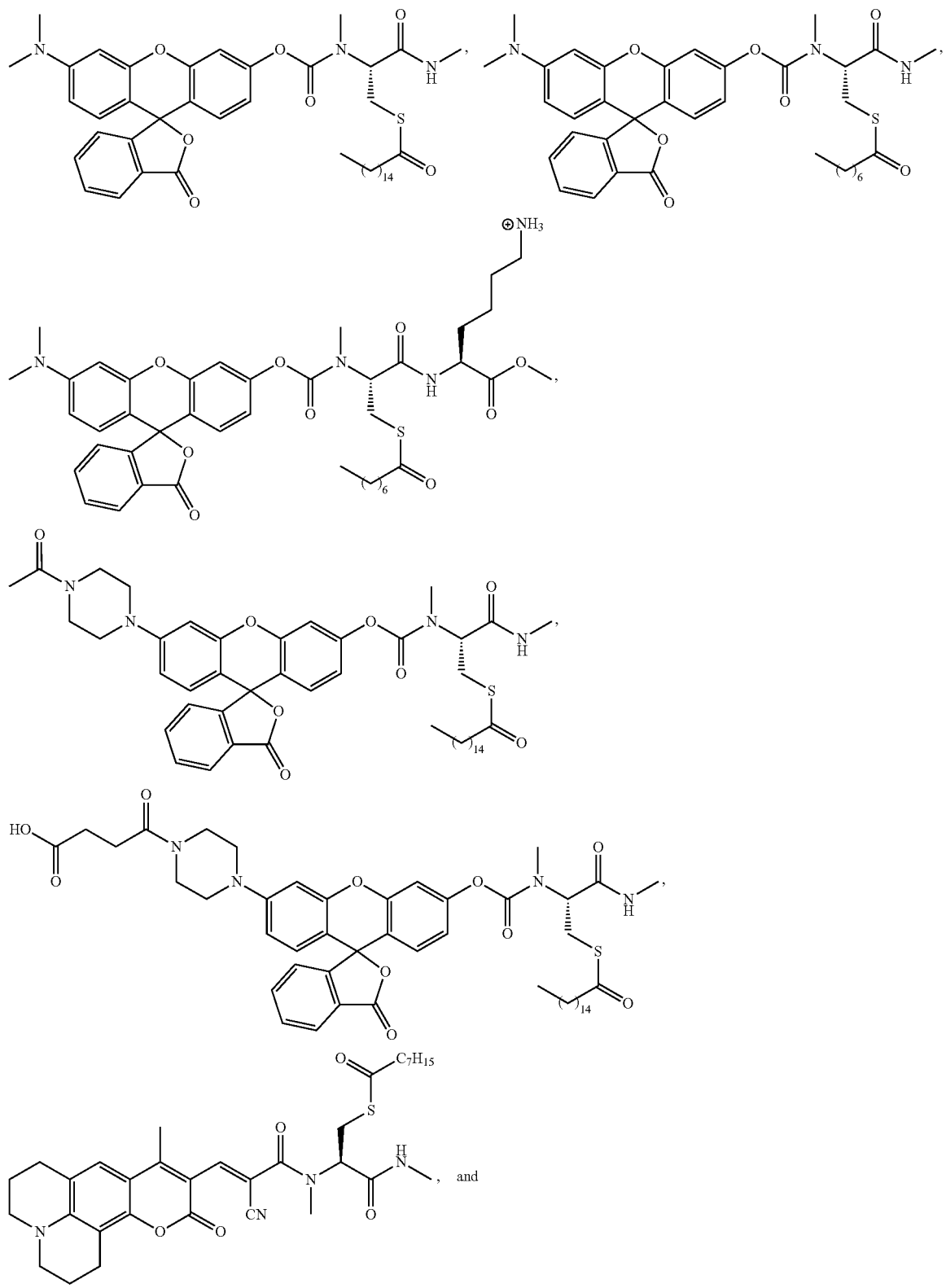

-continued

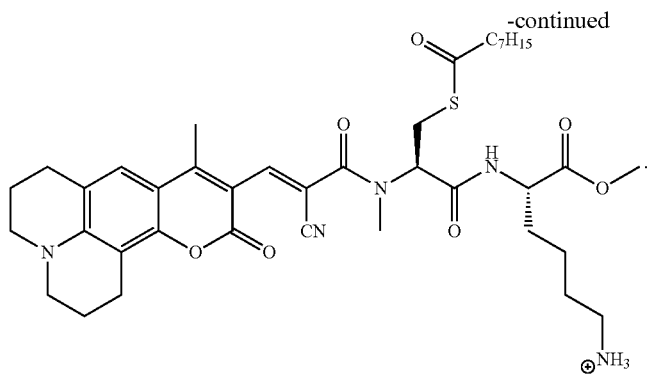

In some embodiments, the presently disclosed subject matter provides a method of detecting enzymatic activity in a sample, the method comprising: contacting the sample with a compound of Formula (Ia) or (Ib):

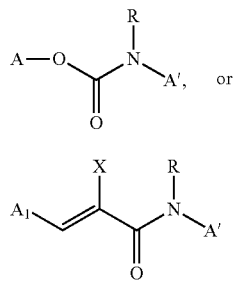

wherein: A is a residue of a compound A-OH, wherein A-OH is a pro-fluorescent or fluorescent compound; $A_1$ is a residue of a compound $A_1$-H, wherein $A_1$-H is a fluorescent compound; X is H or an electron-withdrawing moiety, wherein the electron-withdrawing moiety is selected from the group comprising CN, $NO_2$, —C(=O)H, keto, and amido; R is selected from the group comprising H, alkyl, substituted alkyl, aralkyl, substituted aralkyl, aryl, and substituted aryl; and A' is selected from the group comprising:

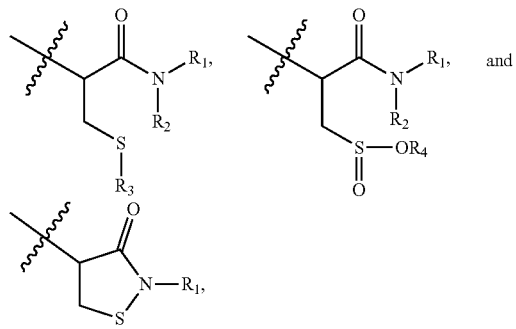

wherein: $R_1$ is selected from the group comprising H, alkyl, substituted alkyl, aralkyl, substituted aralkyl, aryl, and substituted aryl; and $R_2$ is selected from the group comprising H, alkyl, substituted alkyl, aralkyl, substituted aralkyl, aryl, and substituted aryl; or wherein $R_1$ and $R_2$ together with the nitrogen atom to which they are attached form an amino acid or peptidyl residue; $R_3$ is selected from the group comprising alkyl, substituted alkyl, aralkyl, substituted aralkyl, aryl, substitute aryl, —S(=O)$R_5$, —SH, —N(=O), S-glutathione, and —C(=O)$R_5$; $R_4$ is selected from H and $R_5$; and $R_5$ is selected from the group comprising alkyl, substituted alkyl, aralkyl, and substituted aralkyl; or a pharmaceutically acceptable salt thereof; and detecting one or more fluorescence signals in the sample, wherein detecting the one or more fluorescence signals detects the presence and/or amount of enzymatic activity of an enzyme in the sample that catalyzes a reaction of a modified cysteine substrate.

In some embodiments, the enzyme is a thioesterase, an abhydrolyase domain containing 17A (ABHD17) protein, or a thioetherase. In some embodiments, the sample is an in vitro sample. In some embodiments, the sample comprises a live cell, tissue, or organ. In some embodiments, the sample is a subject or a cell, tissue, or fluid obtained from a subject and wherein detecting enzymatic activity further detects a disease state associated with increased or decreased activity of an enzyme that catalyzes a reaction of a modified cysteine substrate.

In some embodiments, the presently disclosed subject matter provides a method of treating a disease in a subject in need of treatment thereof, wherein the method comprises: administering to the subject a compound of Formula (Ia):

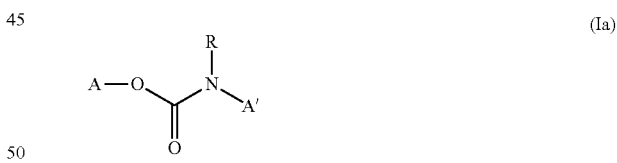

wherein: A is a residue of a compound A-OH, wherein A-OH is a therapeutic compound; R is selected from the group comprising H, alkyl, substituted alkyl, aralkyl, substituted aralkyl, aryl, and substituted aryl; and A' is selected from the group comprising:

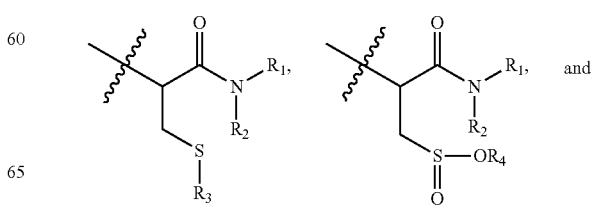

-continued

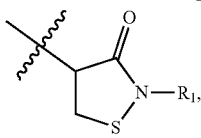

wherein $R_1$ is selected from the group comprising H, alkyl, substituted alkyl, aralkyl, substituted aralkyl, aryl, and substituted aryl; and $R_2$ is selected from the group comprising H, alkyl, substituted alkyl, aralkyl, substituted aralkyl, aryl, and substituted aryl; or wherein $R_1$ and $R_2$ together with the nitrogen atom to which they are attached form an amino acid or peptidyl residue; $R_3$ is selected from the group comprising alkyl, substituted alkyl, aralkyl, substituted aralkyl, aryl, substitute aryl, —S(═O)$R_5$, —SH, —N(═O), S-glutathione, and —C(═O)$R_5$; $R_4$ is selected from H and $R_5$; and $R_5$ is selected from the group comprising alkyl, substituted alkyl, aralkyl, and substituted aralkyl; or a pharmaceutically acceptable salt or pharmaceutical formulation thereof. In some embodiments, the disease is selected from the group comprising cancer; a neurological disorder; a neurodegenerative disease; a metabolic disorder, diabetes, an autoimmune disease; an infectious disease; liver disease; kidney disease; atherosclerosis; and hypertension.

Accordingly, it is an object of the presently disclosed subject matter to provide molecular probes and prodrugs that are responsive to enzymes that catalyze reactions of modified cysteine residues, as well as related pharmaceutical formulations, methods of detecting enzymatic activity and disease, and methods of treating disease.

An object of the presently disclosed subject matter having been stated hereinabove, and which is achieved in whole or in part by the presently disclosed subject matter, other objects will become evident as the description proceeds hereinbelow.

BRIEF DESCRIPTION OF THE DRAWINGS

FIG. 3A is a graph showing the ultraviolet-visible (UV-Vis) spectrum of a 100 micromolar (μM) solution of depalmitoylation probe 1 (DPP-1) in 4-(2-hydroxyethyl)-1-piperazineethanesulfonic acid (HEPES) buffer (20 millimolar mM, at pH 7.4, 150 mM sodium chloride (NaCl) and 1% Triton X-100).

FIG. 3B is a graph showing the ultraviolet-visible (UV-Vis) spectrum of a 100 micromolar (μM) solution of depalmitoylation probe 2 (DPP-2) in 4-(2-hydroxyethyl)-1-piperazineethanesulfonic acid (HEPES) buffer (20 millimolar mM, at pH 7.4, 150 mM sodium chloride (NaCl) and 1% Triton X-100).

FIG. 3C is a graph showing the ultraviolet-visible (UV-Vis) spectrum of a 100 micromolar (μM) solution of depalmitoylation probe 3 (DPP-3) in 4-(2-hydroxyethyl)-1-piperazineethanesulfonic acid (HEPES) buffer (20 millimolar mM, at pH 7.4, 150 mM sodium chloride (NaCl) and 1% Triton X-100).

FIG. 3D is a graph showing the ultraviolet-visible (UV-Vis) spectrum of a 5 micromolar (μM) solution of N,N-dimethylrhodol in 4-(2-hydroxyethyl)-1-piperazineethanesulfonic acid (HEPES) buffer (20 millimolar mM, at pH 7.4, 150 mM sodium chloride (NaCl) and 1% Triton X-100).

FIG. 7 is a graph showing the in vitro effect of small molecule inhibitors to block the signal of depalmitoylation probe 3 (DPP-3). The fluorescence response of DPP-3 was quantified for 5 micromolar (μM) DPP-3 treated with either 50 nanomolar (nM) purified acyl protein thioesterase 1 (APT1) or 50 nM acyl protein thioesterase 2 (APT2) for 30 minutes each in the presence of 50 μM of either pan-APT inhibitor palmostatin B (PalmB) or APT1-specific inhibitor ML348 ("348"). As controls, the response was also measured for DPP-3 with each of APT1 and APT2 alone ("ctrl"), as well as for DPP-3 without enzyme ("ctrl"). The excitation wavelength ($\lambda_{ex}$) was 490/9 nanometers (nm) and the emission wavelength ($\lambda_{em}$) was 545/20 nm. Error bars are standard deviation (n=4).

FIG. 8 is a graph showing the relative fluorescence response of depalmitoylation probe 2 (DPP-2) in human embryonic kidney (HEK293T) cells. Five micromolar (μM) DPP-2 was loaded into HEK293T cells for 15 minutes after pretreatment with either dimethylsulfoxide (DMSO, "Control") or 5 μM inhibitor (either pan-acyl protein thioesterase (APT) inhibitor palmostatin B (PalmB) or acyl protein thioesterase 1 (APT1)-specific inhibitor ML348), and then analyzed by fluorescence microscopy. Error bars are ±standard deviation (n=6). Statistical analysis was performed with a two-tailed Student's t-test with unequal variance.

FIG. 20A is a graph showing the ultraviolet-visible (UV-Vis) absorption spectra of ratiometric depalmitoylation probe 2 (RDP-2; 15 micromolar (μM), solid line), and of its deacylated form (dotted line) at pH 7.4.

FIG. 20B is a graph showing the ratiometric response of 1 micromolar (μM) ratiometric depalmitoylation probe-2 (RDP-2) to 200 nanomolar (nM) acyl protein thioesterase 1 (APT1) or 200 nM acyl protein thioesterase 2 (APT2). Data is shown as the ratio of the emission of the RDP-2 divided by the emission of its deacylated form. Error bars are ±standard deviation. For comparison the response of RDP-2 with no enzyme is also shown.

FIG. 39 is a graph showing palmitate-induced activation of S-depalmitoylase activity measured using depalmitoylation probe 5 (DPP-5) in human live carcinoma (HepG2) cells. HepG2 cells were pretreated with 1% bovine serum albumin (BSA) with or without 1 millimolar (mM) palmitate, treated with 1 micromolar (μM) Hoechst 33342 nuclear stain and dimethylsulfoxide (DMSO) or 5 μM palmostatin B (PalmB) for 30 minutes, washed, loaded with 1 μM DPP-5 for 20 minutes, and then analyzed by epifluorescence microscopy. Error bars are standard errors of the mean (n=10). Statistical analysis was performed with a two-tailed Student's t-test with unequal variance. P value<0.003, *P value<0.0001.

FIG. 40 is a graph showing the effect of palmitate-induced activation of S-depalmitoylase activity on diacetyl rhodol in human live carcinoma (HepG2) cells. HepG2 cells were pretreated with 1% bovine serum albumin (BSA) with or without 1 millimolar (mM) palmitate, treated with 1 micromolar (μM) Hoechst 33342 nuclear stain for 30 minutes, washed, loaded with 1 μM diacetyl rhodol for 20 minutes, and then analyzed by epifluorescence microscopy.

DETAILED DESCRIPTION

Figure 1:
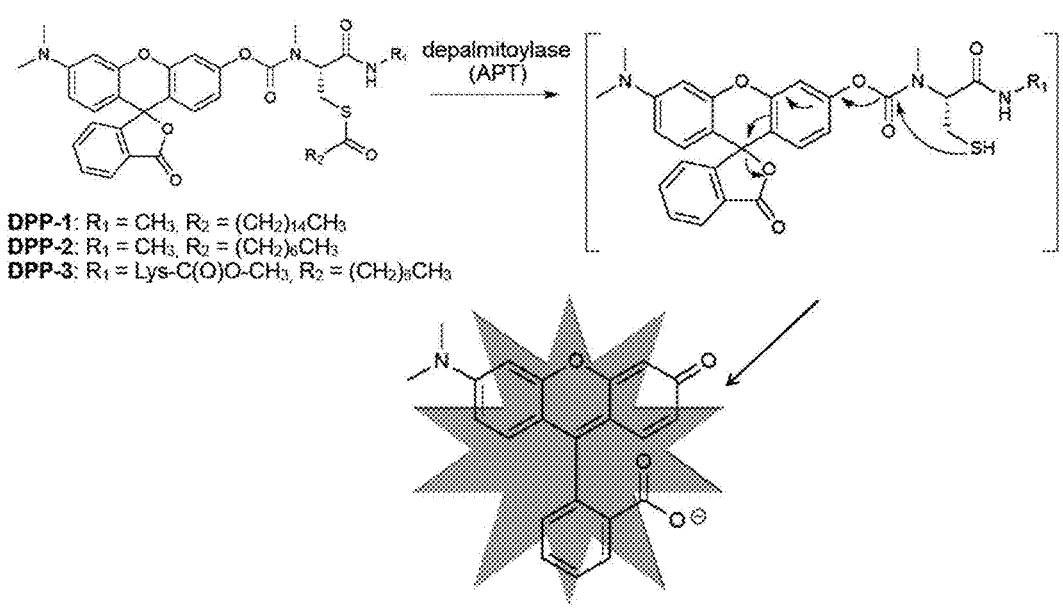
FIG. 1 is a schematic diagram showing the design and activation mechanism of exemplary depalmitoylation probes (DPPs) of the presently disclosed subject matter that have cleavable linkers. The structures of three particular exemplary DPPs for determining cysteine deacylase activity are shown, depalmitoylation probe 1 (DPP-1), depalmitoylation probe 2 (DPP-2), and depalmitoylation probe 3 (DPP3). These DPPs include a cysteine residue tethered to a pro-fluorescent molecule by a biologically stable carbamate linker. Deacylase activity on the cysteine releases the thiol form of the probe, which rapidly cyclizes, breaking the carbamate linkage and releasing a fluorescent product. In some embodiments, the physical and biological properties of the probe can be tuned by modulating the acyl modification on the thiol ($R_2$) and the C-terminal amide modification on the cysteine ($R_1$).

The presently disclosed subject matter will now be described more fully. The presently disclosed subject matter can, however, be embodied in different forms and should not be construed as limited to the embodiments set forth herein below and in the accompanying Examples. Rather, these embodiments are provided so that this disclosure will be thorough and complete, and will fully convey the scope of the embodiments to those skilled in the art.

All references listed herein, including but not limited to all patents, patent applications and publications thereof, and scientific journal articles, are incorporated herein by reference in their entireties to the extent that they supplement, explain, provide a background for, or teach methodology, techniques, and/or compositions employed herein.

Throughout the specification and claims, a given chemical formula or name shall encompass all optical and stereoisomers, as well as racemic mixtures where such isomers and mixtures exist.

I. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs.

Following long-standing patent law convention, the terms "a," "an," and "the" refer to "one or more" when used in this application, including the claims.

The term "and/or" when used in describing two or more items or conditions, refers to situations where all named items or conditions are present or applicable, or to situations wherein only one (or less than all) of the items or conditions is present or applicable.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" can mean at least a second or more.

The term "comprising," which is synonymous with "including," "containing," or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

Unless otherwise indicated, all numbers expressing quantities of size, temperature, time, weight, volume, concentration, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value is meant to encompass variations of in one example ±20% or +10%, in another example ±5%, in another example ±1%, and in still another example ±0.1% from the specified amount, as such variations are appropriate to perform the disclosed methods.

Numerical ranges recited herein by endpoints include all numbers and fractions subsumed within that range (e.g. 1 to 5 includes, but is not limited to, 1, 1.5, 2, 2.75, 3, 3.90, 4, and 5).

As used herein the term "alkyl" can refer to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms or having up to about 5 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. In some embodiments, there can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Heteroaryl" as used herein refers to an aryl group that contains one or more non-carbon atoms (e.g., O, N, S, Se, etc) in the backbone of a ring structure. Nitrogen-containing heteroaryl moieties include, but are not limited to, pyridine, imidazole, benzimidazole, pyrazole, pyrazine, triazine, pyrimidine, and the like.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH2-); ethylene (—CH2-CH2-); propylene (—(CH2)3-); cyclohexylene (—C6H10-); —CH=CH—CH=CH—; —CH=CH—CH2-; —(CH2)q-N(R)—(CH2)r-, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH2-O—); and ethylenedioxyl (—O—(CH2)2-O—). An alkylene group can have about 2 to about 3 carbon atoms and can further have 6-20 carbons.

"Arylene" refers to a bivalent aromatic group.

"Aralkylene" refers to a bivalent groups including both arylene and alkylene moieties.

As used herein, the term "acyl" refers to a carboxylic acid group wherein the —OH of the carboxylic acid group has been replaced with another substituent. Thus, an acyl group can be represented by RC(=O)—, wherein R is an H, alkyl, substituted alkyl, aralkyl, substituted aralkyl, aryl, or substituted aryl group as defined herein. Specific examples of acyl groups include formyl (i.e., —C(=O)H), acetyl, and benzoyl.

The term "keto" as used herein refers to the group R—C(=O)—, wherein R is alkyl, substituted alkyl, aralkyl, substituted aralkyl, aryl, and substituted aryl.

"Aralkyl" refers to an aryl-alkyl-group wherein aryl and alkyl are as previously described, and can include substituted aryl and substituted alkyl. Exemplary aralkyl groups include benzyl, phenylethyl, and naphthylmethyl.

The term "thioether" refers to the —SR group, wherein R is alkyl, substituted alkyl, aralkyl, substituted aralkyl, aryl or substituted aryl.

The term "thioester" refers to the —S—C(=O)R group, wherein R is alkyl, substituted alkyl, aralkyl, substituted aralkyl, aryl, or substituted aryl.

The terms "hydroxyl" and "hydroxyl" refer to the —OH group.

The term "phenol" as used herein can refer to a compound of the formula R—OH group, wherein R is aryl or substituted aryl.

The term "phenolic" refers to a hydroxyl group that is directly attached to an aromatic group, e.g., a phenyl ring, a napthyl ring, etc.

The terms "mercapto" or "thiol" refer to the —SH group.

The term "carboxyl" refers to the —C(=O)— group.

The terms "carboxylate" and "carboxylic acid" can refer to the groups —C(=O)O⁻ and —C(=O)OH, respectively. In some embodiments, "carboxylate" can refer to either the —C(=O)O⁻ or —C(=O)OH group.

The term "amido" refers to the group —C—C(=O)—NR$_1$R$_2$, wherein R$_1$ and R$_2$ are independently H, alkyl, substituted alkyl, aralkyl, substituted aralkyl, aryl or substituted aryl.

The term "carbamate" refers to the group —O—C(=O)—NR—, wherein R is H, alkyl, substituted alkyl, aralkyl, substituted aralkyl, aryl, or substituted aryl.

The term "aliphatic" as used herein refers to a hydrocarbon compound or moiety that is not aromatic. The compound or moiety can be saturated or partially or fully unsaturated (i.e., can include alkenyl and/or alkynyl groups). In some embodiments, the term "aliphatic" refers to a chemical moiety wherein the main chain of the chemical moiety does not comprise an arylene group.

A line crossed by a wavy line, e.g., in the structure:

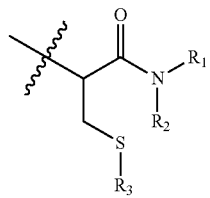

indicates the site where a chemical moiety can bond to another group.

The term "electron-withdrawing" refers to an atom, substituent, or moiety that draws electron density from neighboring atoms toward itself (e.g., via inductive or resonance effects). In some embodiments, the electron-withdrawing group is electron-withdrawing compared to a hydrogen atom. Exemplary electron withdrawing groups include, but are not limited to, cyano (i.e., —CN), nitro (i.e., —NO$_2$), and acyl (e.g., formyl, keto, and amido).

The term "peptide" as used herein refers to a polymer of amino acid residues, wherein the polymer can optionally further contain a moiety or moieties that do not consist of amino acid residues (e.g., an alkyl group, an aralkyl group, an aryl group, a protecting group, or a synthetic polymer, such as, but not limited to a biocompatible polymer). The term applies to amino acid polymers in which one or more amino acid residue is an artificial chemical mimetic of a corresponding naturally occurring amino acid, as well as to naturally occurring amino acid polymers and non-naturally occurring amino acid polymer.

The terms "peptidyl" and "peptidyl moiety" refer to a monovalent peptide or peptide derivative (e.g., a peptide comprising one or more terminal or side chain protecting or other moieties to mask a reactive functional group).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs are compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium.

Such analogs have modified R groups (e.g., norleucine) or modified peptide backbones, but retain the same basic chemical structure as a naturally occurring amino acid. Amino acid mimetics are chemical compounds that have a structure that is different from the general chemical structure of an amino acid, but that functions in a manner similar to a naturally occurring amino acid.

The term "amino acid residue" as used herein refers to a monovalent amino acid or derivative thereof. In some embodiments, the term "amino acid residue" refers to the group —NHC(R')C(=O)OR", wherein R' is an amino acid side chain or protected derivative thereof and wherein R" is H or a carboxylic acid protecting group, e.g., methyl.

"Pharmaceutically acceptable" refers to those carriers, compositions, and/or dosage forms that are, within the scope of sound medical judgment, suitable for contact with the tissues of human beings and animals without excessive toxicity, irritation, allergic response, or other problems or complications commensurate with a reasonable benefit/risk ratio. Thus, in some embodiments, the presently disclosed compounds can be provided in formulations comprising the compound and a carrier that is pharmaceutically acceptable for use in humans.

In some embodiments, "treatment" or "treating" refers to an amelioration of disease or disorder, or at least one discernible symptom thereof. "Treatment" or "treating" also refers to an amelioration of at least one measurable physical parameter associated with a disease or disorder that is not necessarily discernible by the subject. "Treatment" or "treating" can also refer to inhibiting the progression of a disease or disorder either physically (e.g., stabilization of a discernible symptom), physiologically (e.g., stabilization of a physical parameter), or both. "Treatment" or "treating" also refers to delaying the onset of a disease or disorder.

The term "therapeutically active" refers to a compound that has a biological activity that can treat a disease or disorder.

The term "prodrug" as used herein refers to a compound that generates a therapeutically active compound as a result of spontaneous chemical reaction(s), enzyme catalyzed chemical reaction(s), and/or metabolic chemical reaction(s), or a combination of each. In particular embodiments, as used herein the term "prodrug" refers to a carbamate prodrug of a therapeutically active alcohol or phenol that can be converted to the therapeutically active compound as a result of a combination of an enzyme catalyzed reaction that transforms a sulfur containing group in the prodrug into a thiol, followed by a ring forming reaction between the sulfur of the thiol group and the carbonyl carbon of the carbamate, resulting in the cleavage of the carbamate linkage. Thus, prodrugs can undergo some form of a chemical transformation to produce a compound that is biologically active or is a precursor of a biologically active compound. In some cases, the prodrug is biologically active, usually less than the drug itself, and serves to improve drug efficacy or safety through improved oral bioavailability, pharmacodynamic half-life, etc. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound.

The term "pro-fluorescent" as used herein refers to a compound or complex that generates a fluorescent compound as a result of spontaneous chemical reaction(s), enzyme catalyzed chemical reaction(s), and/or metabolic chemical reaction(s), or a combination of each. In particular embodiments, as used herein the term "pro-fluorescent" refers to a carbamate conjugate of a fluorescent alcohol or phenol that can be converted to a fluorescent or more fluorescent compound as a result of a combination of an enzyme catalyzed reaction that transforms a sulfur containing group in the prodrug into a thiol, followed by a ring forming reaction between the sulfur of the thiol group and the carbonyl carbon of the carbamate, resulting in the cleavage of the carbamate linkage. Thus, pro-fluorescent compounds can undergo some form of a chemical transformation to produce a compound that is fluorescent or is a precursor of a fluorescent compound.

The term "bioluminescent" refers to a compound or moiety that produces light under physiological conditions (e.g., a particular pH or the presence of a particular product or intermediate of a biological process, such as but not limited to, hydrogen peroxide or peroxynitrite) and/or in the presence of an enzyme. Thus, for example, bioluminescent probes of the presently disclosed subject matter can include, but are not limited to, caged fluorophores, wherein the fluorophore can include luciferin, rhodamines (e.g., tetramethylrhodamine isothiocyanate), coumarins, resorufin, and dextran-CANPE-HCC (see Li and Zheng, (2012), Photochem Photobio Sci 11, 460-471).

The term "MRI-detectable" refers to a compound or moiety that absorbs and emits radio frequency energy when placed in an external magnetic field. In some embodiments, MRI-detectable probes of the presently disclosed subject matter can include, but are not limited to, caged metals, wherein the metal can include iron oxide, iron platinum, manganese, and gadolinium, or metal-containing compounds.

II. Synthetic Substrates for Enzymes that Catalyze Reactions of Modified Cysteines Protein lipidation of cysteine residues by thioester formation with palmitate, a $C_{16}$ saturated fatty acid, is a prevalent post-translational modification (PTM) in mammalian systems. See, e.g., Linder and Deschenes (2007) Nat Rev Mol Cell Biol 8, 74-84. Hundreds of human proteins are modified by reversible palmitoylation of cysteine residues (S-palmitoylation). However, the regulation of depalmitoylation is poorly understood.

The half-life of the S-palmitoyl group on a given protein target can vary from minutes to days (see Lu and Hofmann (1995) J Biol Chem 270, 7241-7256; and Noland et al. (2016) Structure 24, 179-186) depending on the activity of the S-depalmitoylases on the target. Moreover, the S-depalmitoylases are not statically active, but respond dynamically to cellular changes, such as growth factor signaling and neuronal activation. See El-Husseini et al. (2002) Cell 108, 849-863; and Ponimaskin et al. (2008) J Neurosci 28, 8897-8907. The S-depalmitoylases themselves have been found to be regulated through S-depalmitoylation (see Kong et al. (2013) J Biol Chem 288, 9112-9125), resulting in a complex web of interconnected lipid signaling cascades. Cellular localization of the S-depalmitoylases is a key determinant of activity on a given target (see Kong et al. (2013) J Biol Chem 288, 9112-9125), but other regulatory mechanisms are also believed to be at play. Therefore, methods to measure S-depalmitoylase activities in live cells would be useful to uncover how proteome S-palmitoylation levels are regulated through dynamic S-depalmitoylases.

Provided in accordance with some embodiments of the presently disclosed subject matter are small molecule probes to monitor the endogenous activity levels of "erasers" of S-palmitoylation, such as acyl protein thioesterases (APTs), as well as erasers of other cysteine PTMs. As described below, live-cell analysis with the presently disclosed probes reveals rapid growth factor-mediated inhibition of the depalmitoylation activity of APTs, exposing a new regulatory mechanism of dynamic lipid signaling.

The presently disclosed subject matter provides in some aspects synthetic probe compounds that report on or respond to endogenous levels of enzymatic activity with respect to cysteine post-translational modifications (PTMs). These probes include a substrate moiety (i.e., a moiety that acts as a substrate for an enzyme that catalyzes a reaction of a modified cysteine) and a reporter moiety. In some embodiments, the presently disclosed subject matter provides a compound having a structure of Formula (Ia) or (Ib):

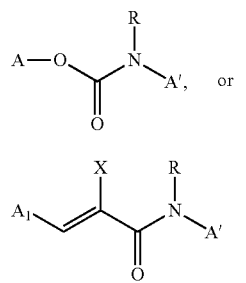

wherein A is an aliphatic or aromatic moiety; $A_1$ is an aromatic moiety; X is H or an electron-withdrawing moiety; R is selected from the group comprising H, alkyl, substituted alkyl, aralkyl, substituted aralkyl, aryl, or substituted aryl; and A' is selected from the group comprising:

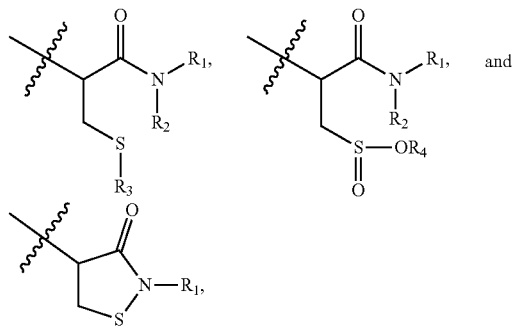

wherein $R_1$ and $R_2$ are each independently selected from the group comprising H, alkyl, substituted alkyl, aralkyl, substituted aralkyl, aryl, substituted aryl; or wherein $R_1$ and $R_2$ together with the nitrogen atom to which they are attached form an amino acid or peptidyl residue; $R_3$ is selected from the group comprising alkyl, substituted alkyl, aralkyl, substituted aralkyl, aryl, substitute aryl, —S(=O)$R_5$, —SH, —N(=O), S-glutathione, and —C(=O)$R_5$; $R_4$ is selected from H and $R_5$; and $R_5$ is selected from the group comprising alkyl, substituted alkyl, aralkyl, and substituted aralkyl; or a pharmaceutically acceptable salt thereof.

In some embodiments, A' is

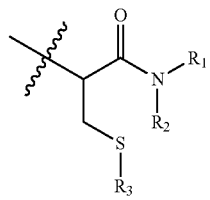

In some embodiments, $R_3$ is an acyl group (i.e., —C(=O)$R_5$), such that the compound of Formula (Ia) or (Ib) is a compound having a structure of Formula (IIa) or (IIb):

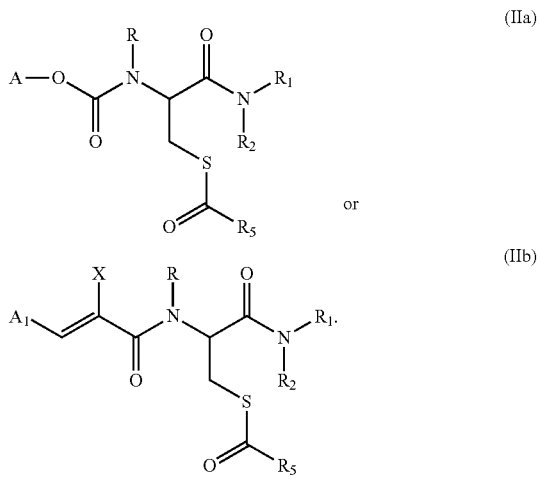

Thus, the compound can comprise an acylated thiol residue. In some embodiments, $R_5$ is —(CH$_2$)$_n$CH$_3$, wherein n is 1-18. In some embodiments, n is 14 so that the $R_5$ group is the same as that in a naturally occurring S-palmitoylated protein. In some embodiments, n is smaller than 14. Thus in some embodiments, n is 1, 2, 3, 4, 5, 6, 7, 8, 9, 10, 11, or 12. In some embodiments, n is 6 or 7.

In some embodiments, R is H or alkyl. For instance, in some embodiments, R is $C_1$-$C_5$ alkyl (e.g., methyl, ethyl, n-propyl, isopropyl, n-butyl, sec-butyl, n-pentyl, iso-pentyl, neo-pentyl, etc.). In some embodiments, R is methyl.

In some embodiments, $R_1$ and $R_2$ are each independently H or alkyl. For example, in some embodiments, $R_1$ is $C_1$-$C_5$ alkyl (e.g., methyl, ethyl, n-propyl, isopropyl, n-butyl, sec-butyl, n-pentyl, iso-pentyl, neo-pentyl, etc.). In some embodiments, $R_1$ is methyl. In some embodiments, $R_2$ is H.

In some embodiments, $R_1$ and $R_2$ together with the nitrogen atom to which they are attached form an amino acid residue or a peptidyl residue. The amino acid or peptidyl residue can comprise a charged amino acid side chain, for example a positively charged amino acid chain, or another modification to enhance the water solubility of the probe. In some embodiments, $R_1$ and $R_2$ together form an amino acid or peptidyl residue comprising a lysine, histidine or arginine residue. In some embodiments, the amino acid or peptidyl residue comprises a lysine residue. In some embodiments, $R_1$ and $R_2$ together comprises a peptidyl residue (e.g., comprising 2, 3, 4, 5, 6, 7, 8, 9, or 10 amino acid residues) wherein the C-terminal residue (i.e., the residue farthest away from the modified cysteine residue) comprises a positively charged amino acid side chain (e.g., the side chain of a lysine residue). In some embodiments, the amino acid or peptidyl residue comprises a protecting group (e.g., an amino or carboxylate protecting group known in the art of peptide synthesis or another group that masks the reactivity of a reactive functional group). In some embodiments, the amino acid or peptidyl residue comprises a protected carboxylate, e.g., at the C-terminus. In some embodiments, the C-terminal carboxylate is protected as an amide or carbamate moiety.

In some embodiments, the compound is a compound of Formula (Ia). The compound of Formula (Ia) comprises a conjugate including a carbamate linkage between residue A of a parent compound A-OH and an amine having the formula HNR(A'), wherein the amine comprises a modified cysteine residue. In some embodiments, the parent compound A-OH is a pro-fluorescent, fluorescent, bioluminescent, MRI-detectable, and/or therapeutically active compound. Thus, in some embodiments, the carbamate conjugate of Formula (I) can be a prodrug or a pro-fluorescent probe that can release a drug or a fluorescent or pro-fluorescent compound in the presence of an enzyme that targets cysteine PTMs. In some embodiments, A is an aromatic moiety such that the OH of the corresponding parent A-OH compound is a phenolic group. In some embodiments, A is a residue of a parent compound A-OH, wherein A-OH is a xanthene derivative. In some embodiments, A-OH is a rhodol or fluorescein derivative. In some embodiments, A comprises one or more solubility enhancing moieties.

FIG. 1 shows the structures of exemplary depalmitoylation probes (DPPs) of Formula (Ia) (and Formula (IIa)) wherein A is the residue of a parent compound comprising a pro-fluorescent rhodol derivative. The pro-fluorescent rhodol derivative is tethered to an S-acylated peptidyl residue via a carbamate linkage. Although the carbamate linkage is generally stable under physiological conditions, thioesterase activity (e.g., APT activity) on the probe (FIG. 1, top) results in a reaction cascade involving (i) cleavage of the thioester to provide a free thiol group, and (ii) intramolecular reaction of the free thiol group at the carbonyl carbon of the carbamate, which then results in cleavage of the carbamate and release of a fluorescent compound (FIG. 1, bottom).

In some embodiments, the compound of Formula (Ia) or Formula (IIa) is a prodrug of a therapeutically active compound, such as, but not limited to, an alcohol- or a phenol-containing compound known in the art for the treatment of a disease, such as a disease associated with increased activity of an enzyme or enzymes (e.g., APTs) that catalyze reactions of modified cysteine residues. For example, A-OH can be a compound known in the art for the treatment of cancer, a neurological disorder; a neurodegenerative disease; a metabolic disorder (e.g., diabetes); an autoimmune disease; an infectious disease; liver disease; kidney disease; atherosclerosis; or hypertension.

Accordingly, in some embodiments, A is a residue of a compound A-OH, wherein A-OH is a therapeutically active compound and wherein the compound of Formula (Ia) is a carbamate prodrug of the parent compound A-OH. Many biologically active compounds contain one or more phenolic or hydroxyl groups.

Exemplary prodrugs of Formula (Ia) and (IIa) can be based on parent compounds, such as, but not limited to, combretastatin A4, topotecan, fulvestrant, raloxifene, lasofoxifene, bazedoxifene, pipendoxifene, daidzein, resveratrol, equol, acetaminophen nonivamide, niclosamide, acolbifene, amodiaquine, genistein, arzoxifene, coumarin derivatives, such as aesculetin and daphnetin, and resorcinol derivatives, such as luminespib, or their derivatives. In some embodiments, the prodrug of Formula (Ia) or (IIa) or its pharmaceutically acceptable salt is provided as part of a pharmaceutical formulation further comprising a pharmaceutically acceptable carrier.

In some embodiments, the compound is a compound of Formula (Ib). In some embodiments, the compound of Formula (Ib) comprises a conjugate comprising a linker including a Michael acceptor between a moiety $A_1$ derived from a fluorescent or bioluminescent parent compound $A_1$-H and an amine having the formula HNR(A'), wherein the amine comprises a modified cysteine residue. In some embodiments, A is a residue of a compound $A_1$-H, wherein $A_1$-H is a fluorescent compound. For instance, in some embodiments $A_1$-H is a derivative of coumarin, i.e.:

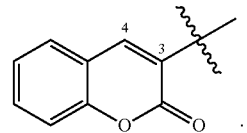 [SMILES: *c1cc2ccccc2oc1=O]

In some embodiments, the coumarin derivative is substituted (e.g., with a $C_1$-$C_5$ alkyl group) at the 4-position. In some embodiments, the coumarin derivative is substituted by a methyl group at the 4-position. In some embodiments, $A_1$-H is an amino coumarin derivative, such as, but not limited to a julolidine-based amino coumarin derivative. In some embodiments, $A_1$ has a structure of the formula:

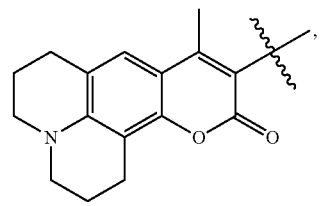 [SMILES: *c1c(C)c2cc3c4c(c2oc1=O)CCCN4CCC3]

optionally wherein one or more aromatic or aliphatic carbon atom is substituted with another group, such as a solubility enhancing group as described further hereinbelow. In some embodiments, the electron-withdrawing group X of Formula (Ib) or (IIb) is CN, NO₂, keto, amido, or formyl. In some embodiments, X is CN.

Figure 2:
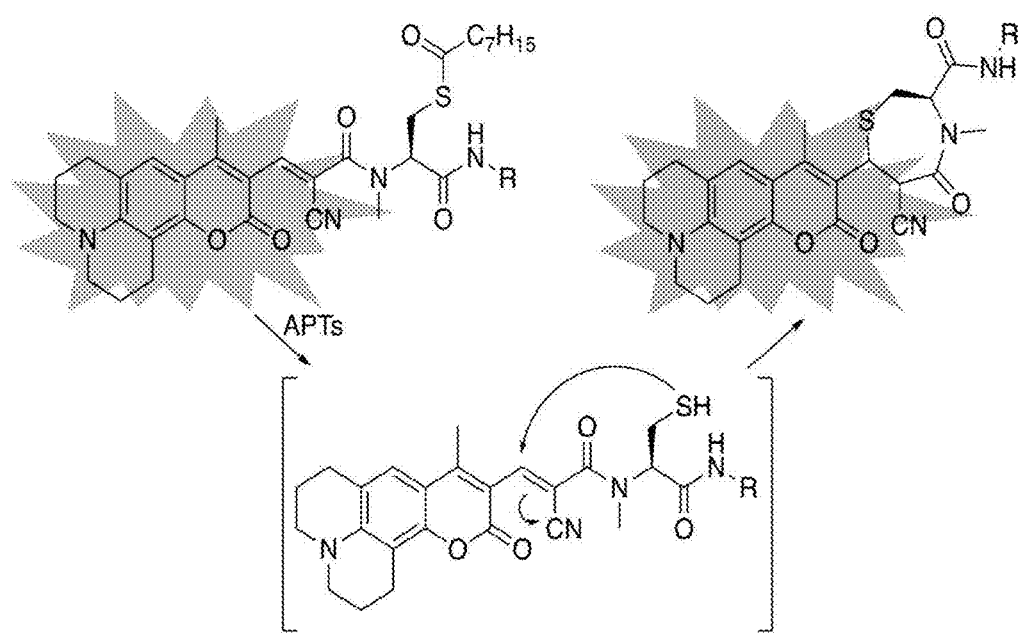
FIG. 2 is a schematic diagram showing the design and activation mechanism of exemplary ratiometric depalmitoylation probes (RDPs) of the presently disclosed subject matter. The RDPs include a S-palmitoyl-cysteine analog residue coupled to a weakly active Michael acceptor moiety at the 3-position of an amino coumarin-based fluorophore. Deacylase activity on the cysteine releases the thiol form of the probe, which undergoes an intramolecular Michael addition to cyclize to provide a seven-membered ring, breaking up the conjugated π-system and causing a change in the spectral properties of the probe.

FIG. 2 shows the structures of exemplary depalmitoylation probe (DPP) compounds of Formula (Ib) (and Formula (IIb)) wherein A₁ is the residue of a parent compound comprising a julolidine-based amino coumarin derivative. The coumarin derivative is tethered at the 3-position of the coumarin core structure to an S-acylated peptidyl residue via a linkage comprising an α,β unsaturated carbonyl group that can serve as a Michael acceptor. Thioesterase activity (e.g., APT activity) on the probe results in a reaction cascade involving (i) cleavage of the thioester to provide a free thiol group, and (ii) an intramolecular Michael addition, wherein the free thiol group reacts with an alkene carbon, thereby forming a seven membered ring. Both the acylated (FIG. 2, top left) and deacylated/cyclized forms (FIG. 2, top right) of the probe have fluorescent properties. However, the fluorescent properties of the different forms can be different. For instance, the two forms can have different excitation and/or emission maxima. Thus, a signal associated with each form of the probe can be detected. Accordingly, the probes of Formulas (Ib) and (IIb) can be used as ratiometric depalmtitoylation probes (RDPs).

In some embodiments, A or A' includes one or more solubility enhancing substituents (e.g., water solubility enhancing substituents). The solubility enhancing substituents can include groups such as, but not limited to, a charged moiety or a moiety that can become charged under physiological conditions or a moiety that can hydrogen bond with water. In some embodiments, A or A' is an aromatic moiety that is substituted with one or more solubility enhancing substituents including, but not limited to, a carboxylate group, a hydroxyl group, an ether, a polyether, a sulfate group, a phosphate group, and an amino group. In some embodiments, the solubility enhancing group is attached to an aromatic core moiety of A or A' (e.g., a fluorophoric or pro-fluorophoric moiety) via a suitable linker, such as an alkenylene, aralkylene or arylene group. In some embodiments, the linker includes a piperazinyl moiety. Thus, in some embodiments, A or A' comprises one or more piperazine-comprising substituent, wherein the piperazine is further substituted with a solubility enhancing moiety, such as a group that comprises a carboxylate. In some embodiments, the piperazinyl-moiety is covalently attached (e.g., via an amide linkage) to a di- or other polycarboxylic acid. In some embodiments, the solubility enhancing moiety is a succinyl-based moiety (e.g., —C(═O)CH₂CH₂C(═O)OH). In some embodiments, A is a residue of a pro-fluorescent rhodol derivative and A has a structure of the formula:

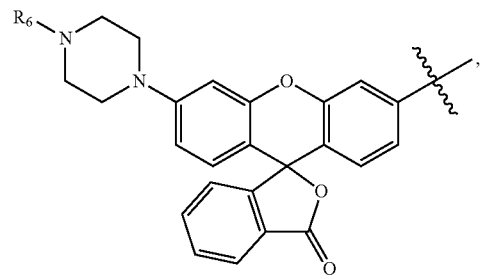

wherein R₆ is —C(═X₁)R₇, wherein X₁ is selected from the group comprising O, N or S, and R₇ is selected from the group comprising H, alkyl, substituted alkyl, aralkyl, substituted aralkyl, aryl, and substituted aryl. In some embodiments, X₁ is O. In some embodiments, R₇ is alkyl (e.g., C₁-C₅ alkyl), or substituted alkyl (e.g., substituted C₁-C₅ alkyl). In some embodiments, R₇ is methyl. In some embodiments, R₇ is carboxylate-substituted C₁-C₅ alkyl group. In some embodiments R₇ is —CH₂CH₂C(═O)OH.

In some embodiments, the compound of Formula (Ia) has a structure of the formula:

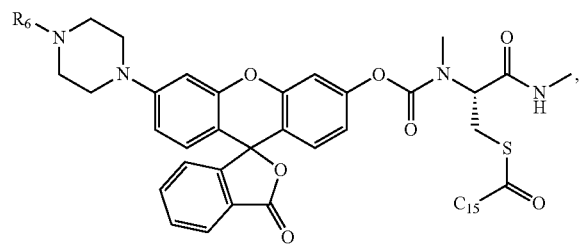

wherein R₆ is as defined above.

In some embodiments, the compound is selected from the group comprising:

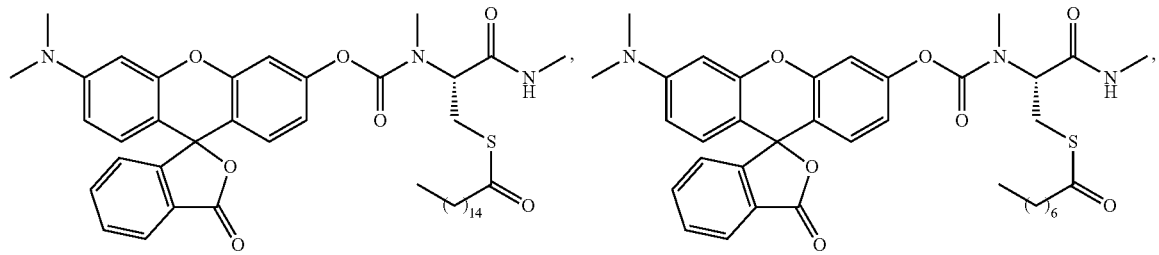

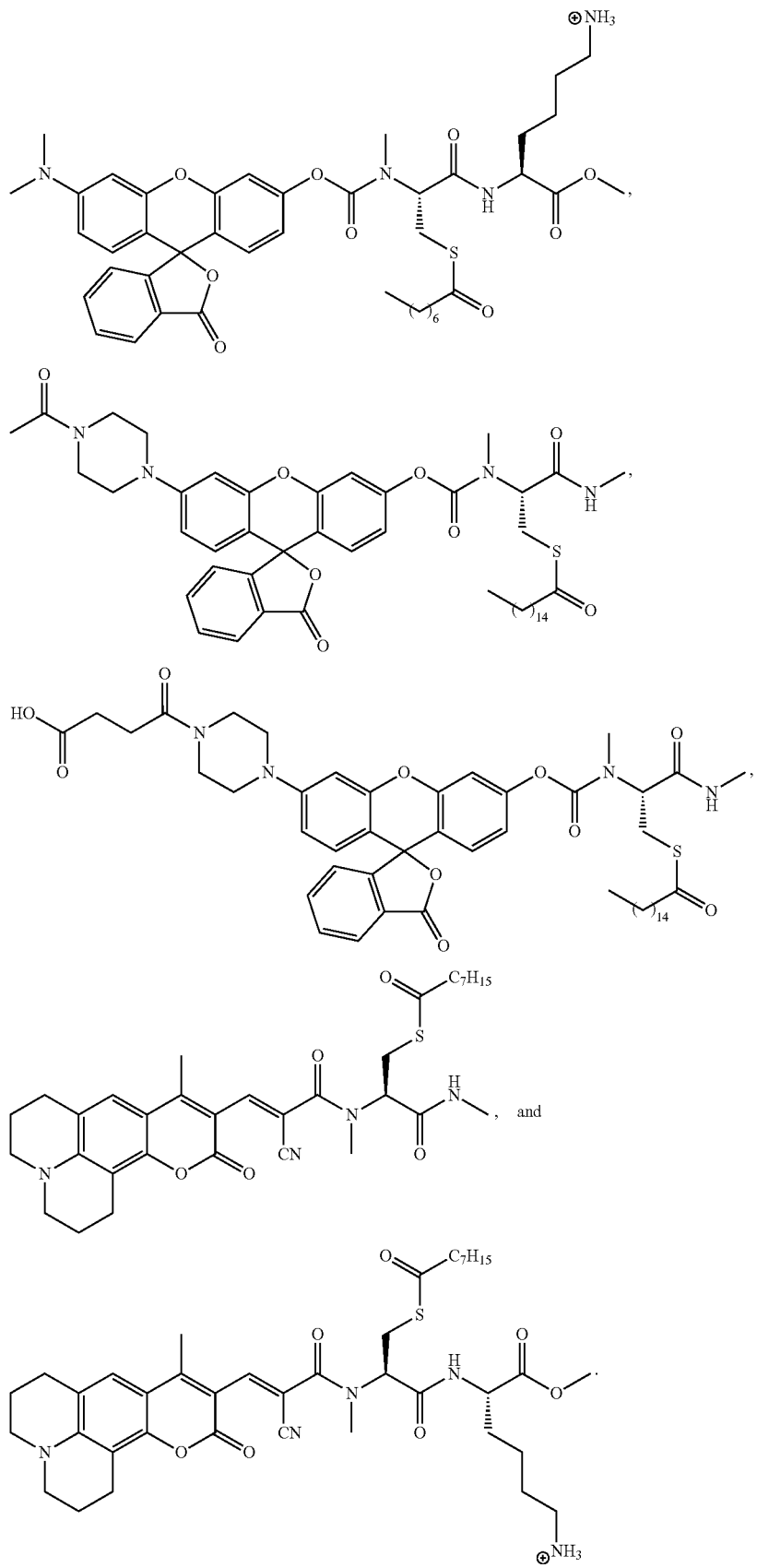

Methods of preparing particular examples of the presently disclosed compounds are described below in the Examples. More generally, the compounds of Formula (Ia) and/or Formula (IIa) can be prepared for example, by preparing an activated form of the compound A-OH, e.g., the parent drug or fluorescent, pro-fluorescent, bioluminescent, or MRI-detectable molecule. In some embodiments, the compound A-OH can be activated via contact with triphosgene or another suitable reagent to form a haloformate (e.g., a chloroformate), which can be reacted with a suitable amine that contains a modified cysteine residue. The reaction can take place in the presence of a base (e.g., triethylamine) and in a non-polar organic solvent, such as, but not limited to tetrahydrofuran (THF). In some embodiments, the amine that contains a modified cysteine residue contains a protected thiol. For example, the thiol can be protected with a trityl group (i.e., a triphenylmethyl group) or another thiol protecting group known in the field of synthetic organic chemistry. The protected thiol can be deprotected to form a free —SH group, which can, in some embodiments, be acylated by reaction with an acid chloride, activated ester, or anhydride to form a thioester. Alternatively, the —SH group can be transformed into another functional group, e.g., a thioether, a S-thiosulfonate, a —S—S—H group, a S—S-glutatione group, a sulfinic acid or sulfinic acid ester, or a S-nitrosothiol group, via chemical transformations known in the art, such as through the use of a suitable coupling reagent or via cysteine oxidation chemistry. In some embodiments, the thiol group can be acylated or otherwise modified and then the carbamate compound can be further modified, e.g., to add or change the group attached to the carboxy group of the modified cysteine residue (i.e., the $NR_1R_2$ of the A' moiety of the compound of Formula (Ia)). In some embodiments, this further modification can be performed using typical chemical reactions used in the preparation of synthetic peptides and/or peptide mimetics.

The compounds of Formula (Ib) and/or Formula (IIb) can be prepared for example, from a benzaldehyde of a compound $A_1$-H, e.g., the parent fluorescent or bioluminescent molecule or a derivative thereof. For example, in some embodiments, benzaldehydes of the formula $A_1$—C(=O)H can be prepared using an electrophilic aromatic substitution reaction, such as a Friedel-Crafts acylation reaction, a Vilsmeier reaction, a Duff reaction, a Gattermann reaction or a Gattermann-Koch reaction. In a Vilsmeier reaction, for instance, an aromatic compound $A_1$-H is reacted with dimethylformamide (DMF) and phosphorus oxychloride ($POCl_3$). However, other methods of forming a benzaldehyde can comprise the oxidation of aromatic methyl groups or benzyl alcohols using a suitable oxidant (e.g., manganese dioxide or pyridinium chlorochromate (PCC)) or the reduction of benzylic acid groups using various reducing agents (e.g., via conversion of the benzylic acid to a benzoyl chloride using thionyl chloride followed by reduction using a Pd catalyst and hydrogen gas). When X is CN, the benzaldehyde can then be reacted with an amino acid or peptidyl residue further comprising a suitably modified cysteine residue and an α-cyano substitutent. This residue can be prepared, for example, by forming an amide bond between the N-terminal amine of an amino acid or peptidyl residue and cyanoacetic acid (e.g., using a carbodiimide coupling reagent). In some embodiments, the modified cysteine residue contains a protected thiol. For example, the thiol can be protected with a trityl group (i.e., a triphenylmethyl group) or another thiol protecting group known in the field of synthetic organic chemistry. The protected thiol can be deprotected to form a free —SH group, which can, in some embodiments, be acylated by reaction with an acid chloride, activated ester, or anhydride to form a thioester. Alternatively, the —SH group can be transformed into another functional group, e.g., a thioether, a S-thiosulfonate, a —S—S—H group, a S—S-glutatione group, a sulfinic acid or sulfinic acid ester, or a S-nitrosothiol group, via chemical transformations known in the art, such as through the use of a suitable coupling reagent or via cysteine oxidation chemistry.

III. Methods of Detecting Enzymatic Activity and Disease

Figure 18:
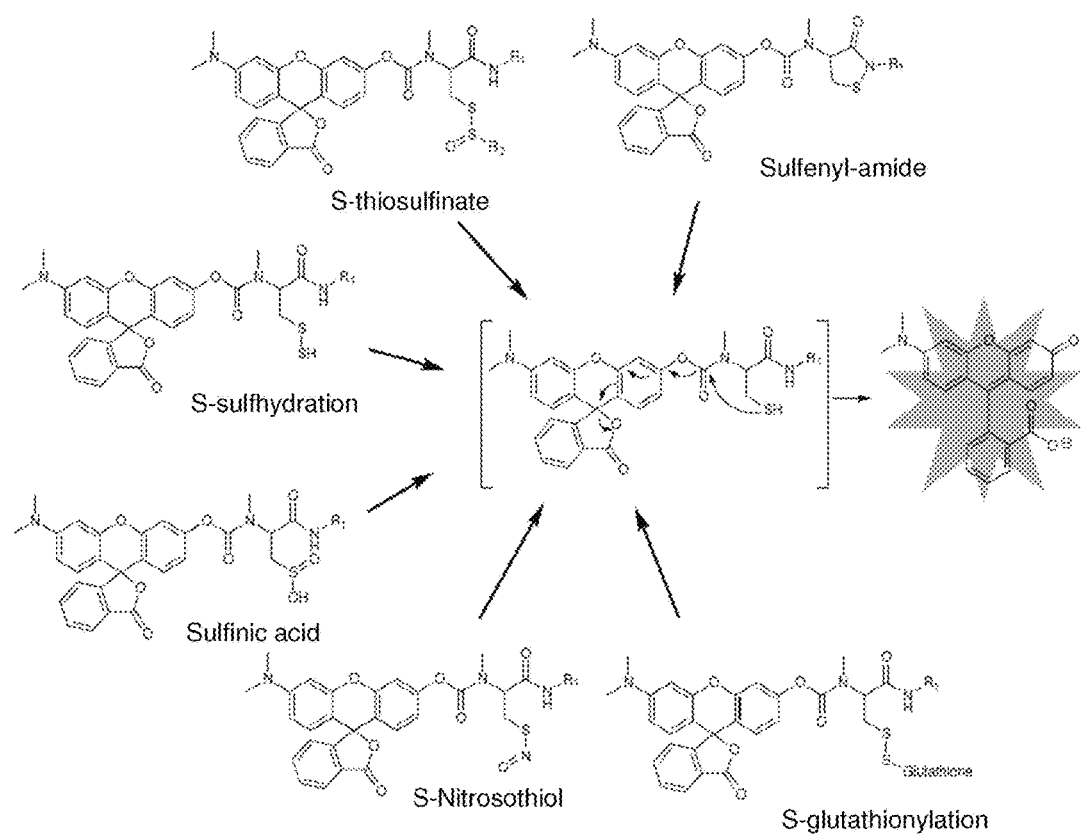
FIG. 18 is a schematic diagram showing the generality of approach to study "erasers" of cysteine post-translational modifications (PTMs) using the presently disclosed probes, including where the PTM is other than S-palmitoylation or formation of another thioester. PTMs that can be studied include S-thiosulfinates, sulfenyl-amides, S-sulfhydration, sulfinic acids, S-glutathionylation, and S-nitrosothiol.

The presently disclosed subject matter provides in some aspects probes for the study of the regulation and biological significance of cysteine PTMs. In some embodiments, the probes can report on and/or respond to endogenous levels of depalmitoylation activity. However, again, the approaches of the presently disclosed subject matter as outlined herein can be immediately deployable to monitor and/or respond to enzymes with activity with respect to a wide variety of other PTMs. See FIG. 18.

As described below in the Examples, in a representative embodiment, a probe, DPP-3, is deployed to discover that growth factor stimulation results in a rapid decrease of depalmitoylation activity in epidermoid carcinoma (A431) cells, uncovering a new mechanism regulating lipid signaling. As also described below in the Examples, in additional representative embodiments, a probe RDP-2 monitors endogenous enzymatic activity in primary tissue samples, while a probe RDP-1 is used to demonstrate that APT activity is linked to lipid metabolism. In yet a further representative embodiment described in the Examples, a probe DPP-5 is used to study changes in S-depamitoylation levels due to lipid stress.

Accordingly, in some embodiments, the presently disclosed subject matter provides a method of detecting enzymatic activity in a sample, the method comprising: contacting the sample with a compound of Formula (Ia) or (Ib):

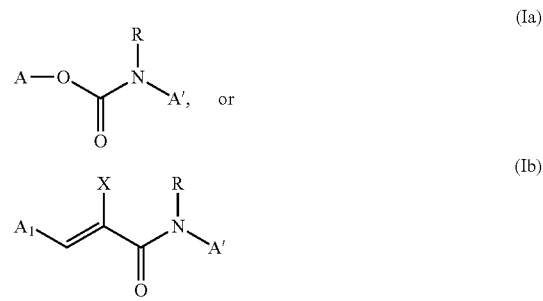

wherein A is an aliphatic or aromatic moiety; $A_1$ is an aromatic moiety; X is H or an electron-withdrawing moiety; R is selected from the group comprising H, alkyl, substituted alkyl, aralkyl, substituted aralkyl, aryl, or substituted aryl; and A' is selected from the group comprising:

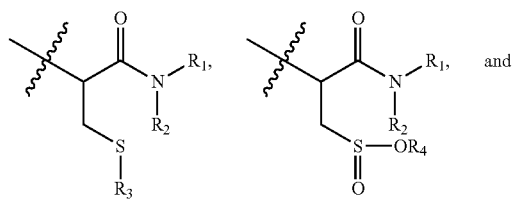

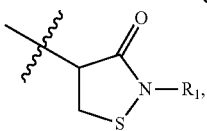

wherein $R_1$ and $R_2$ are each independently selected from the group comprising H, alkyl, substituted alkyl, aralkyl, substituted aralkyl, aryl, substituted aryl; or wherein $R_1$ and $R_2$ together with the nitrogen atom to which they are attached form an amino acid or peptidyl residue; $R_3$ is selected from the group comprising alkyl, substituted alkyl, aralkyl, substituted aralkyl, aryl, substitute aryl, —S(=O)$R_5$, —SH, —N(=O), S-glutathione, and —C(=O)$R_5$; $R_4$ is selected from H and $R_5$; and $R_5$ is selected from the group comprising alkyl, substituted alkyl, aralkyl, and substituted aralkyl; or a pharmaceutically acceptable salt thereof; and detecting a signal in the sample, wherein the presence or amount of the signal is indicative of the presence or amount of enzymatic activity of an enzyme in the sample, further wherein the enzyme is an enzyme that catalyzes a reaction of a modified cysteine substrate.

In some embodiments, A' is

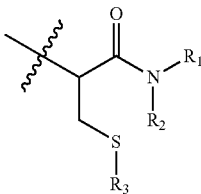

In some embodiments, $R_3$ is an acyl group (i.e., —C(=O)$R_5$), such that the compound of Formula (Ia) or (Ib) is a compound having a structure of Formula (IIa) or (IIb):

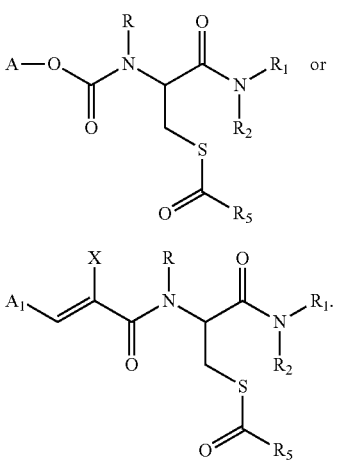

Thus, the compound can comprise an acylated thiol residue. In some embodiments, $R_5$ is —(CH$_2$)$_n$CH$_3$, wherein n is 1-18. In some embodiments, n is 14 so that the $R_5$ group is the same as that in a S-palmitoylated protein. In some embodiments, n is smaller than 14. Thus in some embodiments, n is 1, 2, 3, 4, 5, 6, 7, 8, 9, 10, 11, or 12. In some embodiments, n is 6 or 7.

In some embodiments, R is H or alkyl. For instance, in some embodiments, R is $C_1$-$C_5$ alkyl (e.g., methyl, ethyl, n-propyl, isopropyl, n-butyl, sec-butyl, n-pentyl, iso-pentyl, neo-pentyl, etc.). In some embodiments, R is methyl.

In some embodiments, $R_1$ and $R_2$ are each independently H or alkyl. For instance, in some embodiments, $R_1$ is $C_1$-$C_5$ alkyl (e.g., methyl, ethyl, n-propyl, isopropyl, n-butyl, sec-butyl, n-pentyl, iso-pentyl, neo-pentyl, etc.). In some embodiments, $R_1$ is methyl. In some embodiments, $R_2$ is H.

In some embodiments, $R_1$ and $R_2$ together with the nitrogen atom to which they are attached form an amino acid residue or a peptidyl residue. In some embodiments, the amino acid or peptidyl residue comprises a lysine residue. In some embodiments, $R_1$ and $R_2$ together comprise a peptidyl residue wherein the C-terminal residue (i.e., the residue farthest away from the modified cysteine residue) comprises a positively charged amino acid side chain (e.g., the side chain of a lysine residue). In some embodiments, the amino acid or peptidyl residue comprises a protected carboxylate, e.g., at the C-terminus. In some embodiments, the C-terminal carboxylate is protected as an amide or carbamate.

In some embodiments, X is selected from the group comprising H, CN, NO$_2$, —C(=O)H, keto, and amido. In some embodiments, X is CN.

In some embodiments, A or A' is substituted with one or more solubility enhancing moiety including, but not limited to, a carboxylate group, a hydroxyl group, an ether, a polyether, a sulfate group, a phosphate group, and an amino group. In some embodiments, the solubility enhancing group is attached to an aromatic core moiety of A or A' (e.g., a fluorophoric or pro-fluorophoric moiety) via a suitable linker, such as an alkenylene, aralkylene or arylene group. In some embodiments, the linker includes a piperazinyl moiety. Thus, in some embodiments, A or A' comprises one or more piperazine-comprising substituent, wherein the piperazine is further substituted with a solubility enhancing moiety, such as a group that comprises a carboxylate. In some embodiments, the piperazinyl-moiety is covalently linked (e.g., via an amide linkage) to a dicarboxylic acid or to another polycarboxylic acid. In some embodiments, the solubility enhancing moiety is a succinyl-based moiety (e.g., —C(=O)CH$_2$CH$_2$C(=O)OH). In some embodiments, A is a residue of a rhodol derivative and A has a structure of the formula:

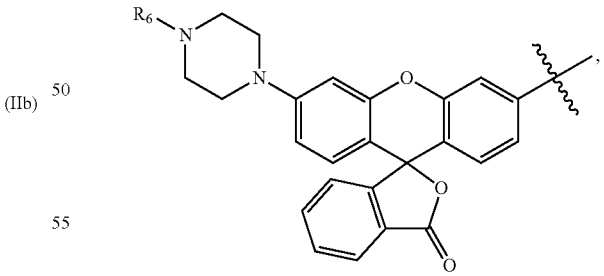

wherein $R_6$ is —C(=$X_1$)$R_7$, wherein $X_1$ is selected from the group comprising O, N or S, and $R_7$ is selected from the group comprising H, alkyl, substituted alkyl, aralkyl, substituted aralkyl, aryl, and substituted aryl. In some embodiments, $X_1$ is O. In some embodiments, $R_7$ is alkyl (e.g., $C_1$-$C_5$ alkyl), or substituted alkyl (e.g., substituted $C_1$-$C_5$ alkyl). In some embodiments, $R_7$ is methyl. In some embodiments, $R_7$ is carboxylate-substituted $C_1$-$C_5$ alkyl. In some embodiments $R_7$ is —CH$_2$CH$_2$C(=O)OH.

In some embodiments, A is a residue of a compound A-OH, wherein A-OH is a pro-fluorescent, fluorescent compound, bio-luminescent, or MRI-detectable moiety, and detecting a signal comprises detecting one or more fluorescence, luminescence, or MRI signals.

In some embodiments, A is a residue of a compound A-OH, wherein A-OH is a pro-fluorescent compound. In some embodiments, $A_1$ is a residue of a compound $A_1$-H, wherein $A_1$-H is a fluorescent compound. In some embodiments, detecting a signal comprises detecting a fluorescence signal (i.e., detecting the fluorescence emission signal from the sample, following illumination of the sample with radiation (e.g., light) of a suitable excitation wavelength). In some embodiments, detecting a signal comprises illuminating the sample or a portion thereof with light at a wavelength at or near the excitation wavelength associated with the fluorophore derived from A-OH and then detecting the fluorescence in the sample at a suitable emission wavelength. In some embodiments, the detecting comprises quantifying the fluorescence and comparing it to the signal obtained from a sample without the compound and/or obtained from a sample derived from a different source (e.g., a different organism, organ, tissue, cell or extract) or from the same source at a different time point.

Since enzymatic action on a compound of Formula (Ia) results in the cleavage of the linkage between the detectable moiety A and the remainder of the probe, in some embodiments, the compounds of Formula (Ia) can be used as "turn-on" probes. However, for compounds of Formula (Ib), compound detection is possible both for the compound as provided (e.g., in its acylated form) and after the compound has been acted upon by the enzyme (e.g., in its deacylated form). Thus, the compounds of Formula (Ib) can act as ratiometric probes. In some embodiments, the use of a ratiometric probe in a heterogenous sample can be particularly useful, as it can help to overcome issues related to unequal probe uptake and distribution that can result in both false negatives and false positives. Accordingly, the use of ratiometric probes can be particularly beneficial for studying dynamic regulation of enzymes during metabolic signaling where samples of interest can include primary samples and/or complex tissues.

In some embodiments, the compound is a compound of Formula (Ib) and detecting a signal in the sample comprises detecting two fluorescence signals, a first fluorescence signal and a second fluorescence signal, wherein the first fluorescence signal is a signal associated with the compound of Formula (Ib) (e.g., the acylated sample), and the second fluorescence signal is a fluorescence signal associated with a compound formed by the cyclization of a thiol product of an enzyme-catalyzed reaction of the compound of Formula (Ib) (e.g., the deacylated signal). In some embodiments, the first fluorescence signal is detected following excitation of the sample at a first wavelength, and the second fluorescence signal is detected following excitation of the sample at a second wavelength and/or wherein the first fluorescence signal and the second fluorescence signals are detected at different emission wavelengths. In some embodiments, a ratiometric signal is provided by dividing the first fluorescence signal by the second fluorescence signal.

In some embodiments, the enzyme is selected from the group comprising a thioesterase, an abhydrolyase domain containing 17A (ABHD17) protein, and a thioetherase. In some embodiments, the enzyme is an acyl protein thioesterase, such as APT1 or APT2.

In some embodiments, the sample is an in vitro sample, such as, but not limited to a sample comprising an isolated enzyme, a cell extract, or a tissue extract. In some embodiments, the sample comprises a live cell or tissue. In some embodiments, the live cell or tissue is selected from the group comprising liver cells or tissue, kidney cells or tissue, breast cells or tissue, skin cells or tissue, brain cells or tissue, cervical cells or tissue, bladder cells or tissue, pancreas cells or tissue, lung cells or tissue, stomach cells or tissue, blood cells or tissue, and colon cells or tissue. In some embodiments, the sample is present in a living organism, e.g., a mammal, optionally a human.

In some embodiments, detecting enzymatic activity in the sample further detects a disease associated with increased or decreased activity of the enzyme. Thus, the method can be used to diagnose a disease, the progress of a disease, or the progress of the treatment of a disease in a subject from which the sample is derived. In some embodiments, the disease can be selected from the group including, but not limited to, cancer, a neurological disorder, a neurodegenerative disorder, a metabolic disorder, diabetes, an autoimmune disease, an infectious disease, a liver disease, a kidney disease, atherosclerosis, and hypertension.

In some embodiments, the presently disclosed subject matter provides a method of detecting a disease associated with increased or decreased activity of an enzyme that catalyzes a reaction of a modified cysteine substrate, the method comprising: contacting the subject or a sample from a subject with a compound of Formula (Ia) or Formula (Ib); and detecting one or more signal, wherein detecting the one or more signal indicates the presence or level of activity of an enzyme associated with a disease. In some embodiments, the one or more signal comprises one or more fluorescence signal.

IV. Pharmaceutically Acceptable Salts and Pharmaceutical Formulations

In some embodiments, the presently disclosed compounds are provided as pharmaceutically acceptable salts or formulations to aid in their administration to various samples of biological origin, e.g., cell extracts, live cells, tissues, organoids, organs, or whole organisms (e.g., animals, such as a mammal, optionally a human) to detect enzymatic activity and/or disease. Additionally, as described above, in some embodiments, the compounds of Formula (Ia) and (Ib) can be used as prodrugs of therapeutically active alcohol or phenol compounds of the formula A-OH. In some embodiments, the compound of formula A-OH is a compound known in the art to have therapeutic biological activity either in vitro and/or in vivo. In some embodiments, the compound of formula A-OH is a compound that has undergone or is undergoing clinical trials to treat a disease associated with an enzyme or enzymes (e.g., APTs) that catalyze reactions of modified cysteine residues. For example, A-OH can be a compound known in the art for the treatment of cancer, a neurological disorder; a neurodegenerative disease; a metabolic disorder (e.g., diabetes); an autoimmune disease; an infectious disease; liver disease; kidney disease; atherosclerosis; or hypertension. When a compound of Formula (Ia) or (IIa) is administered to a subject suffering from such a disease, enzymatic activity can result in cleavage of the carbamate linker and release of the parent compound.

In some embodiments, the subject is a human subject, although it is to be understood that the principles of the presently disclosed subject matter indicate that the presently disclosed subject matter is effective with respect to all vertebrate species, including mammals, which are intended to be included in the terms "subject" and "patient". Moreover, a mammal is understood to include any mammalian species for which employing the compositions and methods disclosed herein is desirable, particularly agricultural and domestic mammalian species.

As such, the methods of the presently disclosed subject matter are particularly useful in warm-blooded vertebrates. Thus, the presently disclosed subject matter concerns mammals and birds. More particularly provided are methods and compositions for mammals such as humans, as well as those mammals of importance due to being endangered (such as Siberian tigers), of economic importance (animals raised on farms for consumption by humans), and/or of social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos or as pets (e.g., parrots), as well as fowl, and more particularly domesticated fowl, for example, poultry, such as turkeys, chickens, ducks, geese, guinea fowl, and the like, as they are also of economic importance to humans. Thus, also provided is the treatment of livestock including, but not limited to domesticated swine (pigs and hogs), ruminants, horses, poultry, and the like.

In some embodiments, the compounds as described herein can be provided and/or administered as a pharmaceutically acceptable salt. Such pharmaceutically acceptable salts include, but are not limited to, gluconate, lactate, acetate, tartarate, citrate, phosphate, borate, nitrate, sulfate, and hydrochloride salts. The salts of the compounds described herein can be prepared, for example, by reacting a base compound with a desired acid in solution. After the reaction is complete, the salts are crystallized from solution by the addition of an appropriate amount of solvent in which the salt is insoluble. In some embodiments, as described in more detail herein below, the hydrochloride salt of a compound is made by passing hydrogen chloride gas into an ethanolic solution of the free base. In some embodiments, the acetate salt can be made by contacting one of the presently disclosed compounds with a solution comprising acetic acid. Accordingly, in some embodiments, the pharmaceutically acceptable salt is a hydrochloride salt. In some embodiments, the pharmaceutically acceptable salt is an acetate salt.

Pharmaceutical formulations comprising the aforementioned prodrug compounds also are provided herein. These pharmaceutical formulations comprise compounds as described herein, in a pharmaceutically acceptable carrier. Pharmaceutical formulations can be prepared for oral, intravenous, or aerosol administration to a subject as discussed in greater detail below. Also, the presently disclosed subject matter provides such compounds that have been lyophilized and that can be reconstituted to form pharmaceutically acceptable formulations for administration, for example, as by intravenous or intramuscular injection.

The therapeutically effective dosage of any particular prodrug compound, the use of which is within the scope of embodiments described herein, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level can restrict intravenous dosages to a lower level, such as up to about 10 mg/kg, with all weights being calculated based on the weight of the active base, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Preferred dosages are 1 µmol/kg to 50 µmol/kg, and more preferably 22 µmol/kg and 33 µmol/kg of the compound for intravenous or oral administration. The duration of the treatment can be varied depending upon the disease being treated or its severity. In some embodiments, the treatment can comprise administration of a prodrug compound one or more times per day for a period of two to three weeks or until the condition is essentially controlled. Lower doses given less frequently can be used prophylactically to prevent or reduce the incidence of recurrence of the disease.

In accordance with the present methods, compounds as described herein can be administered orally as a solid or as a liquid, or can be administered intramuscularly or intravenously as a solution, suspension, or emulsion. Alternatively, the compounds or salts also can be administered by inhalation, intravenously, or intramuscularly as a liposomal suspension. When administered through inhalation the compound or salt can be in the form of a plurality of solid particles or droplets having a particle size from about 0.5 to about 5 microns, and preferably from about 1 to about 2 microns.

Pharmaceutical formulations suitable for intravenous or intramuscular injection are further embodiments provided herein. The pharmaceutical formulations comprise a compound described herein, a prodrug as described herein, or a pharmaceutically acceptable salt thereof, in any pharmaceutically acceptable carrier. If a solution is desired, water is the carrier of choice with respect to water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and typically by filtration through a 0.22-micron filter. Subsequent to sterilization, the solution can be dispensed into appropriate receptacles, such as depyrogenated glass vials. The dispensing is preferably done by an aseptic method. Sterilized closures can then be placed on the vials and, if desired, the vial contents can be lyophilized.

In addition to the presently disclosed compounds, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. The antimicrobial preservative is typically employed when the formulation is placed in a vial designed for multi-dose use. The pharmaceutical formulations described herein can be lyophilized using techniques well known in the art.

In yet another embodiment of the subject matter described herein, there is provided an injectable, stable, sterile formulation comprising a compound or a salt thereof, in a unit dosage form in a sealed container. The compound or salt is provided in the form of a lyophilizate, which is capable of being reconstituted with a suitable pharmaceutically acceptable carrier to form a liquid formulation suitable for injection thereof into a subject. The unit dosage form typically comprises from about 10 mg to about 10 grams of the compound salt.

Other pharmaceutical formulations can be prepared from the water-insoluble compounds disclosed herein, or salts thereof, such as aqueous base emulsions. In such an instance, the formulation will contain a sufficient amount of pharmaceutically acceptable emulsifying agent to emulsify the desired amount of the compound or salt thereof. Particularly useful emulsifying agents include phosphatidyl cholines and lecithin.

Additional embodiments provided herein include liposomal formulations of the compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the compound, the compound can be substantially entrained within the hydrophilic center or core of the liposomes. The lipid layer employed can be of any conventional composition and can either contain cholesterol or can be cholesterol-free. When the compound of interest is relatively water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques.

The liposomal formulations comprising the compounds disclosed herein can be lyophilized to produce a lyophilizate, which can be reconstituted with a pharmaceutically acceptable carrier, such as water, to regenerate a liposomal suspension.

Pharmaceutical formulations also are provided which are suitable for administration as an aerosol by inhalation. These formulations comprise a solution or suspension of a compound of interest described herein or a salt thereof, or a plurality of solid particles of the compound or salt. The desired formulation can be placed in a small chamber and nebulized. Nebulization can be accomplished by compressed air or by ultrasonic energy to form a plurality of liquid droplets or solid particles comprising the compounds or salts. The liquid droplets or solid particles should have a particle size in the range of about 0.5 to about 10 microns, more preferably from about 0.5 to about 5 microns. The solid particles can be obtained by processing the solid compound or a salt thereof, in any appropriate manner known in the art, such as by micronization. Most preferably, the size of the solid particles or droplets will be from about 1 to about 2 microns. In this respect, commercial nebulizers are available to achieve this purpose. The compounds can be administered via an aerosol suspension of respirable particles in a manner set forth in U.S. Pat. No. 5,628,984, the disclosure of which is incorporated herein by reference in its entirety.

When the pharmaceutical formulation suitable for administration as an aerosol is in the form of a liquid, the formulation will comprise a water-soluble active compound in a carrier that comprises water. A surfactant can be present, which lowers the surface tension of the formulation sufficiently to result in the formation of droplets within the desired size range when subjected to nebulization.

As used herein, the term "water-soluble" is meant to define any composition that is soluble in water in an amount of about 50 mg/mL, or greater. Also, as used herein, the term "water-insoluble" is meant to define any composition that has a solubility in water of less than about 20 mg/mL. In some embodiments, water-soluble compounds or salts can be desirable.

V. Methods of Treating Disease

Disclosed in accordance with some embodiments are methods of medical treatment that involve the administration of prodrugs that become active in a cell in the presence of one or particular cellular enzyme(s). The prodrugs are recognized by enzymes that cleave palmitoylated or other modified cysteine residues, thereby releasing the active form of the drug into the cell. Therapeutic indications involving post-translational modifications include, but are not limited to, cancer, neurological disorders, neurodegenerative diseases, diabetes, autoimmune diseases, infectious diseases, liver disease, kidney disease, atherosclerosis, or hypertension. See Howell et al. (2006) *International Review of Cytology* 252, 1-69; Paulsen, C. E. & Carroll, K. S. (2013) *Chem Rev* 113, 4633-4679; Lin et al. (2012) *ACS Chem Biol* 7, 947-960.

Thus, in some embodiments, the presently disclosed subject matter provides a method for treating a disease or condition involving post-translational modification of a cysteine residue in a protein in the subject. The method can comprise providing a subject in need of such treatment; and administering to the subject a prodrug in accordance with the presently disclosed subject matter (i.e., a compound of Formula (Ia) or (IIa). An enzyme that acts on the post transitional modification acts on the prodrug to release the active form of the drug. This approach can provide cell- or tissue-specific delivery of the drug, increased bioavailability of the drug (such as increased solubility) and/or other desirable characteristics.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Materials and Methods for Examples 2-6

General Materials and Methods.

Silica gel P60 (SiliCycle, Inc., Quebec City, Canada; 40-63 µm, 230-400 mesh) was used for column chromatography. Analytical thin layer chromatography was performed using SiliCycle 60 F254 silica gel (SiliCycle, Inc., Quebec City, Canada; precoated sheets, 0.25 mm thick). All chemicals for synthesis were purchased from Sigma-Aldrich (St. Louis, Mo., United States of America) or Fisher Scientific (Pittsburgh, Pa., United States of America) and used as received. ML348 and ML349 were purchased from Tocris (Bristol, United Kingdom). EGF was obtained from Gold Biotechnology (Olivette, Mo., United States of America). Synthesis of N,N-dimethylrhodol was adapted from previous reports. See Sauers et al., Dyes and Pigments, 1987, 8, 35-53; and Smith et al., J. Chem. Soc., Perkins Trans 2, 1993, 1195-1204. $^1$H NMR and $^{13}$C NMR spectra were collected in NMR solvents: CDCl$_3$, CD$_3$OD, or CD$_3$CN (Sigma-Aldrich, St. Louis, Mo., United States of America) at 25° C. using a 500 MHz Bruker Avance II+ spectrometer (Bruker Corporation, Billerica, Mass., United States of America) with 5 mm QNP probe. $^1$H-NMR chemical shifts are reported in parts per million (ppm) relative to the peak of residual proton signals from (CDCl$_3$ 7.26 ppm, CD$_3$OD 3.31 ppm, (CD$_3$)$_2$SO 2.50 ppm or CD$_3$CN 1.94 ppm). Multiplicities are given as: s (singlet), d (doublet), t (triplet), q (quartet), dd (doublet of doublets), m (multiplet). $^{13}$C-NMR chemical shifts are reported in parts per million (ppm) relative to the peak of residual proton signals from (CDCl$_3$ 77.16 ppm, CD$_3$OD 49.0 ppm, (CD$_3$)$_2$SO 39.52 ppm or CD$_3$CN 1.32 and 118.26 ppm). Analysis of NMR was done in iNMR version 5.5.1. and NMR plots were obtained from Topspin 2.1. High resolution mass was obtained from Agilent 6224 TOF High Resolution Accurate Mass Spectrometer (HRA-MS) (Agilent Technologies, Santa Clara, Calif., United States of America) using a combination of atmospheric-pressure chemical ionization (APCI) and electrospray ionization (ESI). Low resolution mass spectral analyses and liquid chromatography analysis were carried out on an Advion Expression-L mass spectrometer (Advion, Ithaca, N.Y., United States of America) coupled with an Agilent 1220 Infinity LC System (Agilent Technologies, Santa Clara, Calif., United States of America). Synthetic procedures and characterization of DPP-1, DPP-2, DPP-3 and their synthetic intermediates described below in Examples 2-4.

Cloning.

All plasmids were constructed by Gibson Assembly from PCR products generated using Q5 Hot Start DNA Polymerase (New England Biolabs, Ipswich, Mass., United States of America) or Phusion Polymerase (homemade). Plasmids containing the genes for APT1 and APT2 were a gift from Anil Mukherjee. The genes for APT1 and APT2 were cloned into a pET-30 expression vector with a His-tag for purification. Catalytically inactivating mutations S119A and S122A were installed into the expression vectors for APT1 and APT2, respectively.

Purification of APT1 and APT2.

The plasmids for overexpression of APT1 or APT2, or their catalytically inactive mutant forms, were transformed into E. coli ROSETTA™ DE3 (MillaporeSigma, Billerica, Mass., United States of America). The cells were cultured in 500 mL lysogeny broth (LB) media with 40 µg/mL of kanamycin in a 1 L flask shaking at 37° C. until OD$_{600}$≈0.6 and then 1 mM isopropy β-D-1 thiogalactopyranoide (IPTG) was added. Cultures were then grown at 18° C. for an additional 20 h. The cells were harvested by centrifugation and lysed by sonication in 30 mL lysis buffer (50 mM NaH$_2$PO$_4$, 300 mM NaCl, 10% glycerol, pH 7.5). Cell debris was discarded after centrifugation and the lysis supernatant was incubated with 2 mL TALON® Metal Affinity Resin (for APT1 and APT2) (Clontech Laboratories, Mountain View, Calif., United States of America) or His60 Ni Superflow Resin (for mutant APT1 and APT2) (Clontech Laboratories, Mountain View, Calif., United States of America) with gentle shaking on ice for 1 h. The His-tagged proteins were purified under standard immobilized metal affinity chromatography (IMAC) by washing and eluting the resin with wash buffer (50 mM NaH$_2$PO$_4$, 300 mM NaCl, 10 mM imidazole 5% glycerol, pH 7.5) and elution buffer (50 mM NaH$_2$PO$_4$, 300 mM NaCl, 50-300 mM imidazole, 5% glycerol, pH 7.5). The purified proteins were then desalted on GE Disposable PD-10 Desalting Columns (GE Healthcare, Little Chalfont, United Kingdom) and stored in the protein storage buffer (50 mM Tris-HCl, pH 7.5, 300 mM NaCl, 1 mM dithiothreitol (DTT), 10% Glycerol) at −80° C. Each purified APT was validated by 12% sodium dodecyl sulfate-polyacrylamide gel electrophoresis (SDS-PAGE) gel for purity. Purified proteins were stored in individual aliquots in protein storage buffer at −80° C. A fresh aliquot of protein was thawed for each experiment.

In Vitro Kinetic Assays and Emission Spectra of DPP-1, DPP-2, and DPP-3.

50 µL of 7.5 µM DPP1-3 in HEPES (20 mM, pH=7.4, 150 mM NaCl, 0.1% Triton X-100) were added to a 384-well black flat bottom plate (Corning Life Sciences, Corning, N.Y., United States of America) and placed in an Infinite M200 Pro (Tecan, Mannedorf, Switzerland) plate reader at 37° C. for 5 min to warm. 25 µL of either 4-(2-hydroxyethyl)-1-piperazineethanesulfonic acid (HEPES) buffer alone or HEPES buffer containing 150 nM APT1 or APT2, was added using a multi-channel pipette, resulting in a final concentration of 5 µM DPP1-3 and 50 nM APT1 or APT2. Fluorescence intensities ($\lambda_{ex}$ 490/9 nm, $\lambda_{em}$ 545/20 nm, Gain 70, No. of flashes 25, Integration time 100 µs and Z-position 20000 µm) were measured at 30 second (s) time intervals for 20 min. At the end of 20 min kinetic run, emission spectra were obtained ($\lambda_{ex}$ 485 nm, A$_{em}$510-700 nm, Gain 100, No. of flashes 25, Integration time 100 µs and Z-position 20,000 µm). For the catalytically inactive enzyme experiments, 10 times more APT1(S119A) and APT2(S122A) enzyme were used.

In Vitro Inhibitor Assays of DPP-3.

20 µL of 300 nM APT1/APT2 in HEPES (20 mM, pH=7.4, 150 mM NaCl, 0.1% Triton-X 100) were added to 20 µL of buffer/300 µM PalmB/300 µM ML348 and incubated at 37° C. for 30 min. Similarly, for the no APT control, 20 µL buffer was added to 20 µL of buffer containing 0.3% DMSO. 25 µL of the mixture was added to the 50 µL of 7.5 µM DPP-3 in HEPES buffer for a final concentration of 50 µM PalmB/ML348, 50 nM APT1/2, and 5 µM of DPP-3. After incubation for 20 min at 37° C., 60 µL of each mixture was transferred to a 384-well black flat bottom plate. Fluorescence intensities ($\lambda_{ex}$ 490/9 nm, $\lambda_{em}$ 545/20 nm, Gain 70, No. of flashes 25, Integration time 100 µs and Z-position 20,000 µm) were then measured after 10 min.

UV-Vis.

UV-Vis measurements were carried out on a Shimadzu UV-2700 UV-VIS spectrophotometer (Shimadzu Scientific Instruments, Columbia, Md., United States of America). Samples for absorption measurements were contained in 1 cm×1 cm quartz cuvettes with 1 cm light path (Hellma analytics). HEPES (20 mM, pH=7.4, 150 mM NaCl) containing 1% Triton X-100 was used to make dilute solution of DPP1, DPP2, and DPP3 of 1.0-0.1 absorbance at 310 nm. Extinction coefficients were calculated by linear least-squares fitting of plots of A vs. concentration. All fits gave R$^2$ values of >0.999.

Cell Culture and Maintenance.

HEK293T and HeLa cells (American Type Culture Collection (ATCC), Manassas, Va., United States of America), A431 cells (gift from Yamuna Krishnan), MDA-MB-231 and MCF-7 cells (gift from Cellular Screening Center, University of Chicago) were maintained in DMEM/High Glucose (10% FBS, 1% P/S, L-Glutamine, Sodium pyruvate, Gibco/Life Technologies, Gaithersburg, Md., United States of America) with 10% FBS (Gibco/Life Technologies, Gaithersburg, Md., United States of America; Qualified US origin) at 37° C. and 5% CO$_2$. HEK293T, MDA-MB-231, and MCF-7 cells are listed in the online database of commonly misidentified cell lines maintained by the International Cell Line Authentication Committee (ICLAC). Fresh cells or early passage aliquots were obtained, which were frozen down at an early passage (passage 5) in individual aliquots. The cells were then used for less than 25 passages for all experiments. Multiple biological replicates were performed with cells from different passages and freshly thawed aliquots. There was no testing for *mycoplasma* infection or further authentification because early passage cells were used for all experiments.

Fluorescence Imaging of DPP-2 and DPP-3.

HEK293T (650,000 cells per dish) cells were plated with 1.5 mL of Dulbecco's Modified Eagle Medium (DMEM) (High Glucose, 10% fetal bovine serum (FBS)) in a 35 mm glass bottom dish (D35-10-1.5-N; Cellvis, Mountain View, Calif., United States of America) 24 hrs prior to imaging. 30 min before the addition of the DPP probe, the cell culture media was removed and cells were washed with 1 mL of Delbecco's phosphate-buffered saline (DPBS). The media was then replaced with 1 mL of DMEM containing 1 µM Hoechst 33342 and either 0.1% DMSO carrier as a control, 1 or 2 µM Palm B, 0.1, 1.0, or 5 µM ML348, and incubated for 30 min at 37° C. and 5% $CO_2$. The media was removed, the cells were washed with 1 mL of Live Cell Imaging Solution (Thermo Fisher Scientific, Waltham, Mass., United States of America), and 1 mL of 1 µM DPP-2 or DPP-3 in Live Cell Imaging Solution was added to each plate. For ML348 0.1, 1.0, or 5 µM was added along with DPP-2 or DPP-3. After incubation for 15 min at 37° C. and 5% $CO_2$, images were obtained on an inverted epi-fluorescence microscope (Olympus IX83; Olympus Corporation, Tokyo, Japan) attached with EMCCD camera (Photometrics EVOLVE™ Delta; Photometrics, Tucson, Ariz., United States of America) with 40× oil objective (N/A 1.3) for DPP-2 (excitation filter 500/20, dichroic chroma 89007, emission filter 535/30, exposure time 200 ms, EM gain 25), Hoechst 33342: (excitation filter 402/15, emission filter 455/50, dichroic chroma 89013, exposure time 30 ms, EM gain 25), and brightfield (exposure time 5 ms, EM gain 5), and for DPP-3 (exposure time 500 ms, EM gain 150), Hoechst 33342: (exposure time 30 ms, EM gain 25), and brightfield (exposure time 20 ms, EM gain 5). Analyses were performed in ImageJ. For data analysis, the average fluorescence intensity per image in each experimental condition was obtained by selecting regions of interest (ROIs) in the brightfield image. For display, the data were normalized to the average fluorescence intensity of the control conditions. Each experiment was repeated at least three separate times with identical results.

Flow Cytometry.

Cells were plated on a 10 cm dish with 10 mL of DMEM/High Glucose (10% FBS, 1% P/S, L-Glutamine, Sodium pyruvate) 36-48 hours prior to the day of experiment and maintained at 37° C., 5% $CO_2$ so as to obtain 80-90% confluency. Cells were washed with DPBS and trypsinized with 1 mL 0.05% Trypsin. 5 mL of DMEM/High Glucose (10% FBS, L-Glutamine, Sodium pyruvate) was added and cells were spun down at 1200 rpm for 3 min. Media was discarded and cells were resuspended in 5 mL of Live Cell Imaging Solution and again spun down at 1200 rpm for 3 min. The cells pellets obtained were resuspended in 3-5 mL of Live Cell Imaging Solution and divided into 500 µL aliquots. The aliquots were treated with either 0.2% DMSO carrier or 1 µM of PalmB/ML348 or 1 µM/5 µM of ML349 inhibitor. After 30 min of incubation at room temperature, 1 µL of 2.5 mM DPP-3 in DMSO was added to each aliquot for a final concentration of 5 µM, and the solutions were mixed. After 5 min incubation at room temperature, fluorescence signal in FITC channel was measured for 10000 cells (5000 for HeLa experiments) on a LSR-Fortessa 4-15 HTS (BD digital instrument, 488 nm laser with 530/30 nm filter for FITC; BD, Franklin Lakes, N.J., United States of America). For analyzing DPP2 in HEK293T cells, the aliquots were treated with either 0.2% DMSO carrier or 2 µM of PalmB, 5 or 20 µM of ML348/ML349 and then analyzed by the protocol as mentioned above. Data was analyzed by FlowJo software version 10.0.8. For comparison of A431 starved versus non-starved, parallel 10 cm dishes of A431 cells were plated in 10 mL of DMEM (high glucose, 10% FBS, 1% P/S), and grown for 36 h. The growth media was removed, and replaced by 10 mL of either DMEM (High glucose) with 10% FBS to maintain "growth" conditions, or DMEM (High glucose) without FBS respectively for "starvation" conditions, and incubated for 14 h. After trypsinization, both plates were treated with 5 mL of DMEM (high glucose) for spinning the cells down, and further processing and analysis were performed as described above by flow cytometry.

APT1 RNAi by Fluorescence Microsopy.

30,000 cells per well were plated in 250 µL DMEM glutamax (high glucose, 10% FBS) in an 8-well imaging dish (Lab-Tek Chambered Coverglass, Thermo Fisher Scientific, Waltham, Mass., United States of America). After 12 h, the cells were transfected with 5 pmol control/APT1 siRNA using Lipofectamine RNAi Max (Thermo Fisher Scientific, Waltham, Mass., United States of America) using the standard protocol. After 48 h the media was replaced by 1 µM Hoechst 33342 in 300 µL DMEM, high glucose. After 15 min of incubation at 37° C., the cells were washed with 1 mL of Live Cell Imaging Solution and replaced by 5 µM DPP3 in Live Cell Imaging Solution. After 15 min of incubation at room temperature, images were obtained on an inverted epi-fluorescence microscope (Olympus IX83; Olympus Corporation, Tokyo, Japan) attached with EMCCD camera (Photometrics EVOLVE™ Delta; Photometrics, Tucson, Ariz., United States of America) with 40× oil objective (N/A 1.3) for DPP-3 (excitation filter 500/20, dichroic chroma 89007, emission filter 535/30, exposure time 100 ms, EM gain 50), Hoechst 33342: (excitation filter 402/15, emission filter 455/50, dichroic chroma 89013, exposure time 40 ms, EM gain 30), and brightfield (exposure time 30 ms, EM gain 10). Analyses were performed in ImageJ. For data analysis, the average fluorescence intensity per image in each experimental condition was obtained by selecting ROIs in the brightfield image, and the data was normalized to the average fluorescence intensity of the control siRNA conditions. The experiment was repeated in three biological replicates.

APT1 RNAi by Flow Cytometry.

350,000 cells per well were plated in 2 mL DMEM glutamax (high glucose, 10% FBS) in a 6-well dish. After 12 h, the cells were transfected with 30 pmol control/APT1 siRNA using Lipofectamine RNAi Max (Thermo Fisher Scientific, Waltham, Mass., United States of America) using the standard protocol. After 48 h the media was removed, the cells were washed with 1.5 mL of DPBS, and removed from the plate by incubation with 200 µL of 0.05% trypsin. The cells were resuspended in 1.2 mL DMEM glutamax (high glucose, 10% FBS) and centrifuged at 500 rcf for 3 min. The supernatant was discarded, the cells were washed twice with 1 mL of Live Cell Imaging Solution, and the cell pellet was then resuspended in Live Cell Imaging Solution to generate 500 µL aliquots. 1 µL of 2.5 mM DPP-3 in DMSO was added to each aliquot for a final concentration of 5 µM. After 5 min incubation at room temperature, fluorescence signal in the FITC channel was measured for 10,000 cells on a LSR-Fortessa 4-15 HTS (BD digital instrument, 488 nm laser with 530/30 nm filter for FITC; BD, Franklin Lakes, N.J., United States of America). Data was analyzed by FlowJo software version 10.0.8.

Starvation and EGF Stimulation of A431 Cells.

Parallel 35 mm glass bottom dishes (D35-10-1.5-N; Cellvis, Mountain View, Calif., United States of America) of A431 cells (450,000) were plated in 2 mL of DMEM glutamax (high glucose, 10% FBS, 1% P/S), and grown for 36 h. The growth media was removed, and replaced by 1.5 mL of either DMEM (High glucose) with 10% FBS to maintain "growth" conditions, or DMEM (High glucose) without FBS respectively for "starvation" conditions, and incubated for 24 h. The media was replaced by 1 mL of "growth" or "starvation" media containing 1 μM Hoechst 33342. After incubation for 15 min at 37° C., the media from both the serum starved or full serum dishes was removed, and the cells were washed with 1 mL Live cell imaging solution. 1 mL Live Cell Imaging Solution containing 5 μM DPP-3 was then added and the dish was incubated at room temperature for 15 minutes. For EGF stimulation experiments, two parallel dishes of cells were serum starved, then incubated with DPP-3 in either the absence or the presence of 1 ng/mL EGF. The cells were then imaged for DPP-3 (excitation filter 500/20, dichroic chroma 89007, emission filter 535/30, exposure time 150 ms, EM gain 50), Hoechst 33342: (excitation filter 402/15, emission filter 455/50, dichroic chroma 89013, exposure time 25 ms, EM gain 30), and brightfield (exposure time 20 ms, EM gain 10 for starvation experiment or exposure time 5 ms, EM gain 5 for EGF stimulation experiment). For data analysis, the average fluorescence intensity per image in each experimental condition was obtained by selecting ROIs in the brightfield image. For display, the data were normalized to the average fluorescence intensity of the control conditions. For the starvation experiments, the non-starved cells were used as the control conditions and arbitrarily set to '100', while for the EGF stimulation experiments the starved, no EGF cells were used as the reference control. Each separate experiment was repeated at least three times. The data from each biological replicate for the EGF stimulation was analyzed individually. The average results from the three biological replicate experiments for both experiments were analyzed in batch.

Example 2

Synthesis of DPP-1

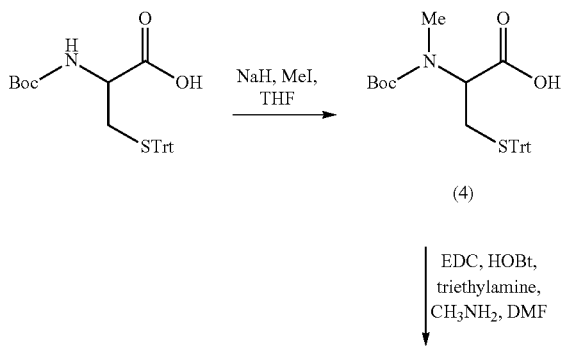

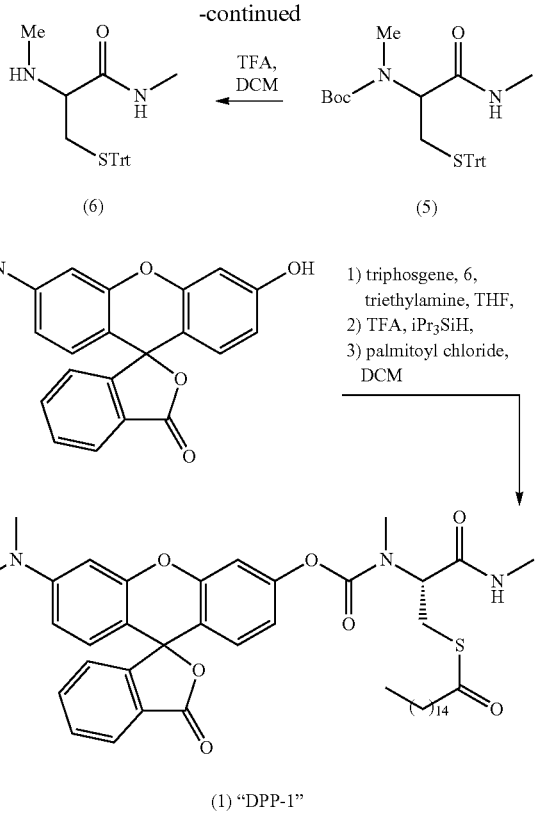

DPP-1 (or 1) was prepared as shown above in Scheme 1. First, compound 4 was prepared via a reaction adapted from Vippila et al. (2015) J Nat Prod 78, 2398-2404. To a suspension of NaH (60% in oil, 1.837 g, 45.93 mmol, 3.0 eq) in dry tetrahydrofuran (THF) (21 mL) at 0° C. and under $N_2$, a solution of Boc-Cys(Trt)-OH (7.014 g, 15.13 mmol, 1.0 eq) in 35 mL dry THF was added dropwise. The reaction mixture was stirred for 10 min, followed by the addition of MeI (3.8 mL, 61.0 mmol, 4.0 eq). The ice bath was removed and reaction mixture was stirred at room temperature for 20 h. The reaction mixture was diluted with 100 mL of EtOAc and washed with $H_2O$ (pH-2). The aqueous layer was again washed with 100 mL of EtOAc, and the combined organic layer was dried over $Na_2SO_4$ and evaporated to give a crude product, which was then purified by column chromatography (Silica gel; 3-7% methanol (MeOH): dichloromethane (DCM)) to give 4 (3.5774 g, 49% isolated yield). $R_f$: 0.26 (silica gel TLC; 5% MeOH:DCM). HRA-MS(+): Calculated for $C_{28}H_{31}NO_4S$ [M$^+$]477.1974, found 477.1970. NMR characterization was not completed due to a lack of solubility in any common NMR solvent.

A solution of 4 (0.600 g; 1.256 mmol; 1.0 eq), EDC.HCl (0.362 g, 1.888 mmol, 1.5 eq.), HOBt (80%, 0.320 g, 2.360 mmol, 1.5 eq), $CH_3NH_2$—HCl (93.4 mg, 1.383 mmol, 1.1 eq) and trimethylamine (177.0 μL, 1.270 mmol, 1.0 eq) in 3 mL dry DMF was stirred at room temperature for 30 min. The reaction mixture was diluted with 30 mL of DCM and washed with $H_2O$ (pH~3). The aqueous layer was washed again with 20 mL DCM and the combined organic layer was dried with $Na_2SO_4$, filtered, evaporated to give a crude product, and purified by column chromatography (Silica gel; 5-15% EtOAc:DCM) to give 5 (512.4 mg, 83% yield). $R_f$: 0.41 (silica gel TLC; 10% EtOAc:DCM). HRA-MS(+): Calculated for $C_{29}H_{34}N_2O_3S$ [M$^+$] 490.2290; found 490.2277 (70V). ¹H-NMR (500 MHz; CD₃CN), δ: 7.40 (d, J=7.4 Hz, 6H), 7.32 (t, J=7.6 Hz, 6H), 7.24 (t, J=7.3 Hz, 3H), 6.44 (s, 1H), 4.30 (dd, J=150.5, 5.3 Hz, 1H), 2.71 (s, 1H), 2.61-2.54 (m, 5H), 2.24 (s, 2H), 1.44 and 1.39 (s, 9H). ¹³C-NMR (126 MHz; CD₃CN, Rotamers), δ: 170.6, 145.7, 130.3, 129.0, 127.8, 81.0, 80.8, 67.3, 60.8, 58.7, 32.6, 32.4, 31.7, 31.3, 28.5, 26.2.

A solution of 5 (491.9 mg; 1.0 mmol; 1 eq) in 3 mL of 20% trifluoroacetic acid (TFA):DCM was stirred at room temperature under nitrogen for 25 min. The reaction mixture was diluted with 25 mL of DCM followed by rotatory evaporation at 35° C. The crude product was then purified by column chromatography (Silica gel; 0-10% MeOH in 1:1 EtOAc:DCM) to afford 6 (0.3717 g; 95% yield). $R_f$: 0.5 (silica gel TLC; 10% MeOH in 1:1 EtOAc:DCM). HRA-MS(+): Calculated for $C_{24}H_{26}N_2OS$ [M⁺] 390.1766; found 390.1764. ¹H-NMR (500 MHz; CD₃CN), δ: 7.40-7.38 (m, 6H), 7.36-7.32 (m, 6H), 7.29-7.26 (m, 3H), 7.05 (s, 1H), 3.19 (dd, J=7.2, 5.3 Hz, 2H), 2.70 (q, J=6.3 Hz, 4H), 2.58 (dd, J=13.0, 5.2 Hz, 1H), 2.32 (s, 3H). ¹³C-NMR (126 MHz; CDCl₃, Rotamers), δ: 171.4, 167.6, 162.2, 162.0, 143.9, 129.5, 128.2, 127.2, 117.6, 115.3, 67.6, 60.5, 60.3, 31.0, 30.3, 26.3, 21.0, 14.2.

To a solution of triphosgene (0.148 g; 0.499 mmol; 1 eq) in dry THF (5 mL) at 0° C., a solution of rhodol (0.1744 g; 0.485 mmol; 1 eq) with triethyl amine (0.59 mL; 0.844 M in THF; 1 eq) in dry THF (10 mL) was added dropwise over 20 m. The ice bath was then replaced by a 40° C. water bath, and nitrogen was flushed through to evaporate the THF. Dry THF (5 mL) was freshly added to the reaction mixture followed by dropwise addition of 3 mL THF solution of 6 (132.9 mg; 0.340 mmol; 0.7 eq), followed by the addition of triethyl amine (0.4 mL; 0.844 M sol in THF, 0.7 eq). The reaction mixture was evaporated and the crude product was dissolved in DCM (5 mL). Triisopropyl silane (348 μL; 5 eq to amine) and TFA (2.1 mL) was added to the solution and stirred room temperature. After 5 m, the reaction mixture was diluted with 20 mL DCM and evaporated by rotary evaporation. 4 mL of palmitoyl chloride and 1 mL of DCM was added to the dried crude product and the reaction mixture was stirred for 30 m at room temperature. The reaction mixture was diluted with 30 mL DCM and washed with 30 mL H₂O (pH~8). The aqueous layer was further washed with DCM (20 mL). The combined organic layers were dried over Na₂SO₄ and evaporated by rotary evaporation. The crude product was purified by successive column chromatography steps (Silica gel; a. 10-100% EtOAc:DCM, b. 1-5% MeOH:DCM, c. 30-70% EtOAc:Hexane) to afford DPP-1 (71.3 mg; 27% yield). $R_f$: 0.24 (silica gel TLC; 1:1 EtOAc:Hexane). HRA-MS(+): Calculated for $C_{44}H_{57}N_3O_7S$ [M⁺] 771.3917; found 771.3926. ¹H-NMR (500 MHz; CDCl₃), δ: 8.00 (d, J=7.5 Hz, 1H), 7.66-7.58 (m, 2H), 7.14 (d, J=7.4 Hz, 1H), 7.08 (dd, J=5.8, 3.9 Hz, 1H), 6.78-6.75 (m, 2H), 6.60 (d, J=8.8 Hz, 1H), 6.46-6.39 (m, 2H), 4.79-4.69 (m, 1H), 3.57-3.43 (m, 1H), 3.33-3.26 (m, 1H), 3.02 (s, 2H), 2.97 (s, 6H), 2.92 (s, 1H), 2.83 (d, J=4.9 Hz, 1H), 2.77 (d, J=2.9 Hz, 2H), 2.55 (q, J=7.7 Hz, 2H), 1.63 (m, 2H), 1.23 (m, 25H), 0.87 (t, J=6.9 Hz, 3H). ¹³C-NMR (126 MHz; CDCl₃), δ: 198.8, 169.7, 169.3, 155.3, 153.2, 152.4, 152.3, 152.3, 152.2, 135.0, 129.7, 129.0, 128.7, 126.9, 125.0, 124.1, 117.0, 116.9, 110.3, 110.3, 109.2, 105.9, 98.5, 83.5, 59.6, 58.7, 44.2, 40.3, 32.0, 31.7, 31.1, 31.1, 29.8, 29.8, 29.8, 29.7, 29.7, 29.7, 29.5, 29.5, 29.3, 29.0, 27.3, 26.4, 26.3, 25.7, 25.7, 22.8, 14.2.

Example 3

Synthesis of DPP-2

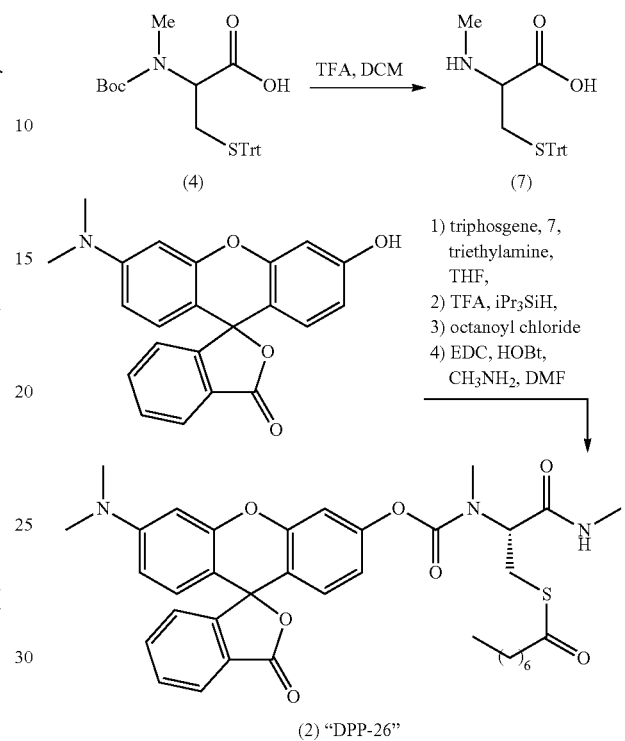

Scheme 2. Synthesis of DPP-2 (2).

DPP-2 (or 2) was synthesized as shown in Scheme 2, above. First, a solution of 4 (1.24 g; 2.596 mmol; 1 eq) in 10 mL of 20% TFA:DCM was stirred at room temperature under nitrogen for 25 min. The reaction mixture was diluted with 20 mL DCM followed by rotatory evaporation at 35° C. The crude product was purified by column chromatography (Silica gel; 5-40% MeOH:DCM) to afford 7 (887.4 mg; 90% yield). $R_f$: 0.33 (silica gel TLC; 15% MeOH:DCM). HRA-MS(+): Calculated for $C_{23}H_{23}NO_2S$ [M⁺] 377.1449; found 377.1440. ¹H-NMR (500 MHz; (CD₃)₂SO), δ: 7.33-7.29 (m, 12H), 7.22 (m, 3H), 3.19 (t, J=5.8 Hz, 1H), 3.14 (s, 1H), 2.85 (s, 1H), 2.70 (s, 1H), 2.26 (s, 3H). ¹³C-NMR (126 MHz; (CD₃)₂SO, Rotamers), δ: 168.3, 162.4, 144.0, 129.2, 128.2, 126.9, 66.3, 60.7, 48.6, 35.8, 31.7, 31.2, 30.8.

To a solution of triphosgene (0.132 g; 0.445 mmol; 1 eq) in dry THF (5 mL) at 0° C. was added a solution of rhodol (0.157 g; 0.437 mmol; 1 eq) with triethyl amine (0.42 mL; 1.055 M sol in THF, 1 eq) in dry THF (10 mL) dropwise over 20 min. The ice bath was replaced by a 40° C. water bath and nitrogen was flushed over the solution until the THF evaporated. Dry THF (5 mL) was added to the reaction mixture followed by dropwise addition of 4 mL THF solution of 7 (115.7 mg; 0.307 mmol; 0.7 eq) and triethyl amine (0.29 mL; 1.055 M sol in THF, 0.7 eq). The reaction mixture was evaporated and the crude was redissolved in DCM (5 mL). Triisopropyl silane (313 μL; 5 eq to amine) and TFA (2.1 mL) was added and the mixture was stirred at room temperature. After 5 min, the reaction mixture was diluted with 20 mL DCM and evaporated by rotary evaporation. 3 mL of octanoyl chloride was then added to the crude product and reaction mixture was stirred for 30 min at room temperature. The reaction mixture was diluted with 30 mL of DCM and washed with 30 mL H₂O (pH~8). The aqueous layer was further washed with DCM (20 mL). The combined organic layers were dried over Na₂SO₄ and evaporated by rotary evaporation. Purification by column chromatography (Silica gel; 5-25% MeOH:DCM) gave the carboxylic acid product (120.2 mg) as a mixture (45%; analyzed by LCMS). To this mixture in DMF (1 mL), EDC.HCl (35.7 mg), HOBt (80%; 34.5 mg), methylamine hydrochloride (12.7 mg) and triethylamine (0.27 mL; 0.342 M in DMF) was added. After 10 min, the reaction was diluted with 30 mL DCM and washed with $H_2O$ (20 mL; pH-3). The organic layer was collected, dried with $Na_2SO_4$ and evaporated by rotary evaporation. The crude was purified by successive column chromatography (Silica gel; a. 10-40% EtOAc:DCM, b. 2% MeOH:DCM, c. 30-65% EtOAc:Hexane) to afford DPP-2 (49.9 mg, 25% yield). $R_f$: 0.23 (silica gel TLC; 1:1 EtOAc:Hexane). HRA-MS(+): Calculated for $C_{36}H_{41}N_3O_7S$ [M+] 659.2665; found 659.2675. $^1$H-NMR (500 MHz; $CDCl_3$), δ: 8.01 (d, J=7.5 Hz, 1H), 7.67-7.59 (m, 2H), 7.16 (d, J=7.5 Hz, 1H), 7.09 (t, J=2.2 Hz, 1H), 6.78 (m, 2H), 6.61 (d, J=8.8 Hz, 1H), 6.48 (d, J=2.5 Hz, 1H), 6.42 (dd, J=8.9, 2.5 Hz, 1H), 4.81-4.69 (m, 1H), 3.58-3.47 (m, 1H), 3.31 (m, 1H), 3.04 (s, 2H), 2.99 (s, 6H), 2.94 (s, 1H), 2.89 (t, J=4.6 Hz, 1H), 2.82 (t, J=4.7 Hz, 2H), 2.56 (q, J=7.7 Hz, 2H), 1.66-1.62 (m, 2H), 1.29-1.24 (m, 9H), 0.84 (t, J=5.9 Hz, 3H). $^{13}$C-NMR (126 MHz; $CDCl_3$), δ: 198.8, 169.7, 169.4, 169.1, 155.4, 153.2, 152.5, 152.3, 152.3, 152.3, 135.0, 129.7, 129.0, 128.7, 127.0, 125.1, 124.1, 117.0, 117.0, 110.3, 110.3, 109.2, 105.9, 98.5, 83.5, 58.7, 58.7, 44.2, 44.2, 40.3, 31.7, 31.7, 31.1, 31.1, 29.0, 27.3, 26.4, 25.7, 25.5, 22.7, 14.2.

Example 4

Synthesis of DPP-3

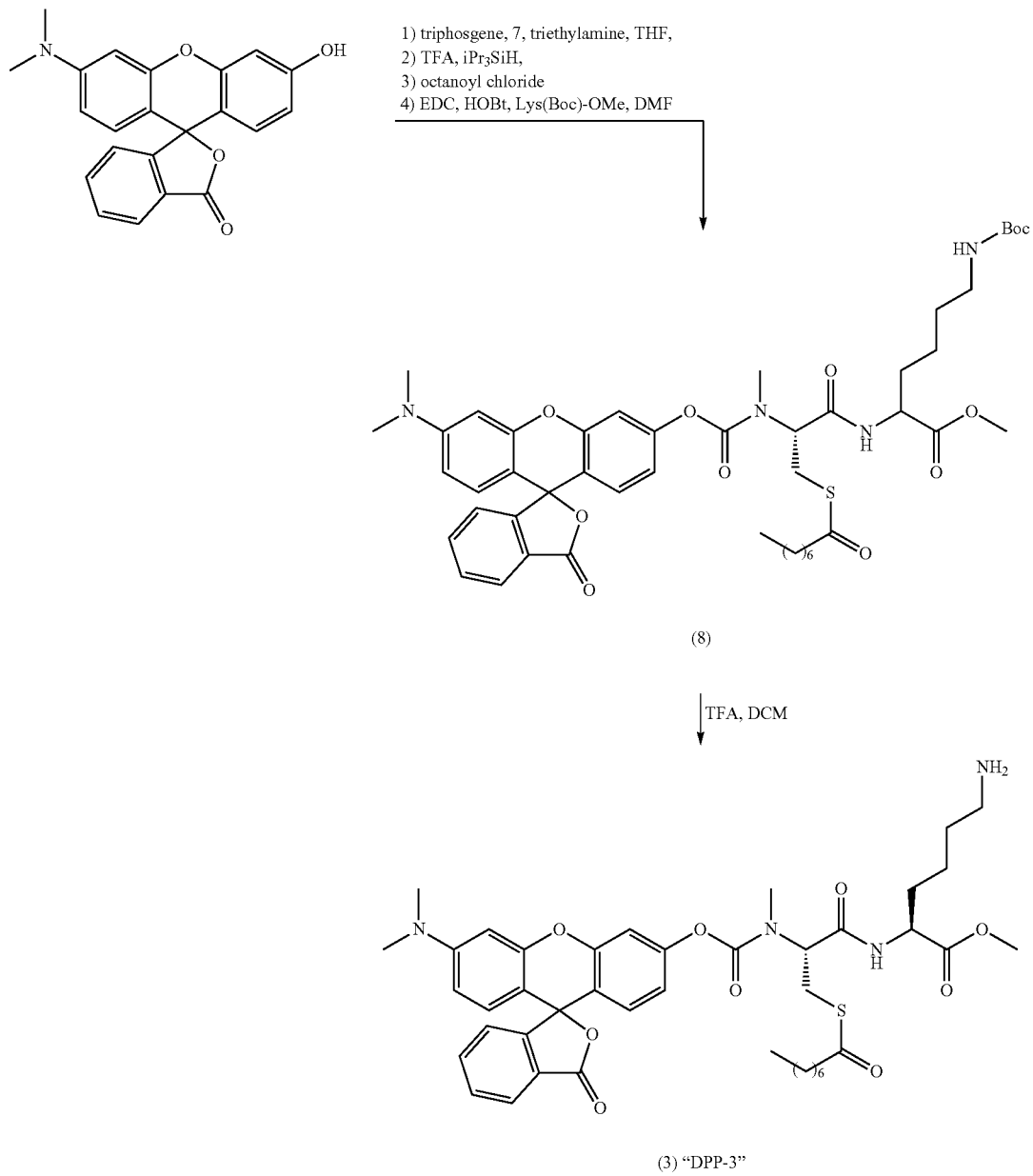

DPP-3 (or 3) was synthesized as shown above in Scheme 3. First, to a solution of triphosgene (173.4 mg; 0.584 mmol; 1 eq) in dry THF (7 mL) at 0° C., a solution of rhodol (209.0 mg; 0.582 mmol; 1 eq) with triethyl amine (0.7 mL; 0.844 M sol in THF, 1 eq) in dry THF (15 mL) was added dropwise over 20 min. The ice bath was replaced by a 40° C. water bath and nitrogen was flushed over the solution to evaporate the. Dry THF (10 mL) was added to the mixture followed by dropwise addition of 5.3 mL THF solution of 7 (153.7 mg; 0.407 mmol; 0.7 eq) and triethyl amine (0.49 mL; 0.844 M sol in THF, 0.7 eq). The reaction mixture was evaporated by rotary evaporation and the crude product was dissolved in DCM (5 mL). To this solution, triisopropyl silane (416 μL; 5 eq to amine) and TFA (2.1 mL) was added and the reaction stirred at room temperature. After 5 min the reaction mixture was diluted with 20 mL DCM and evaporated by rotary evaporation. 3 mL of octanoyl chloride was added to the obtained product and the reaction mixture was stirred for 30 min at room temperature. The reaction mixture was diluted with 40 mL of DCM and washed with 30 mL $H_2O$ (pH~8). The aqueous layer was washed again with DCM (30 mL). The combined organic layers were dried over $Na_2SO_4$ and evaporated by rotary evaporation. Purification by column chromatography (Silica gel; 5-25% MeOH:DCM) gave corresponding acid (144.5 mg) as a mixture (80%; analyzed by LCMS). To this mixture in DMF (2 mL), EDC.HCl (70.4 mg), HOBt (80%; 59.2 mg), H-Lys(Boc)-OMe.HCl (106.3 mg) and triethyl amine (0.52 mL; 0.342 M in DMF) was added. After 40 min stirring at room temperature, the reaction was diluted with 30 mL DCM and washed with $H_2O$ (20 mL; pH-3). The organic layer was collected, dried with $Na_2SO_4$, and evaporated by rotary evaporation. The crude was purified by successive column chromatography (Silica gel; a. 2% MeOH:DCM, b. 25-60% EtOAc:Hexane) to afford 8 (96.0 mg; 27% yield). $R_f$: 0.4 (silica gel TLC; 1:1 EtOAc:Hexane). HRA-MS(+): Calculated for $C_{47}H_{60}N_4O_{11}S$ [M$^+$] 888.3979; found 888.3994. $^1$H-NMR (500 MHz; CDCl$_3$), δ: 8.00 (d, J=7.5 Hz, 1H), 7.62 (m, 2H), 7.15 (d, J=7.6 Hz, 1H), 7.09 (d, J=1.6 Hz, 1H), 6.80-6.75 (m, 2H), 6.59 (d, J=8.9 Hz, 1H), 6.47 (d, J=2.2 Hz, 1H), 6.40 (dd, J=8.8, 2.4 Hz, 1H), 4.82-4.72 (m, 1H), 4.61-4.55 (m, 2H), 3.73 (d, J=3.1 Hz, 3H), 3.51-3.47 (m, 1H), 3.32 (m, 1H), 3.05 (s, 3H), 2.97 (d, J=9.9 Hz, 7H), 2.55 (t, J=7.6 Hz, 2H), 1.88-1.83 (m, 1H), 1.67-1.61 (m, 4H), 1.47-1.40 (m, 11H), 1.31-1.23 (m, 11H), 0.83 (t, J=5.8 Hz, 3H). $^{13}$C-NMR (126 MHz; CDCl$_3$), δ: 198.8, 172.5, 172.3, 169.6, 168.8, 156.1, 155.2, 154.0, 153.2, 152.5, 152.3, 152.2, 135.0, 129.7, 129.1, 128.7, 127.0, 125.0, 124.2, 117.0, 110.2, 109.2, 105.9, 98.5, 83.5, 79.2, 60.5, 59.8, 59.3, 52.7, 52.6, 52.3, 52.2, 44.2, 40.3, 32.0, 31.8, 31.7, 29.5, 29.0, 28.5, 27.3, 25.6, 22.6, 21.2, 14.3, 14.1.

A solution of 8 (96 mg; 0.108 mmol; 1 eq) in 20% TFA:DCM (3 mL) was stirred at room temperature. After 10 min, the reaction mixture was diluted with 10 mL DCM and evaporated three times to remove all TFA. The crude product was purified by column chromatography (Silica gel; 5% MeOH:DCM (0.1% TFA)) to afford DPP-3 (75.3 mg; 88% yield). $R_f$: 0.06 (silica gel TLC; 5% MeOH:DCM(0.1% TFA)). HRA-MS(+): Calculated for $C_{42}H_{52}N_4O_9S$ [M$^+$] 788.3455; found 788.3462. $^1$H-NMR (500 MHz; CD$_3$OD), δ: 8.28 (d, J=7.4 Hz, 1H), 7.81 (dt, J=23.9, 7.3 Hz, 2H), 7.61 (d, J=10.6 Hz, 1H), 7.36 (d, J=6.8 Hz, 1H), 7.20 (t, J=10.7 Hz, 2H), 7.11 (s, 2H), 6.98 (s, 1H), 4.98 (s, 8H), 3.70 (d, J=7.8 Hz, 3H), 3.53 (m, 1H), 3.40 (m, 1H), 3.09 (s, 2H), 2.95 (s, 1H), 2.86 (s, 2H), 2.54 (m, 1H), 1.92-1.91 (m, 1H), 1.79 (s, 1H), 1.64-1.61 (m, 4H), 1.43 (m, 2H), 1.26-1.19 (m, 12H), 0.80 (t, J=6.2 Hz, 3H). $^{13}$C-NMR (126 MHz; CD$_3$OD), δ: 200.2, 173.6, 173.0, 171.1, 170.9, 168.7, 159.5, 158.8, 157.7, 155.6, 155.1, 154.6, 134.8, 132.5, 131.8, 131.0, 130.9, 129.8, 120.9, 120.7, 119.9, 119.7, 117.5, 111.4, 111.32, 111.1, 98.4, 61.5, 60.8, 60.7, 54.0, 53.7, 52.8, 44.8, 41.6, 40.4, 33.1, 32.7, 31.4, 31.4, 30.00, 29.9, 29.0, 28.5, 27.9, 27.8, 26.7, 26.6, 24.1, 23.9, 23.6, 20.9, 14.4.

Example 5

In Vitro Activity of APTs with DPP-1, DPP-2, and DPP-3

Figure 4A:
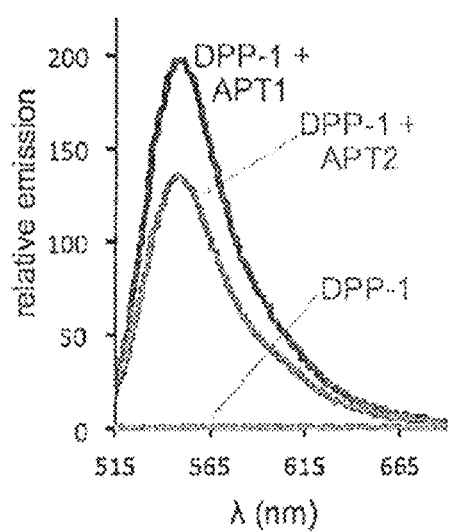
FIG. 4A is a graph showing the fluorescence emission spectrum of a 5 micromolar (μM) solution of depalmitoylation probe 1 (DPP-1) in 4-(2-hydroxyethyl)-1-piperazineethanesulfonic acid (HEPES) buffer (20 millimolar mM, at pH 7.4, 150 mM sodium chloride (NaCl) and 1% Triton X-100), as well as the fluorescence emission spectra after treatment of DPP-1 with either 50 nanomolar (nM) acyl protein thioesterase 1 (DPP-1+APT1) or with 50 nM acyl protein thiotransferase 2 (DPP-1+APT2) for 20 minutes. The excitation wavelength ($\lambda_{ex}$) is 485 nanometers (nm).
Figure 5A:
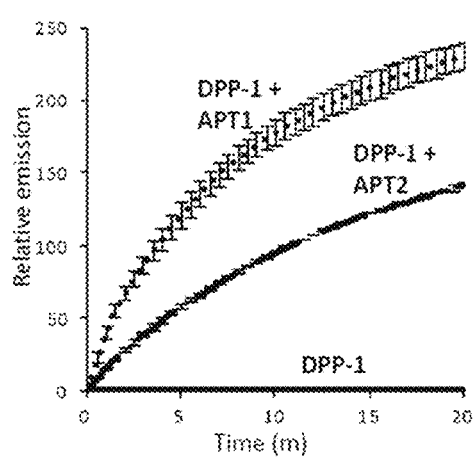
FIG. 5A is a graph showing the results of an in vitro fluorescence assay of 5 micromolar (μM) depalmitoylation probe 1 (DPP-1). The assay was performed with either 50 nanomolar (nM) purified acyl protein thioesterase 1 (DPP-1+APT1) or 50 nM acyl protein thioesterase 2 (DPP-1+APT2). The excitation wavelength ($\lambda_{ex}$) was 490/9 nanometers (nm) and the emission wavelength ($\lambda_{em}$) was 545/20 nm. Error bars are standard deviation (n=3). Data was normalized to the background of the background fluorescence of the probe alone.

Carbamate-containing DPPs DPP-1, DPP-2, and DPP-3 were synthesized as described above in Examples 2-4. As expected, carbamate modification on DPP-1 forces the rhodol fluorophore of these DPPs into the lactone form, which has minimal visible absorbance and very low fluorescence. See FIGS. 3A-3D. However, incubation of 5 μM DPP-1 with either 50 nM APT1 or 50 nM APT2 resulted in an ~250-fold enhancement in fluorescence signal after 20 min. See FIG. 4A and FIG. 5A. These data validate the general DPP design strategy and confirm that DPP-1 is a good substrate for in vitro APT biochemical assays. However, since DPP-1 has relatively poor water solubility, detergents were used to facilitate the running of the in vitro assays.

Figure 4B:
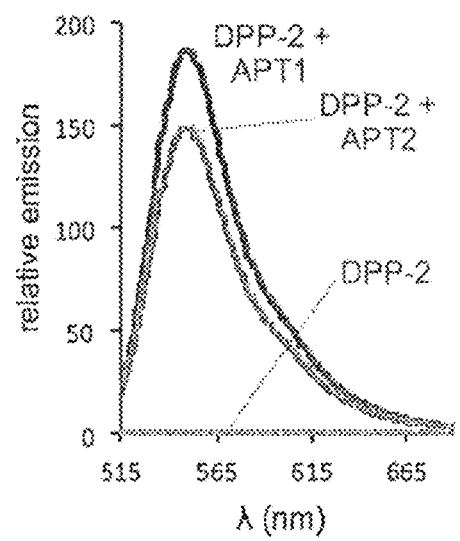
FIG. 4B is a graph showing the fluorescence emission spectrum of a 5 micromolar (μM) solution of depalmitoylation probe 2 (DPP-2) in 4-(2-hydroxyethyl)-1-piperazineethanesulfonic acid (HEPES) buffer (20 millimolar mM, at pH 7.4, 150 mM sodium chloride (NaCl) and 1% Triton X-100), as well as the fluorescence emission spectra after treatment of DPP-2 with either 50 nanomolar (nM) acyl protein thioesterase 1 (DPP-2+APT1) or with 50 nM acyl protein thiotransferase 2 (DPP-2+APT2) for 20 minutes. The excitation wavelength ($\lambda_{ex}$) is 485 nanometers (nm).
Figure 4C:
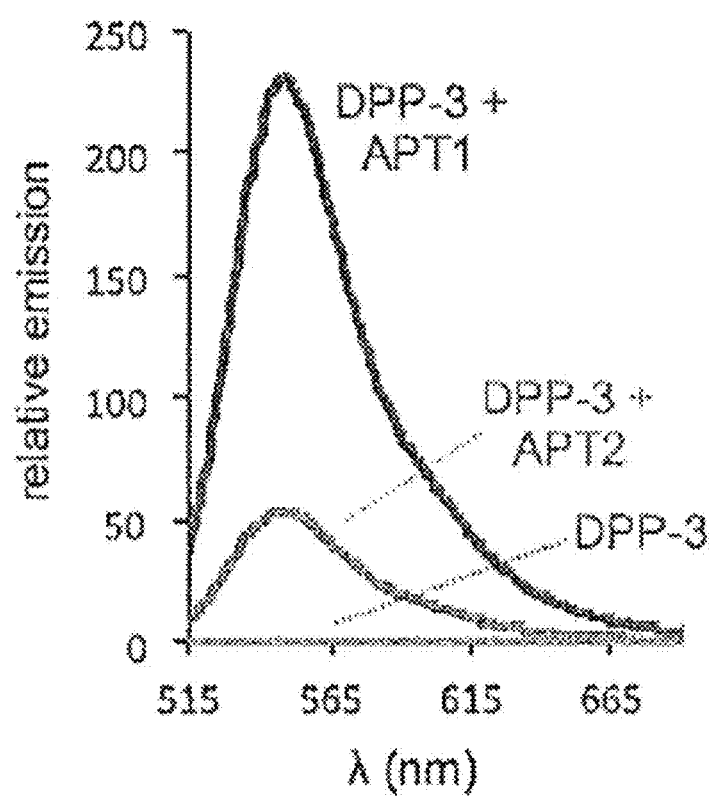
FIG. 4C is a graph showing the fluorescence emission spectrum of a 5 micromolar (μM) solution of depalmitoylation probe 3 (DPP-3) in 4-(2-hydroxyethyl)-1-piperazineethanesulfonic acid (HEPES) buffer (20 millimolar mM, at pH 7.4, 150 mM sodium chloride (NaCl) and 1% Triton X-100), as well as the fluorescence emission spectra after treatment of DPP-3 with either 50 nanomolar (nM) acyl protein thioesterase 1 (DPP-3+APT1) or with 50 nM acyl protein thiotransferase 2 (DPP-3+APT2) for 20 minutes. The excitation wavelength ($\lambda_{ex}$) is 485 nanometers (nm).
Figure 5B:
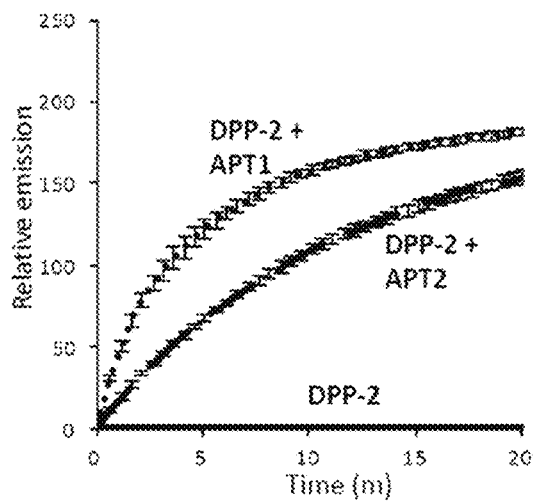
FIG. 5B is a graph showing the results of an in vitro fluorescence assay of 5 micromolar (μM) depalmitoylation probe 2 (DPP-2). The assay was performed with either 50 nanomolar (nM) purified acyl protein thioesterase 1 (DPP- 2+APT1) or 50 nM acyl protein thioesterase 2 (DPP-2+APT2). The excitation wavelength ($\lambda_{ex}$) was 490/9 nanometers (nm) and the emission wavelength ($\lambda_{em}$) was 545/20 nm. Error bars are standard deviation (n=3). Data was normalized to the background of the background fluorescence of the probe alone.
Figure 5C:
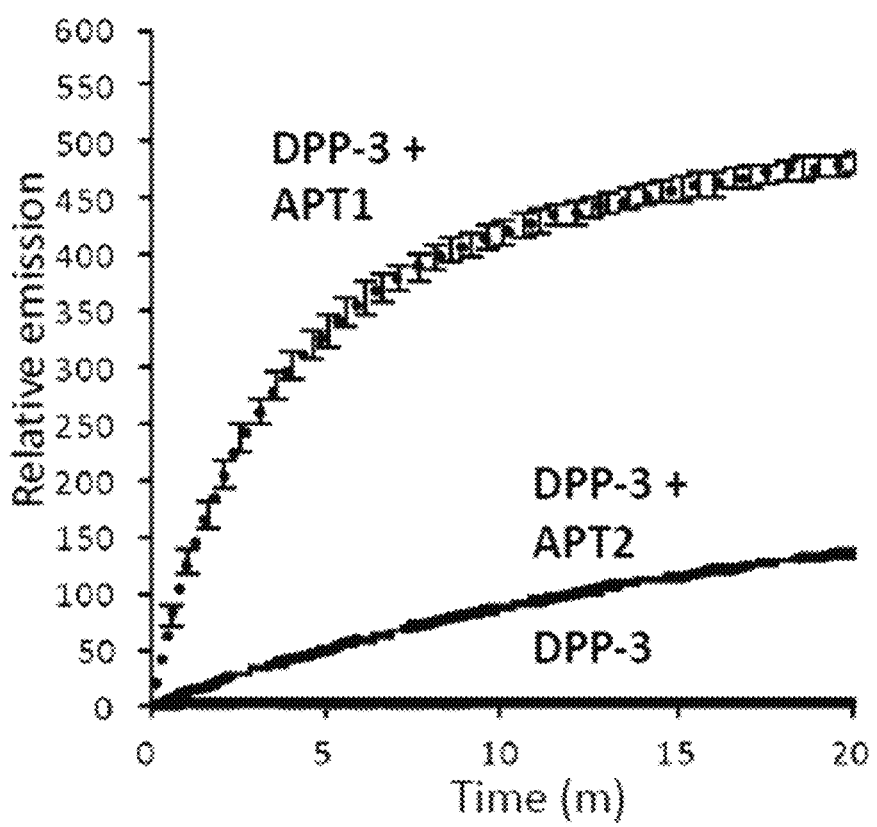
FIG. 5C is a graph showing the results of an in vitro fluorescence assay of 5 micromolar (μM) depalmitoylation probe 3 (DPP-3). The assay was performed with either 50 nanomolar (nM) purified acyl protein thioesterase 1 (DPP-3+APT1) or 50 nM acyl protein thioesterase 2 (DPP-3+APT2). The excitation wavelength ($\lambda_{ex}$) was 490/9 nanometers (nm) and the emission wavelength ($\lambda_{em}$) was 545/20 nm. Error bars are standard deviation (n=3). Data was normalized to the background of the background fluorescence of the probe alone.
Figure 6A:
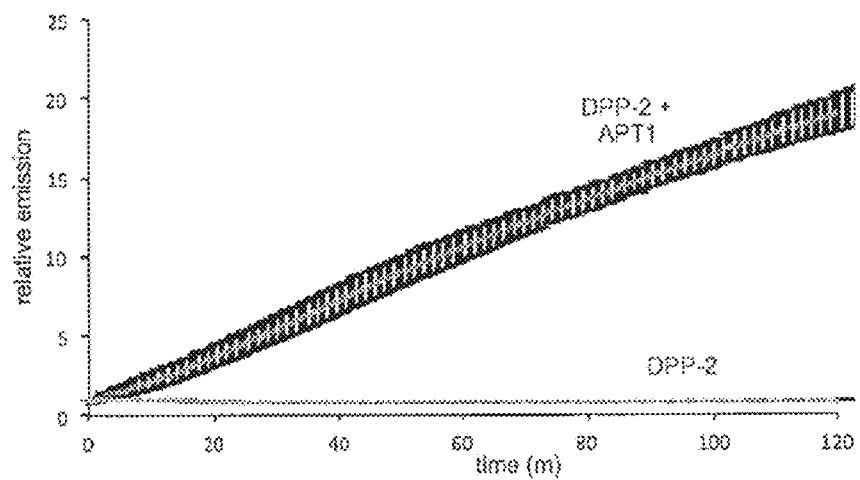
FIG. 6A is a graph showing the in vitro fluorescence assay of 25 micromolar (μM) depalmitoylation probe 2 (DPP-2) without detergent in 20 millimolar (mM) 4-(2-hydroxyethyl)-1-piperazineethanesulfonic acid (HEPES) buffer, either alone or with 50 nanomolar (nM) purified acyl protein thioesterase 1 (+APT1). The excitation wavelength ($\lambda_{ex}$) was 490/9 nanometers (nm) and the emission wavelength ($\lambda_{em}$) was 545/20 nm. Error bars are standard deviation (n=3).
Figure 6B:
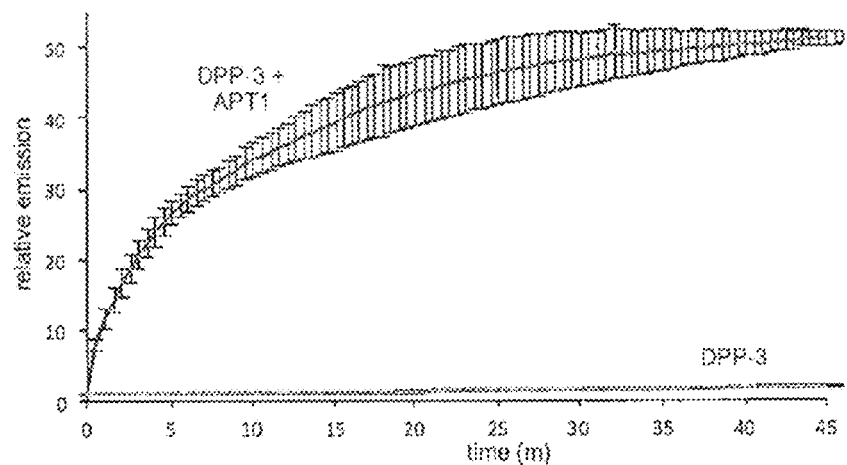
FIG. 6B is a graph showing the in vitro fluorescence assay of 25 micromolar (μM) depalmitoylation probe 3 (DPP-3) without detergent in 20 millimolar (mM) 4-(2-hydroxyethyl)-1-piperazineethanesulfonic acid (HEPES) buffer, either alone or with 50 nanomolar (nM) purified acyl protein thioesterase 1 (+APT1). The excitation wavelength ($\lambda_{ex}$) was 490/9 nanometers (nm) and the emission wavelength ($\lambda_{em}$) was 545/20 nm. Error bars are standard deviation (n=3).

DPP-2 has a $C_7$-lipid rather than a $C_{15}$-lipid. In vitro assays with purified APTs revealed that DPP-2 in fact functions slightly better than DPP-1 as a substrate, possibly due to improved solubility. See FIG. 4B and FIG. 5B. With a structure based on both the natural N-Ras substrate and pharmacological data (see Davda and Martin (2014) Medchemcomm 5, 268-276), DPP-3 features an additional lysine residue. In vitro assays of DPP-3 revealed striking reaction kinetics with APT1 (see FIG. 4C and FIG. 5C) and a modest selectivity for APT1 over APT2, confirming that target engagement can be tuned by modifications proximal to the acyl cysteine. Since both DPP-2 and DPP-3 are water soluble, the enzymatic assays can be performed in the absence of detergents. See FIGS. 6A and 6B. Confirming the in vitro response of the DPPs, catalytically inactivating point mutations and inhibitors (see FIG. 7) abrogate the DPP signal.

Example 6

Live Cell Assays with DPP-1, DPP-2, and DPP-3

Figures 9A, 9B:
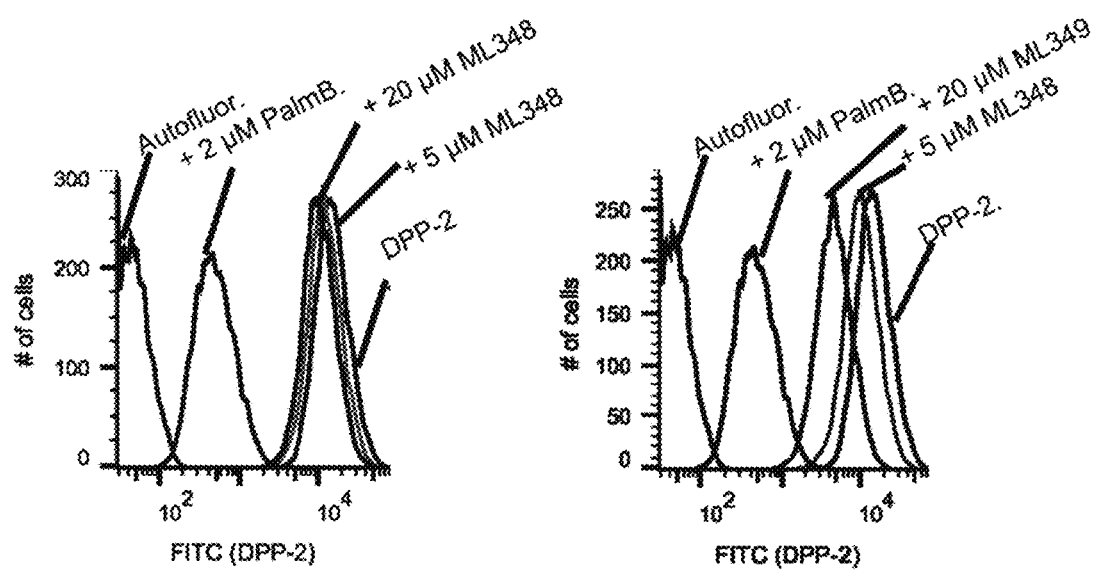
FIG. 9A is a graph showing the results of the flow cytometry analysis of the inhibition of depalmitoylation probe 2 (DPP-2). Human embryonic kidney (HEK293T) cells were loaded with 5 micromolar (μM) DPP-2 for 5 minutes after pretreatment with either dimethylsulfoxide (DMSO) or an inhibitor (2 μM pan-acyl protein thioesterase (APT) inhibitor palmostatin B (PalmB) or 5 μM or 20 μM of acyl protein thioesterase 1 (APT1)-specific inhibitor ML348), and then analyzed by flow cytometry.
FIG. 9B is a graph showing the results of the flow cytometry analysis of the inhibition of depalmitoylation probe 2 (DPP-2). Human embryonic kidney (HEK293T) cells were loaded with 5 micromolar (μM) DPP-2 for 5 minutes after pretreatment with either dimethylsulfoxide (DMSO) or an inhibitor (2 μM pan-acyl protein thioesterase inhibitor (APT) palmostatin B (PalmB) or 5 μM or 20 μM acyl protein thioesterase (APT2)-specific inhibitor ML349), and then analyzed by flow cytometry.
Figure 10:
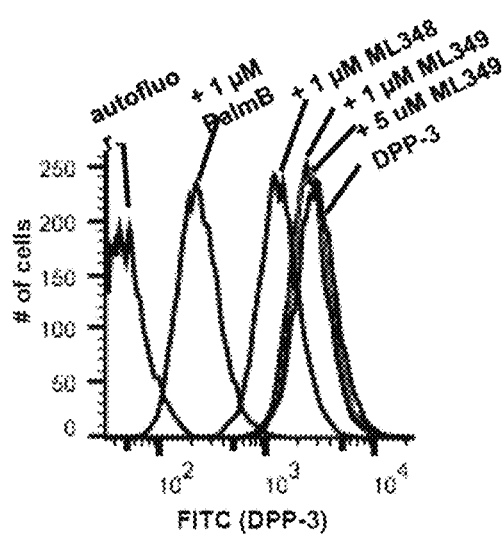
FIG. 10 is a graph showing the results of the flow cytometry analysis of the inhibition of depalmitoylation probe 3 (DPP-3). Human embryonic kidney (HEK293T) cells were loaded with 5 micromolar (μM) DPP-2 for 5 minutes after pretreatment with either dimethylsulfoxide (DMSO) or an inhibitor (1 μM pan-acyl protein thioesterase (APT) inhibitor palmostatin B (PalmB), 1 μM acyl protein thioesterase 1 (APT1)-specific inhibitor ML348 or 1 μM or 5 μM acyl protein thioesterase 2 (APT2)-specific inhibitor ML349), and then analyzed by flow cytometry.
Figure 11:
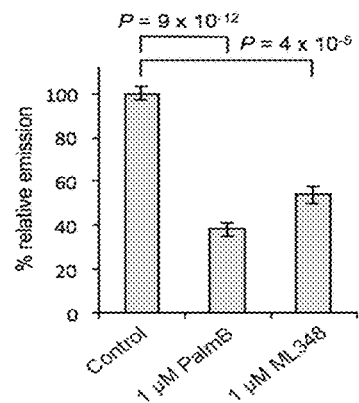
FIG. 11 is a graph showing the relative fluorescence response of depalmitoylation probe 3 (DPP-3), in human embryonic kidney (HEK293T) cells. One micromolar (μM) DPP3 was loaded into HEK293T cells for 15 minutes after treatment with either dimethylsulfoxide (DMSO, "Control"), 1 μM pan-acyl protein thioesterase (APT) inhibitor palmostatin B (PalmB) or 1 μM acyl protein thioesterase 1 (APT1)-specific inhibitor ML348, and then analyzed by fluorescence microscopy. Error bars are ±standard deviation (n=6). Statistical analysis was performed with a two-tailed Student's t-test with unequal variance.

Given that DPP-2 and DPP-3 show a 200- and 400-fold enhancement in fluorescence (see FIGS. 4B and 4C respectively) after 20 min of reaction with 50 nM APT1 and function in water, live-cell experiments were pursued. Whole human embryonic kidney (HEK293T) cells were used as a model cell line. Incubation of HEK293T cells with 1 μM DPP-2 for 15 min resulted in robust intracellular fluorescent signal as monitored by live cell fluorescence microscopy (See FIG. 8) or flow cytometry (see FIGS. 9A and 9B), confirming the presumed high basal activity of APTs. The fluorescent signal is perturbed by inhibition with 2 μM PalmB, 5 μM ML348, or 5 μM ML349. See FIGS. 9A and 9B. DPP-3 also functions in live cells, except inhibition with lower amounts of PalmB or ML348 were needed to perturb the signal. See FIGS. 10 and 11. Without being bound to any one theory, this result is believed to be due to better uptake of DPP-2. Moreover, the DPP-3 signal is not substantially perturbed by the APT2 inhibitor ML349 (See FIG. 10), suggesting DPP-3 selectivity in live cells mirrors what was observed in vitro.

Figure 12A:
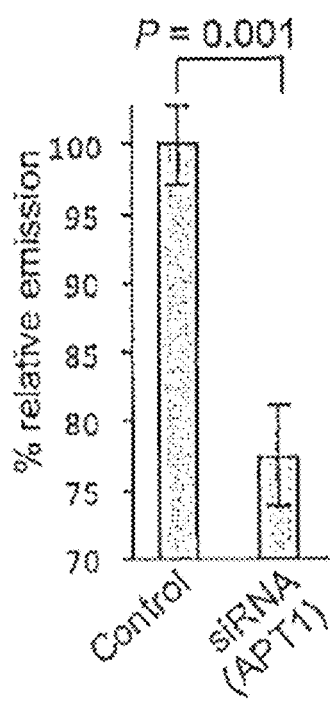
FIG. 12A is a graph showing the relative fluorescence response of depalmitoylation probe 3 (DPP-3) in human embryonic kidney (HEK293T) cells without (control) or with RNA interference (RNAi) knockdown of acyl protein thioesterase 1 (APT1). Five micromolar (μM) DPP3 was loaded into HEK293T cells for 15 minutes after treatment with either a control small interfering RNA (siRNA) or a siRNA targeting APT1. Error bars are ±standard deviation (n=6). Statistical analysis was performed with a two-tailed Student's t-test with unequal variance.
Figure 12B:
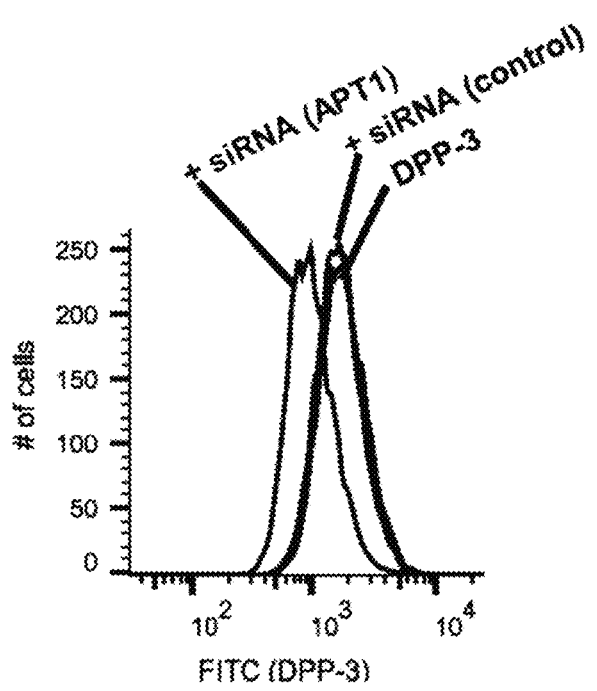
FIG. 12B is a graph showing the fluorescence response of depalmitoylation probe 3 (DPP-3) in human embryonic kidney (HEK293T) cells with or without RNA interference (RNAi) knockdown of acyl protein thioesterase 1 (APT1). Five micromolar (μM) DPP3 was loaded into HEK293T cells for 5 minutes after treatment with either a control small interfering RNA (siRNA (control)) or a siRNA targeting APT1 (siRNA(APT1)) and then the cells were analyzed by flow cytometry. Analysis of DPP-3 without any siRNA (DPP-3) is also shown.

To further validate the inhibitor experiments, RNAi knockdown of APT1 was determined to block the DPP-3 signal similarly to ML348. See FIGS. 12A and 12B. However, neither APT1 knockdown or ML348 treatment blocked the signal to the same level as PalmB treatment. Without being bound to any one theory, it is believed that either APT2 or other depalmitoylases can act on DPP-3.

Figure 13A:
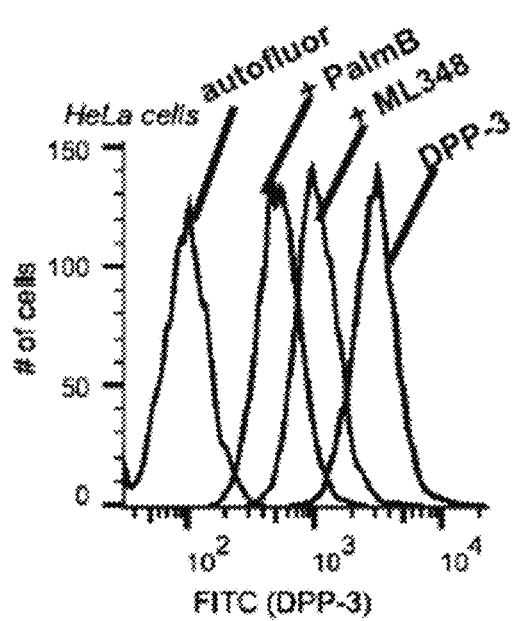
FIG. 13A is a graph showing the flow cytometry analysis of depalmitoylation probe 3 (DPP-3) in human cervical cancer (HeLa) cells. HeLa cells were loaded with 5 micromolar (μM) DPP-3 for 5 minutes and then analyzed by flow cytometry. Inhibition by either 1 μM palmostatin B (PalmB) or 1 μM ML348 knocks down the depalmitoylation signal as measured by DPP-3 Analysis of DPP-3 alone (DPP-3) is also shown.
Figure 13B:
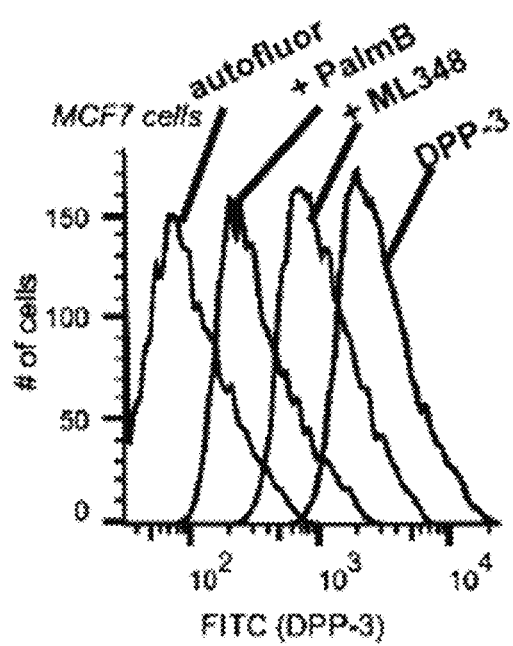
FIG. 13B is a graph showing the flow cytometry analysis of depalmitoylation probe 3 (DPP-3) in human breast adenocarcinoma (MCF-7) cells. MCF-7 cells were loaded with 5 micromolar (μM) DPP-3 for 5 minutes and then analyzed by flow cytometry. Inhibition by either 1 μM palmostatin B (PalmB) or 1 μM ML348 knocks down the depalmitoylation signal as measured by DPP-3. Analysis of DPP-3 alone (DPP-3) is also shown.
Figure 13C:
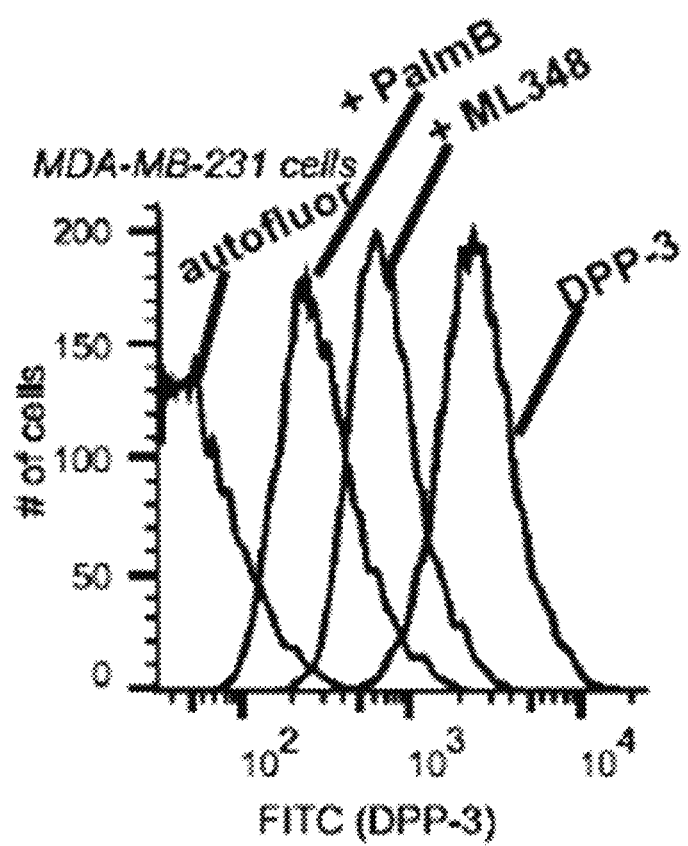
FIG. 13C is a graph showing the flow cytometry analysis of depalmitoylation probe 3 (DPP-3) in human breast adenocarcinoma (MDA-MF-231) cells. MDA-MF-231 cells were loaded with 5 micromolar (μM) DPP-3 for 5 minutes and then analyzed by flow cytometry. Inhibition by either 1 μM palmostatin B (PalmB) or 1 μM ML348 knocks down the depalmitoylation signal as measured by DPP-3. Analysis of DPP-3 alone (DPP-3) is also shown.

Finally, to confirm that DPP-3 can function in a variety of cell types, the flow cytometry experiments were repeated in HeLa, MCF-7, and MDA-MB-231 cells, which revealed that DPP-3 can detect endogenous depalmitoylase activities in each of these model cell lines. See FIGS. 13A-13C. Collectively, these results appear to confirm that DPPs, such as both DPP-2 and DPP-3, can measure endogenous depalmitoylase levels in a variety of cellular contexts.

Figure 14:
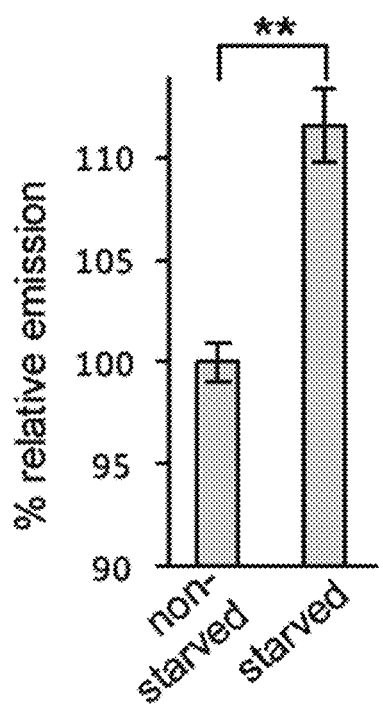
FIG. 14 is a graph showing the relative fluorescence of depalmitoylation probe 3 (DPP-3) in human epidermoid carcinoma (A431) cells under non-starved and starved conditions. A431 cells were grown in normal media conditions ("non-starved") or serum starved conditions for 24 hours and then loaded with 5 micromolar (μM) DPP-3 for 15 minutes and analyzed by fluorescence microscopy.
Figure 15:
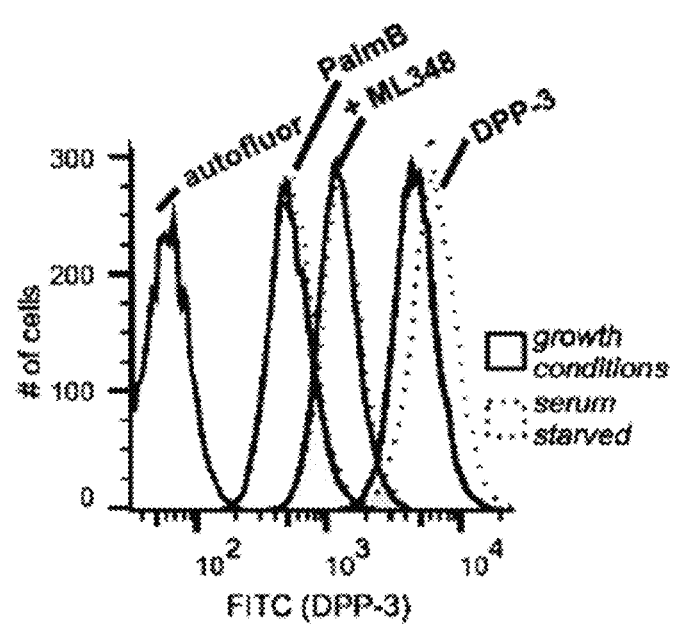
FIG. 15 is a graph showing the flow cytometry analysis of depalmitoylation probe 3 (DPP-3) in human epidermoid carcinoma (A431) cells under non-starved and starved conditions. A431 cells were grown in normal media conditions (solid lines) or serum starved conditions (dotted lines) for 24 hours and then loaded with 5 micromolar (μM) DPP-3 for 15 minutes and analyzed by flow cytometry. Inhibition by either 1 μM palmostatin B (PalmB) or 1 μM of acyl protein thioesterase 1 (APT1)-specific inhibitor ML348 knocks down the depalmitoylation signal as measured by DPP-3. Analysis further indicates that serum starvation increases the depalmitoylase activity, but is knocked down to comparable levels as observed under growth conditions by treatment with inhibitor.
Figure 16:
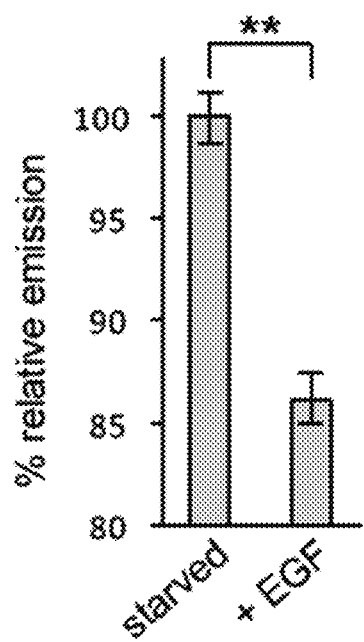
FIG. 16 is a graph showing the relative fluorescence of depalmitoylation probe 3 (DPP-3) in human epidermoid carcinoma (A431) cells under starved conditions in the presence or absence of 1 nanogram per milliliter (ng/mL) of epidermal growth factor (EGF). A431 cells were grown in serum starved conditions for 24 hours and then loaded with 5 micromolar (μM) DPP-3 for 15 minutes in either the absence (starved) or presence of 1 ng/mL EGF (EGF) and analyzed by fluorescence microscopy.

Encouraged by the performance of DPPs in live cells, the hypothesis that cell signaling events modulate depalmitoylase activity levels was studied. DPP-3 was deployed in epidermoid carcinoma A431 cells, which express high levels of the epidermal growth factor (EGF) receptor, respond to EGF stimulation, and are devoid of endogenous mutations of HRAS, KRAS and NRAS. It was hypothesized that DPP-3 is detecting the APT(s) that regulate NRAS, since the probe was designed based on this substrate, and that if S-palmitoylation signaling is indeed regulated at the depalmitoylase level, cells with normal Ras signaling would be more likely to show an effect. A431 cells were serum starved to make them susceptible to transient activation by EGF, which intriguingly resulted in an increase in basal depalmitoylase activity levels, which is knocked down by inhibition with PalmB or M348 to similar levels as non-serum starved cells. See FIGS. 14 and 15. Even more strikingly, stimulation of serum starved cells with 1 ng/mL EGF for 15 min results in an inhibition of depalmitoylation activity (see FIG. 16), which appears to confirm the hypothesis that APTs are in fact dynamically regulated by upstream signaling events.

Figure 17:
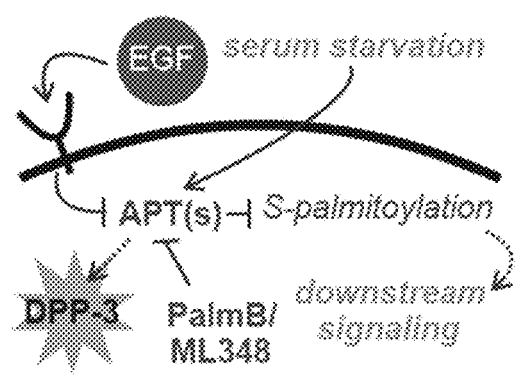
FIG. 17 is a schematic diagram showing a proposed epidermal growth factor (EGF)-induced depalmitoylation signaling pathway through transient deactivation of acyl protein thioesterases.

Further, the present disclosure of EGF-induced deactivation of depalmitolyation activity supports a proposed model in which membrane-bound proteins are activated via enhanced membrane retention through inhibition of APTs. See FIG. 17. Thus, without being bound to any one theory, it appears that depalmitoylation is dynamically regulated in a temporally dynamic manner.

Example 7

Methods and Materials for Examples 8-13

Synthetic Materials and Methods.

Silica gel P60 (SiliCycle, Inc., Quebec City, Canada; 40-63 µm, 230-400 mesh) was used for column chromatography. Analytical thin layer chromatography was performed using SiliCycle 60 F254 silica gel (SiliCycle Inc., Quebec City, Canada; precoated sheets, 0.25 mm thick). All chemicals for synthesis were purchased from Sigma-Aldrich (St. Louis, Mo., United States of America) or Fisher Scientific (Pittsburgh, Pa., United States of America) and used as received. ML348 and ML349 were purchased from Tocris (Bristol, United Kingdom). $^{1}$H-NMR and $^{13}$C-NMR spectra were collected in NMR solvents $CDCl_3/(CD_3)_2CO$ (Sigma-Aldrich, St Louis, Mo., United States of America) at 25° C. using a 500 MHz Bruker Avance II+ spectrometer (Bruker Corporation, Billerica, Mass., United States of America) with 5 mm QNP probe. $^{1}$H-NMR chemical shifts are reported in parts per million (ppm) relative to the peak of residual proton signals from ($CDCl_3$ 7.26 ppm or $(CD_3)_2CO$ 2.05 ppm). Multiplicities are given as: s (singlet), d (doublet), t (triplet), q (quartet), dd (doublet of doublets), m (multiplet). $^{13}$C-NMR chemical shifts are reported in parts per million (ppm) relative to the peak of residual proton signals from ($CDCl_3$ 77.16 ppm or $(CD_3)_2CO$ 29.84 ppm amd 206.26 ppm). Analysis of NMR and plots were obtained using TopSpin 3.5 pl 7 (Bruker Corporation, Billerica, Mass., United States of America). High resolution mass was obtained from Agilent 6224 TOF High Resolution Accurate Mass Spectrometer (HRA-MS) (Agilent Technologies, Santa Clara, Calif., United States of America) using combination of APCI and ESI. Low resolution mass spectral analyses and liquid chromatography analysis were carried out on an Advion Expression-L mass spectrometer (Ithaca, N.Y., United States of America) coupled with an Agilent 1220 Infinity LC System (Agilent Technologies, Santa Clara, Calif., United States of America). All experiments utilizing a plate reader were carried out on a BioTek (Winooski, Vt., United States of America) monochromator-based Synergy Neo2 Multi-Mode Reader at 37° C. IUPAC names for compounds were generated using MarvinSketch (Version 17.8.0, ChemAxon, Budapest, Hungary). tert-butyl (R)-methyl(1-(methylamino)-1-oxo-3-(tritylthio)propan-2-yl)carbamate and N-(tert-butoxycarbonyl)-N-methyl-S-trityl-L-cysteine were obtained as previously reported. See Kathavat et al. (2017) Nat Chem Biol 13, 150-152; and Vippila et al. (2015) J Nat Prod 78, 2398-2404.

Purification of APT1 and APT2.

Recombinant human APT1, APT2, APT1(S119A), and APT2(S122A) were purified as described above in Example 1. Purified proteins were stored in individual aliquots in protein storage buffer (50 mM Tris-HCl, pH 7.5, 300 mM NaCl, 1 mM DTT, 10% Glycerol) at 80° C. A fresh aliquot of protein was thawed for each experiment.

In Vitro Kinetic Assays of RDP-1 and RDP-2.

100 µL of 400 nM of APT1 or APT2, or buffer without added enzymes, were added to buffer (20 mM HEPES, 150 mM NaCl, 0.1% Triton X-100, pH 7.4, degassed by bubbling $N_2$ through the solution for 1 h) and prewarmed to 37° C. in a heating block for 5 min. The buffer solutions were then added using a multichannel pipet to a black-walled clear-bottom 96-well plate (Nunc, Roskilde, Denmark) containing 100 µL of 2 µM RDP-1 or RDP-2 in buffer (20 mM HEPES, 150 mM NaCl, 0.1% Triton X-100, pH 7.4, 0.15% DMSO) that had been pre-warmed in the plate reader at 37° C. for 5 min, resulting in a final concentration of 200 nM APT1 or APT2, 1 µM RDP-1 or RDP-2, and 0.1% DMSO. Fluorescent intensities $\lambda_{ex1}$=430/24 nm, $\lambda_{em1}$=470/24 nm; $\lambda_{ex2}$=480/20, $\lambda_{em2}$=575/40; gain=75; No. of flashes=8) were obtained as a ratio of em1/em2 in kinetic mode in 30 s intervals for 30 min. For the catalytically inactive enzyme experiments, 10 times more APT1(S119A) and APT2 (S122A) enzyme were used.

Stability of RDP-1 and RDP-2 with Biological Reductant.

RDP-1 or RDP-2 were added to buffer (20 mM HEPES, 150 mM NaCl, 0.1% Triton X-100, pH 7.4, degassed by bubbling $N_2$ through the solution for 1 h) prewarmed to 37° C. in a heating block for 5 min containing no reducing agent or GSH using a multichannel pipet to at least three wells of a black-walled clear-bottom 96-well plate (Nunc, Roskilde, Denmark; Final concentration: 1 µM RDP-1/RDP-2, 20 mM GSH, 20 mM HEPES, 150 mM NaCl, 0.1% Triton X-100, pH 7.4, 4.1% DMSO). Fluorescent intensities ($\lambda_{ex1}$=430/25 nm, $\lambda_{em}$1=470/24 nm; $\lambda_{ex2}$=480/20, $\lambda_{em2}$=575/40; gain=75;

No. of flashes=10) were obtained as a ratio of $em_1/em_2$ in kinetic mode in 30 s intervals for 30 min.

UV-Vis and Fluorescence Spectra.

A 30 µM solution of RDP-1 or RDP-2 in buffer (20 mM HEPES, 150 mM NaCl, 0.1% Triton X-100, pH 7.4, 0.15% DMSO) was diluted in half with buffer or buffer containing DTT (20 mM HEPES, 150 mM NaCl, 0.1% Triton X-100, pH 7.4, 40 mM DTT) to chemically deacylate the probe. After 1 h incubation at room temperature, 150 µL of the solutions were placed in a black-walled glass-bottom 96-well plate (Celvis, Mountain View, Calif., United States of America) and UV-Vis measurements (No. of flashes=8, step size=1 nm), fluorescent emission ($\lambda_{Ex1}$=430/24 nm, $\lambda_{Em1}$=450/5 nm to 800 nm, step size=1 nm, gain=57, No. of flashes=10; $\lambda_{Ex2}$=480/20 nm, $\lambda_{Em2}$=500/5 nm to 800 nm, step size=1 nm, gain=95, No. of flashes=10), and fluorescent excitation spectra ($\lambda_{Ex1}$=300/24 nm to 450 nm, $\lambda_{Em1}$=470/5 nm, step size=1 nm, gain=57, No. of flashes=10; $\lambda_{Ex2}$=400/20 nm to 550 nm, $\lambda_{Em2}$=575/5 nm, step size=1 nm, gain=95, No. of flashes=10) were obtained on a plate reader.

Cell Culture and Maintenance.

HEK293T (ATCC) and HEPG2 (gift from Prof. Chuan He) cells were maintained in DMEM/High Glucose (10% FBS, 1% P/S, L-Glutamine, Sodium pyruvate, Gibco/Life Technologies, Gaithersburg, Md., United States of America) with 10% FBS (Gibco/Life Technolgies, Gaithersburg, Md., United States of America; Qualified US origin) at 37° C. and 5% $CO_2$. The cells were then used for less than 25 passages for all experiments. Multiple biological replicates were performed with cells from different passages and freshly thawed aliquots.

Colon Organoids Culture and Maintenance.

Generation of human colon organoids was performed as previously described (see Sato et al. (2011) Gastroenterology 141, 1762-1772) with some modifications. Briefly, pinch biopsies from colons of healthy human subjects were collected and washed three times with ice-cold phosphate buffered saline (PBS) before an incubation at 4° C. in 8 mM EDTA/PBS for 30 min, with gentle agitation. Individual crypts were released from the tissue by repeated tituration through a P1000 tip. Crypts and tissue were passed through a 100 um cell strainer (FALCON™ 352360; Corning Life Sciences, Corning, N.Y., United States of America). Crypts were then transferred to a microfuge tube and centrifuged at 300 g for 5 min. Supernatant was discarded and pellets were resuspended in human organoid growth media [Advanced DMEM/F12, Glutamax, 1×HEPES buffer, Pen/Strep, N2 supplement, B-27 Supplement Minus Vitamin A (Thermo Fisher Scientific, Waltham, Mass., United States of America), 1.25 mM N-acetyl-L-(+)-cysteine, 10 mM Nicotinamide, 50% L-WRN conditioned media (L-WRN cells were a generous gift from T. C. He, Department of Surgery, The University of Chicago, Chicago, Ill., United States of America), murine epidermal growth factor (50 ng/mL; Peprotech, Rocky Hill, N.J., United States of America), recombinant human R-spondin1 (500 ng/mL; Peprotech), Jagged-1 (1 µM; Anaspec, Fremont, Calif., United States of America), 10 µM Y-27632, 30 µM SB202190, 500 nM A-8301, 2.5 µM Chir99021, 500 nM LY2157299 (all chemical compounds from Cayman Chemical, Ann Arbor, Mich., United States of America), 10 nM Leu15-Gastrin I and 10 µg/mL ciprofloxacin (Sigma Aldrich. St. Louis, Mo., United States of America)]. Organoids were mixed with Matrigel (Corning 356253, Corning Life Sciences, Corning, N.Y., United States of America) in a 1:2 ratio, plated onto pre-warmed 6-well tissue culture plates (Corning 3506, Corning Life Sciences, Corning, N.Y., United States of America), and placed in a 37° C./5% $CO_2$ incubator. After an hour, 2 mL organoid growth media was added. Organoids were maintained in culture for several weeks with media changes every 2-3 days.

Fluorescence Imaging of RDP-1 and RDP-2 with HEK293T Cells.

HEK293T were plated with 500 mL of DMEM (Gibco, Gaithersburg, Md., United States of America; High Glucose, Glutamax, 10% FBS) a four well chambered imaging dish (D35C4-20-1.5-N, Cellvis, Mountain View, Calif., United States of America) which were precoated with 4 µg Poly-D-lysine (30-70 kilodalton (KDa), Alfa Aesar, Haverhill, Mass., United States of America) for 2 h at room temperature or overnight at 4° C. and grown to ca. 80% confluence prior to imaging. 30 min before the addition of the RDP, the cell culture media was removed and cells were washed with 500 µL of serum-free DMEM (Gibco, Gaithersburg, Md., United States of America, High Glucose, Glutamax, no FBS). The media was then replaced with 500 µL of serum-free DMEM containing 100 nM Mitotracker Deep Red (Thermo Fisher Scientific, Waltham, Mass., United States of America; to assist in focusing and processing) and either 0.1% DMSO carrier as a control or Palm B, ML348, or ML349 in DMSO and incubated for 30 min at 37° C. and 5% $CO_2$. The media was removed, the cells were washed with 500 µL of Live Cell Imaging Solution (Thermo Fisher Scientific, Waltham, Mass., United States of America), and 500 µL of 1 µM RDP-1 or RDP-2 along with the appropriate inhibitor or DMSO as control in Live Cell Imaging Solution was added to each well. After incubation for 10 min at 37° C. and 5% $CO_2$, the cells were washed with 500 µL Live Cell Imaging Solution and 500 µL of Live Cell Imaging Solution containing DMSO or the appropriate inhibitor was added to the cells immediately before images were obtained on an inverted epi-fluorescence microscope (Olympus IX83; Olympus Corporation, Tokyo, Japan) attached with EMCCD camera (Photometrics EVOLVE™ Delta; Photometrics, Tucson, Ariz., United States of America) with 40× oil objective (N/A 1.3) for RDP-1 (excitation filter 1 430/24 nm, dichroic chroma 89007, emission filter 1 470/24 nm, exposure time 100 ms, EM gain 80, excitation filter 2 480/20 nm, dichroic chroma 49014, emission filter 2 575/40 nm, exposure time 70 ms, EM gain 50) or for RDP-2 (excitation filter 1 430/24 nm, dichroic chroma 89007, emission filter 1 470/24 nm, exposure time 70 ms, EM gain 50, excitation filter 2 480/20, dichroic chroma 49014, emission filter 2 575/40 nm, exposure time 50 ms, EM gain 30), brightfield (exposure time 50 ms, EM gain 30), and MitoTracker Deep Red: (excitation filter 640/30 nm, emission filter 705/72 nm, dichroic chroma 89016, exposure time 15 ms, EM gain 15). Analyses were performed in ImageJ as described below. Each experiment was repeated at least three separate times with identical results.

Epifluorescent Imaging of RDP-2 with APT1/APT2 shRNA.

Short Hairpin RNA (shRNA) plasmids were constructed in pLKO.1 vector (see Moffat et al. (2006) Cell 124, 1283-1298) by restriction cloning adapting the protocol available on the Addgene organization website. Three shRNAs were constructed for APT1 and two shRNAs were constructed for APT2 using the Broad Institute's Online Genetic Perturbation Platform database. The sequences for each target are shown in Table 1, below.

TABLE 1

Sequences for RNAi.

| Target | Sequence | SEQ ID Number |
|---|---|---|
| APT1 | CGGTGGTGCTAATAGAGATAT | SEQ ID NO: 1 |
| APT1 | CTATGCCTTCATGGTTTGATA | SEQ ID NO: 2 |
| APT1 | CAGGAAATGATGGATGTCAA | SEQ ID NO: 3 |
| APT2 | GGCTGCTTTCTTATCCATTTC | SEQ ID NO: 4 |
| APT2 | GCAGCTGTGAAGGAATTTCTT | SEQ ID NO: 5 |

For experiments, the appropriate shRNA clones (50 ng/µL) were pooled. The pLKO.1 vector was used as a control shRNA in comparison to shRNAs for the targets of interest. 120,000 HEK293T cells/well were plated in 500 µL DMEM glutamax (10% FBS) into two wells of a four well chambered imaging dish (D35C4-20-1.5-N, Cellvis, Mountain View, Calif., United States of America) which were precoated with 4 µg Poly-D-lysine (30-70 KDa, Alfa Aesar, Haverhill, Mass., United States of America) for 2 h at room temperature or overnight at 4° C. After 18-20 h, the media was replaced by fresh 500 µL DMEM glutamax (10% FBS) and the cells were transfected with 600 ng control/APT1/APT2 shRNAs following manufacture's conditions. Briefly, 26.2 µL of opti-MEM containing 1.8 µL of Lipofectamine 3000 was added to mix of 13.6 µL opti-MEM, 1.2 µL P3000 and 12 µL shRNAs mix (50 ng/µL), and resulting DNA:Lipofectamine mix was incubated at room temperature for 15 min. After incubation 52 µL of the DNA:Lipofectamine mix was added to the corresponding well of the four well chambered imaging dish. After 32-35 h the media was replaced with 100 nM MitoTracker Deep red in 500 µL serum-free DMEM. After 30 min of incubation at 37° C., the cells were washed with 500 µL of Live Cell Imaging Solution and replaced by 1 µM RDP-2 in Live Cell Imaging Solution. After incubation for 10 min at 37° C. and 5% $CO_2$, the cells were washed with 500 µL Live Cell Imaging Solution and 500 µL of Live Cell Imaging Solution and images were obtained on an inverted epi-fluorescence microscope (Olympus IX83; Olympus Corporation, Tokyo, Japan, United States of America) attached with EMCCD camera (Photometrics EVOLVE™ Delta, Photometrics, Tucson, Ariz., United States of America) with 40× oil objective (N/A 1.3) for RDP-2 (excitation filter 1 430/24 nm, dichroic chroma 89007, emission filter 1 470/24 nm, exposure time 60 ms, EM gain 30, excitation filter 2 480/20 nm, dichroic chroma 49014, emission filter 2 575/40 nm, exposure time 50 ms, EM gain 30), brightfield (exposure time 50 ms, EM gain 30), and MitoTracker Deep Red: (excitation filter 640/30 nm, emission filter 705/72 nm, dichroic chroma 89016, exposure time 15 ms, EM gain 15). Analyses were performed in ImageJ (Wayne Rasband, NIH). Each experiment was repeated in at least three biological replicates with identical results.

Quantification and Display of Fluorescence Images of RDP-1 and RDP-2 for Cultured Cells.

The probe channel data were expressed as a ratio of the blue channel divided by the green channel and normalized to the average fluorescence intensity of the control conditions. To eliminate errors from autofluorescence, the images were thresholded using the bluer channel images at the same minimum level that included the maximum number of cells in focus (as determined visually by the mitochondrial dye) while limiting the signal from areas where cells are not present. The average value of all nonzero pixels from the blue channel:green channel ratio image were calculated in ImageJ for three different measurements from each experiment. The percent deprotected was estimated by imaging RDP-1/2 in buffer (20 mM HEPES, 150 mM NaCl, 0.1% Triton X-100, pH 7.4, 0.1% DMSO) and for dye deprotected with 20 mM DTT in buffer (20 mM HEPES, 150 mM NaCl, 0.1% Triton X-100, pH 7.4, 0.1% DMSO) for 1 h at room temperature before aliquoted into individual tubes and stored at −80° C. A fresh aliquot of the solution was thawed for each experiment and diluted to 250 nM (RDP-1) or 500 nM (RDP-2) in buffer (20 mM HEPES, 150 mM NaCl, 0.1% Triton X-100, pH 7.4, 10 mM DTT) and allowed to equilibrate for 30 m before being imaged. The resulting images were divided in the same manner as above and the average ratio was taken from at least three images in a circle with a diameter of 150 pixels drawn at the center of the image. The ratios obtained from deprotected and protected dyes were interpreted to be the ratio at 100% and 0%, respectively, and fit by linear least squares. The resulting equation for the line was used to estimate the percent deacylation of the dye.

Epifluorescent Imaging of RDP-2 with Human Colon Organoids.

At least 24 h before imaging experiments, cultured colon organoids were split using a 25G needle and 1 mL syringe, pelleted, and 50-100 organoids per well were re-plated in eight-well chambered slides (20 µL droplets/well; 250 µL organoid growth media; Cellvis, Mountain View, Calif., United States of America) for treatment and imaging. 30 min before the addition of RDP-2, the cell culture media was removed and cells were washed with 300 µL of serum-free FluoroBrite DMEM (Gibco, Gaithersburg, Md., United States of America; High Glucose, Glutamax, no FBS). The media was then replaced with 300 µL of serum-free FluoroBrite DMEM containing 0.2% DMSO carrier as a control, Palm B, or ML348 incubated for 30 min at 37° C. and 5% $CO_2$. The media was removed, the cells were washed with 300 µL of Live Cell Imaging Solution (Thermo Fisher Scientific, Waltham, Mass., United States of America), and 300 µL of 5 µM RDP-2 along with the appropriate inhibitor or DMSO as control in Live Cell Imaging Solution was added to each well. After incubation for 10 min at 37° C. and 5% $CO_2$, the cells were washed with 300 µL Live Cell Imaging Solution and 300 µL of Live Cell Imaging Solution containing DMSO or the appropriate inhibitor was added to the cells immediately before images were obtained on an inverted epi-fluorescence microscope (Olympus IX83; Olympus Corporation, Tokyo, Japan) attached with EMCCD camera (Photometrics EVOLVE™ Delta, Photometrics, Tucson, Ariz., United States of America) with 40× oil objective (N/A 1.3) for RDP-2 (excitation filter 1 430/24 nm, dichroic chroma 89007, emission filter 1 470/24 nm, exposure time 150 ms, EM gain 100, excitation filter 2 480/20 nm, dichroic chroma 49014, emission filter 2 575/40 nm, exposure time 75 ms, EM gain 75), brightfield (exposure time 50 ms, EM gain 30). Analyses were performed in ImageJ. Each experiment was repeated at least three separate times with identical results. Images were quantified and displayed in a similar manner to the cell culture experiments except that ROIs were manually selected for the tissue portion in focus with out setting a threshold.

Fluorescence Imaging of RDP-1 with HEPG2 Cells.

HEPG2 were plated with 500 mL of DMEM (Gibco, Gaithersburg, Md., United States of America; High Glucose, Glutamax, 10% FBS) a four well chambered imaging dish (D35C4-20-1.5-N, Cellvis, Mountain View, Calif., United States of America) which were precoated with 4 µg Poly- D-lysine (30-70 KDa, Alfa Aesar, Haverhill, Mass., United States of America) for 2 h at room temperature or overnight at 4° C. and grown to ca. 80% confluence prior to imaging. 30 min before the addition of the RDP, the cell culture media was removed and cells were washed with 500 μL of serum-free DMEM (Gibco, Gaithersburg, Md., United States of America; High Glucose, Glutamax, no FBS). The media was then replaced with 500 μL of serum-free DMEM containing 100 nM Mitotracker Deep Red (Thermo Fisher Scientific, Waltham, Mass., United States of America) to assist in focusing and processing) and either 0.1% DMSO carrier as a control or Palm B in DMSO and incubated for 30 min at 37° C. and 5% $CO_2$. The media was removed, the cells were washed with 500 μL of Live Cell Imaging Solution (Thermo Fisher Scientific, Waltham, Mass., United States of America), and 500 μL of 1 μM RDP-1 along with the Palm B or DMSO as control in Live Cell Imaging Solution was added to each well. After incubation for 10 min at 37° C. and 5% $CO_2$, the cells were washed with 500 μL Live Cell Imaging Solution and 500 μL of Live Cell Imaging Solution containing DMSO or the appropriate inhibitor was added to the cells immediately before images were obtained on an inverted epi-fluorescence microscope (Olympus IX83; Olympus Corporation, Tokyo, Japan) attached with EMCCD camera (Photometrics EVOLVE™ Delta, Photometrics, Tucson, Ariz., United States of America) with 40× oil objective (N/A 1.3; excitation filter 1 430/24 nm, dichroic chroma 89007, emission filter 1 470/24 nm, exposure time 80 ms, EM gain 60, excitation filter 2 480/20 nm, dichroic chroma 49014, emission filter 2 575/40 nm, exposure time 50 ms, EM gain 30) Analyses were performed in ImageJ. Each experiment was repeated at least three separate times with identical results.

Preparation of Palmitate Solution.

A stock solution of 5 mM sodium palmitate in 5% BSA (fatty acid free, Sigma, St. Louis, Mo., United States of America) in DMEM (Gibco, Gaithersburg, Md., United States of America; High Glucose, Glutamax, no FBS) was prepared by dissolving BSA in DMEM and sodium palmitate was added. The resulting suspension was sonicated for 30 mins and then incubated at 37° C. for 24 h. The now clear solution was then briefly mixed on a vortex mixture and filtered through a 0.22 μm syringe filter (PVDF, 30 mm diameter, Santa Cruz Biotechnology, Dallas, Tex., United States of America). The resulting solution was alloquoted and stored at −20° C. Solutions containing only 5% BSA were prepared in the same way as a control. Solutions were thawed immediately before use and dilution to the required concentration in DMEM (Gibco, Gaitherburg, Md., United States of America; High Glucose, Glutamax, no FBS).

Fluorescence Imaging of Lipid Metabolism in HEPG2 Cells with RDP-1.

HEPG2 were plated with 500 mL of DMEM (Gibco, Gaithersburg, Md., United States of America, High Glucose, Glutamax, 10% FBS) a four well chambered imaging dish (D35C4-20-1.5-N, Cellvis, Mountain View, Calif., United States of America) which were precoated with 4 μg Poly-D-lysine (30-70 KDa, Alfa Aesar, Haverhill, Mass., United States of America) for 2 h at room temperature or overnight at 4° C. and grown to ca. 70% confluence prior to serum starvation overnight (DMEM, Gibco, Gaithersburg, Md., United States of America; High Glucose, Glutamax, no FBS). 6 h before the experiment, media was replaced with DMEM (Gibco, Gaithersburg, Md., United States of America; High Glucose, Glutamax, no FBS) with 1% BSA (fatty acid free, Sigma, St. Louis, Mo., United States of America) with 1 mM sodium palmitate or with out as a control. After 6 h, the cell culture media was removed and cells were washed with 500 μL of serum-free DMEM (Gibco, Gaithersburg, Md., United States of America; High Glucose, Glutamax, no FBS). The media was then replaced with 500 μL of serum-free DMEM containing 100 nM Mitotracker Deep Red (Thermo Fisher Scientific, Waltham, Mass., United States of America; to assist in focusing and processing) and incubated for 30 min at 37° C. and 5% $CO_2$. The media was removed, the cells were washed with 500 μL of Live Cell Imaging Solution (Thermo Fisher Scientific, Waltham, Mass., United States of America), and 500 μL of 1 μM RDP-1 in Live Cell Imaging Solution was added to each well. After incubation for 10 min at 37° C. and 5% $CO_2$, the cells were washed with 500 μL Live Cell Imaging Solution and 500 μL of Live Cell Imaging Solution containing DMSO or the appropriate inhibitor was added to the cells immediately before images were obtained on an inverted epi-fluorescence microscope (Olympus IX83; Olympus Corporation, Tokyo, Japan) attached with EMCCD camera (Photometrics EVOLVE™ Delta, Photometrics, Tucson, Ariz., United States of America) with 40× oil objective (N/A 1.3; excitation filter 1 430/24 nm, dichroic chroma 89007, emission filter 1 470/24 nm, exposure time 80 ms, EM gain 60, excitation filter 2 480/20 nm, dichroic chroma 49014, emission filter 2 575/40 nm, exposure time 50 ms, EM gain 30). Analyses were performed in ImageJ as described above. Each experiment was repeated at least three separate times with identical results.

Example 8

Synthesis of RDP-1

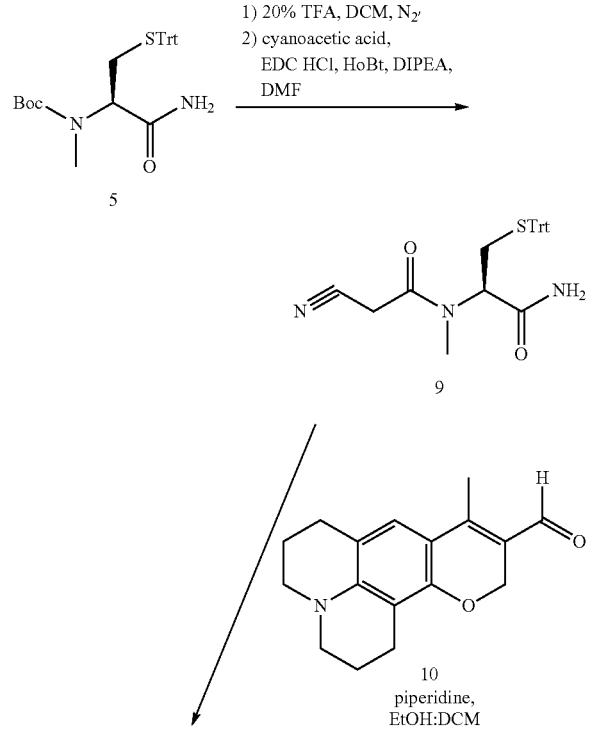

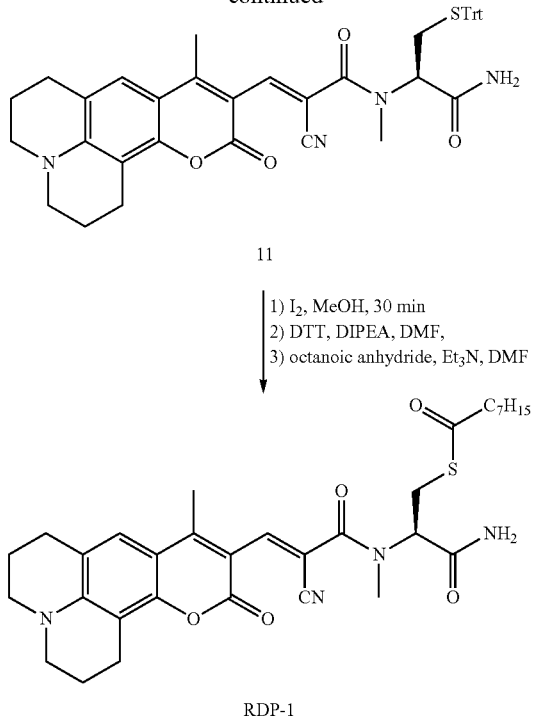

RDP-1 was prepared as shown above in Scheme 4, starting from compound 5 described above in Example 2.

((2R)-2-(2-cyano-N-methylacetamido)-N-methyl-3-[(triphenylmethyl)-sulfanyl]propanamide) (9). In a vial sealed with a rubber septa and equipped with a stir bar, 5 (0.2542 g, 0.5 mmol) was dissolved in 5 mL CH$_2$Cl$_2$ and placed under a nitrogen atmosphere. Trifluoroacetic acid was slowly added until the concentration was ca. 20% v/v and allowed to stir for 1 h. After complete boc-deprotection as determined by LC-MS, the mixture was concentrated and then redissolved in CH$_2$Cl$_2$ (50 mL) and washed with sat. bicarbonate (50 mL). The organic layer was dried over sodium sulfate, filtered, and concentrated in a round bottom flask. A stirbar, cyanoacetic acid (0.1322 g, 1.5 mmol), EDC.HCl (0.9935 g, 5.2 mmol), and hoBt (0.2381 g, 1.5 mmol) were added to the flask, sealed with a rubber septa, and placed under a flow of nitrogen. The flask was then cooled to 0° C. in an ice bath before adding DMF ca. 15 mL and DIPEA (0.27 mL, 1.5 mmol). The reaction mixture was allowed to slowly warm to room temperature and react overnight. The following day, the reaction was diluted with brine (50 mL) and extracted into EtOAc (3×75 mL). The organic layers were combined, dried over sodium sulfate, filtered, and concentrated. Purification by flash column chromatography (gradient of 0% to 100% EtOAc in Hexanes) yielded 9 with quantitative yield. R$_f$ (70% EtOAc in Hexanes)=0.39. $^1$H-NMR (500 MHz; CDCl$_3$) b: 7.42 (d, J=10, 6H), 7.30 (t, J=10, 6H), 7.23 (t, J=10, 3H), 5.71 (s, 1H), 4.50 (m, 1H), 3.47 (s, 2H), 2.77 (m 4H), 2.68 (m, 3H), 2.65 (m, 1H). $^{13}$C-NMR (126 MHz; CDCl$_3$) b: 168.8, 144.3, 129.6, 129.5, 128.4, 128.2, 127.3, 127.0, 67.2, 56.4, 29.9, 26.3, 25.7. HRA-MS(+) Calculated for C$_{27}$H$_{27}$N$_3$O$_2$S [M$^+$] 457.1824; found 457.1839.

Synthesis of 10 (6-methyl-4-oxo-3-oxa-13-azatetracyclo[7.7.1.0$^{2,7}$.0$^{13,17}$]heptadeca-1,5,7,9(17)-tetraene-5-carbalde-hyde) (10). A previously-reported procedure was adapted for the synthesis of 10. See Rooker and Buccella (2015) ChemSci 6, 6456-6461. To a flame-dried vial equipped with a stirbar, 2,3,6,7-Tetrahydro-9-methyl-1H, 5H-quinolizino[9,1-gh]coumarin (see Park et al. (2009) Dyes Pigments 82, 258-267) (0.6064 g, 2.4 mmol) was dissolved in a minimal amount of dry DMF (ca. 4 mL) under a nitrogen atmosphere. POCl$_3$ (6.8 mmol, 0.63 mL) was added dropwise over 5 min. The resulting solution was allowed to stir for 1 h until complete by LC-MS. The reaction was then quenched by dilution with 5 mL CH$_2$Cl$_2$, followed by sat. bicarbonate solution until gas evolution ceased. The resulting mixture was diluted with 50 mL brine extracted into CH$_2$Cl$_2$ (3×100 mL). The organic layer was dried over sodium sulfate, filtered, and concentrated. Purification by flash column chromatography (gradient of 0% to 5% MeOH in CH$_2$Cl$_2$) yielded 10 (0.544 g, 80.8%) as an orange solid in 80.8% yield. R$_f$ (5% MeOH in DCM)=0.50. $^1$H-NMR (500 MHz; CDCl$_3$) b: 10.37 (s, 1H), 7.24 (s, 1H), 3.34 (m, 4H), 2.88 (t, J=10 Hz, 2H), 2.78 (m, 5H), 1.98 (m, 4H). $^{13}$C-NMR (126 MHz; CDCl$_3$) δ: 191.6, 163.3, 159.3, 152.3, 148.6, 124.6, 119.4, 111.5, 109.1, 106.0, 50.3, 49.9, 27.8, 21.3, 20.3, 20.2, 14.9. HRA-MS(+) Calculated for C$_{17}$H$_{17}$NO$_3$ [M$^+$]283.1208; found 283.1243.

Synthesis of ((2E)-2-cyano-N-methyl-3-{6-methyl-4-oxo-3-oxa-13-azatetracyclo[7.7.1.0$^{2,7}$.0$^{13,17}$]heptadeca-1,5,7,9(17)-tetraen-5-yl}-N-[(1R)-1-(methylcarbamoyl)-2-[(triphenylmethyl)sulfanyl]ethyl]prop-2-enamide) (11). In a flame-dried vial equipped with a stir bar, 10 (0.1140 g, 0.4 mmol) and 2 (0.1843 g, 0.4 mmol) were dissolved in 10 mL 9:1 dry CH$_2$Cl$_2$:dry EtOH followed by two drops of piperdine. The vial was then capped and allowed to stir at room temperature for 72 h. When complete as determined by LC-MS, the reaction mixture was concentrated and purified by flash column chromatography (gradient of 0% to 10% MeOH in CH$_2$Cl$_2$) to yield a mixture of both the Z and E isomers of 11 (0.127 g, 99.6%) as a red solid, which were used without further purification. R$_f$ (10% MeOH in CH$_2$Cl$_2$)=0.67. $^1$H-NMR (500 MHz, [CD$_3$]$_2$CO): 7.63 (s, 1H), 7.46 (d, J=10 Hz, 6H), 7.37 (s, 1H), 7.34 (t, J=10 Hz, 6H), 7.25 (m, 3H), 4.73 (m, 1H), 3.38 (m, 6H), 2.94 (m, 4H), 2.80 (m, 4H), 2.69 (d, J=5 Hz, 3H), 2.56 (s, 3H), 1.96 (m, 4H). $^{13}$C-NMR (126 MHz; CDCl$_3$) b: 191.2, 168.9, 164.6, 159.8, 154.4, 150.6, 147.7, 144.6, 143.6, 129.5, 127.8, 126.5, 123.3, 119.4, 116.9, 110.3, 109.8, 108.8, 108.5, 105.6, 105.4, 66.6, 50.0, 49.5, 29.9, 27.6, 26.2, 21.0 (Extra peaks present likely due to mixture of Z and E isomers). HRA-MS(+) Calculated for C$_{44}$H$_{42}$N$_4$O$_4$S [M$^+$] 722.2927; found 722.2934.

Synthesis of RDP-1 ((2E)-2-cyano-N-methyl-3-{6-methyl-4-oxo-3-oxa-13-azatetracyclo[7.7.1.0$^{2,7}$.0$^{13,17}$]heptadeca-1,5,7,9(17)-tetraen-5-yl}-N-[(1R)-1-(methylcarbamoyl)-2-(octanoyl sulfanyl)ethyl]prop-2-enamide). In a vial, 11 (0.1272 g, 0.1 mmol) was dissolved in 3 mL of MeOH, followed by addition of iodine (0.0370 g, 0.2 mmol). The solution was stirred for 30 min before quenching with a 10 mL solution containing 0.2 M sodium citrate and 0.2 M sodium ascorbate in H$_2$O at pH 4.0. The resulting mixture was extracted into CH$_2$Cl$_2$ (3×30 mL). The organic layers were combined, dried over sodium sulfate, filtered, concentrated, semi-purified by flash column chromatography (gradient of 0% to 10% MeOH in CH$_2$Cl$_2$), and used without further purification. The resultant red residue was dissolved in 3 mL dry DMF in a vial under a nitrogen atmosphere, to which DTT (0.0472 g, 0.4 mmol) and then 0.05 mL of DIPEA (0.4 mmol) were added, after which the red solution turned yellow. After 5 min, product formation was confirmed by LC-MS and the solution was diluted with 1 M HCl (10 mL) and extracted into EtOAc (3×20 mL). The organic layers were combined, dried over sodium sulfate, filtered, and concentrated. The resulting orange-yellow oil was dissolved in 3 mL DMF and octanoic anhydride (0.72 mL, 2.4 mmol) was added immediately followed by the dropwise addition of DIPEA (0.42 mL, 2.4 mmol). After 30 min, the red solution was diluted with 30 mL brine and extracted into $CH_2Cl_2$ (3×30 mL). The organic layers were combined, dried over sodium sulfate, filtered, concentrated, and purified by flash column chromatography (first column gradient of 0% to 100% $CH_2Cl_2$ in hex to 10% MeOH in $CH_2Cl_2$, second column 0% to 100% EtOAc in hex) to yield RDP-1 as a red solid (0.0332 g, 44.7%). $R_f$ (5% MeOH in $CH_2Cl_2$)=0.47. $^1$H-NMR (500 MHz, $[CD_3]_2CO$): 7.70 (s, 1H), 7.29 (s, 1H), 5.11 (s, 1H), 4.97 (s, 1H), 3.36 (m, 6H), 3.30 (s, 1H), 3.07 (s, 1H), 2.78 (m, 10H), 2.59 (t, J=5 Hz), 2.54 (m, 2H), 2.47 (s, 3H), 1.97 (m, 7H), 1.62 (m, 4H) HRA-MS(+) Calculated for $C_{33}H_{42}N_4O_5S$ [M$^+$] 606.2876; found 606.2874. Purity ascertained by LC-MS.

Example 9

Synthesis of RDP-2

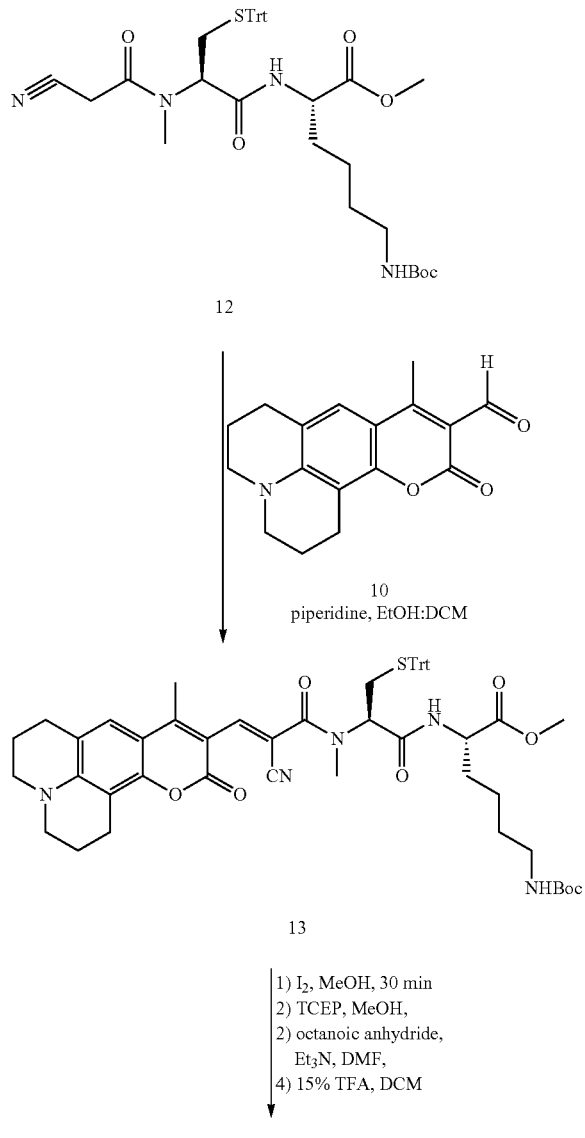

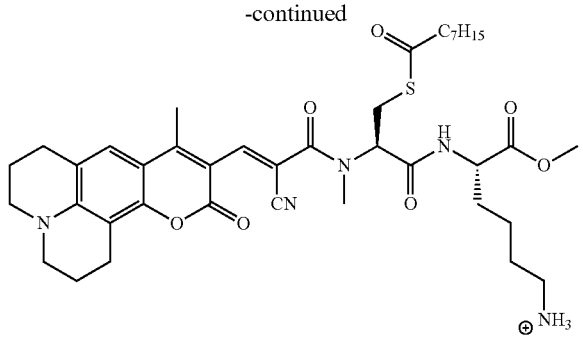

RDP-2

RDP-2 was prepared as shown above in Scheme 5 from compound 12. which was synthesized from compound 5 of Example 2.

Synthesis of 6 (methyl (2S)-6-{[(tert-butoxy)carbonyl]amino}-2-[(2R)-2-(2-cyano-N-methylacetamido)-3-[(triphenylmethyl)sulfanyl]propanamido]-hexanoate) (12). In a vial sealed with a rubber septa and equipped with a stir bar, 5 (2.0000 g, 4.2 mmol) was dissolved in 10 mL $CH_2Cl_2$ and placed under a nitrogen atmosphere. Trifluoroacetic acid was slowly added until the concentration was ca. 20% v/v and allowed to stir for 1 h. After complete boc-deprotection as determined by LC-MS, the mixture was concentrated and then dissolved in $CH_2Cl_2$ (50 mL) and dried by rotary evaporation. Dissolving and drying was then repeated two additional times. After the last time, the vial was dried in vacuo and in a separate flame dried flask sealed with a septa and under nitrogen atmosphere cyanoacetic acid (1.8026 g, 21.2 mmol) and EDC.HCl (1.0156 g, 5.3 mmol) were dissolved in dry DMF (15 mL). After 1 h, 1.0000 g (2.6 mmol) of the boc-deprotected cysteine was added to the mixture of EDC and cyanoacetic acid followed by the addition of DIPEA (0.92 mL, 5.3 mmol). The resulting solution was then stirred at room temperature (rt) for 48 h before being diluted with brine (100 mL) and extracted into $CH_2Cl_2$ (3×100 mL). The organic layers were combined, dried over sodium sulfate, filtered, concentrated, and purified by flash column chromatography (0% to 10% MeOH in 1:1 EtOAc:$CH_2Cl_2$) and used without further purification. $R_f$ (10% MeOH in $CH_2Cl_2$)=0.38. Under a nitrogen atmosphere in a flame dried vial sealed with a septa equipped with a stir bar, 1.0000 g of the resulting oil, (2.2 mmol), $NH_2$-Lys(Boc)-OMe.HCl (1.0014 g, 3.3 mmol), EDC.HCl (4.3122 g, 22.5 mmol), and hoBt (1.0334 g, 6.7 mmol) were cooled down to 0° C. in an ice bath before the addition of DMF (40 mL) and DIPEA (1.2 mL, 6.7 mmol). After 5 minutes of stirring at 0° C. the solution was allowed to warm up to rt. After 3 h, when complete as determined by LC-MS, the solution was diluted with brine (100 mL) and extracted into EtOAc (3×100 mL). The organic layers were combined, dried over sodium sulfate, filtered, concentrated, and purified by flash column chromatography (0% to 10% MeOH in $CH_2Cl_2$, 2×) to yield 12 (0.3770 g, 24.4%). $R_f$ (50% EtOAc in hexanes)=0.33. $^1$H-NMR (500 MHz, CDCl$_3$): 7.42 (m, 6H), 7.30 (m, 6H), 7.22 (m, 3H), 6.87 (s, 1H), 4.56 (m, 5H), 4.39 (m, 1H), 3.76 (s, 5H), 3.69 (s, 2H), 3.44 (s, 3H), 3.10 (m, 3H), 2.78 (s, 2H), 1.41 (s, 9H). $^{13}$C-NMR (126 MHz; CDCl$_3$) b: 172.2, 172.1, 161.7, 156.3, 144.2, 129.5, 129.4, 128.3, 128.1, 127.2, 126.9, 114.6, 79.2, 67.1, 56.4, 52.8, 52.6, 52.4, 52.1, 29.5, 28.4, 25.8 HRA-MS(+) Calculated for $C_{38}H_{46}N_4O_6S$ [M$^+$] 686.3138; found 686.3142.

Synthesis of 7 (methyl (2S)-6-{[(tert-butoxy)carbonyl]amino}-2-[(2R)-2-[(2E)-2-cyano-N-methyl-3-{6-methyl-4-oxo-3-oxa-13-azatetra-cyclo-[7.7.1.0$^{2,7}$.0$^{13,17}$]heptadeca-1,5,7,9(17)-tetraen-5-yl}prop-2-enamido]-3-[(triphenylmethyl)sulfanyl]propanamido]hexanoate) (13). In a flame-dried vial equipped with a stir bar, 12 (0.2426 g, 0.4 mmol) and 10 (0.1000 g, 0.4 mmol) were dissolved in 10 mL 9:1 dry CH$_2$Cl$_2$:dry EtOH followed by two drops of piperdine. The vial was then capped and allowed to stir at room temperature. After 48 h, an addition 0.1000 g of 10 (0.4 mmol) was added and it was allowed to stir for 48 h longer. When complete as determined by LC-MS, the reaction mixture was concentrated and purified by flash column chromatography (First column gradient of 0% to 30% EtOAc in CH$_2$Cl$_2$, second column gradient of 0% to 100% EtOAc in Hexanes) to yield a mixture of both the Z and E isomers of 13 (0.0710 g, 21.1%) as a red solid, which were used without further purification. R$_f$ (50% EtOAc in hexanes)=0.28. $^1$H-NMR (500 MHz, [CD$_3$]$_2$CO): 7.63 (s, 1H), 7.46 (m, 6H), 7.38 (s, 1H), 7.33 (m, 6H), 7.24 (m, 3H), 4.96 (m, 1H), 4.78 (s, 2H), 4.34 (m, 2H), 4.24 (m, 1H), 3.68 (m, 1H), 3.62 (s, 1H), 3.38 (m, 2H), 3.30 (m, 1H), 2.99 (m, 4H), 2.81 (m, 3H), 2.77 (m, 1H), 2.57 (m, 1H), 2.52 (m, 1H), 2.45 (m, 1H), 1.96 (m, 6H), 1.50 (m, 3H), 1.40 (m, 3H), 1.34 (m, 9H), 1.29 (m, 1H) $^{13}$C-NMR (126 MHz; [CD$_3$]$_2$CO) b: 173.0947, 169.116, 165.3539, 160.8237, 155.8995, 151.5859, 151.4283, 148.6708, 148.1291, 145.6671, 144.6527, 130.3529, 128.8953, 128.787, 127.7135, 127.5264, 124.5226, 120.5734, 117.7371, 111.9364, 111.2766, 110.8531, 109.238, 109.1001, 106.1259, 78.2747, 67.2249, 53.9198, 52.1372, 50.6403, 50.0986, 40.7131, 31.2981, 30.9337, 28.6489, 28.2352, 24.1974, 22.0012, 21.8831, 20.849, 20.6717, 15.649 (extra peaks present likely due to mixture of Z and E isomers). HRA-MS(+) Calculated for C$_{55}$H$_{61}$N$_5$O$_8$S [M$^+$] 951.4241; found 951.4222.

Synthesis of RDP-2 ((5S)-5-[(2R)-2-[(2E)-2-cyano-N-methyl-3-{6-methyl-4-oxo-3-oxa-13-azatetracyclo[7.7.1.0$^{2,7}$.0$^{13,17}$]heptadeca-1,5,7,9(17)-tetraen-5-yl}prop-2-enamido]-3-(octanoylsulfanyl)propanamido]-6-methoxy-6-oxohexan-1-aminium). Iodine (0.0379 g, 0.02 mmol) was added in one portion to a mixture of 13 (0.0710 g, 0.01 mmol) and 1 mL MeOH in a vial equipped with a stirbar. After 30 mins, the solution was quenched with a solution of 0.2 M sodium citrate and 0.2 M sodium ascorbate in water at pH 4.0 (5 mL) and extracted into CH$_2$Cl$_2$ (3×15 mL). The organic layers were combined, dried over sodium sulfate, filtered, and concentrated before redissolving in MeOH (1 mL) and a solution of (tris(2-carboxyethyl)phosphine (0.4278 g, 1.5 mmol) in MeOH 1 mL and 0.5 mL water was added. After 2 h, the reaction mixture was concentrated in vacuo and dissolved in 1 mL DMF. Octanoic anhydride (0.22 mL, 0.75 mmol) was then added followed by trimethylamine dropwise over 10 mins (0.10 mL, 0.75 mmol). After 30 mins, the solution was diluted with brine (5 mL) and the pH was adjusted to 8 with 1 M NaOH before extracting into CH$_2$Cl$_2$ (3×10 mL). The organic layers were combined, dried over sodium sulfate, filtered, concentrated, and purified by flash column chromatography (first column gradient of 0% to 20% MeOH in CH$_2$Cl$_2$, second column gradient of 0% to 100% EtOAc in hexanes, third column gradient of 0% to 5% MeOH in CH$_2$Cl$_2$) R$_f$ (5% MeOH in CH$_2$Cl$_2$)=0.38. HRA-MS(+) Calculated for C$_{44}$H$_{61}$N$_5$O$_9$S [M+] 835.4190; found 835.4197. The resulting oil was then dissolved in 0.5 mL DCM containing 15% v/v TFA and stirred for 30 min at room temperature. The solution was then concentrated and purified by flash column chromatography (first column gradient of 0% to 20% MeOH in CH$_2$Cl$_2$, second column gradient of 0% to 10% MeOH in CH$_2$Cl$_2$) yielding 0.0042 g (6.3%) of red oil. R$_f$ (5% MeOH in CH$_2$Cl$_2$)=0.50. HRA-MS(+) Calculated for C$_{39}$H$_{54}$N$_5$O$_7$S [M+] 736.3744; found 736.3807. Purity ascertained by LC-MS.

Example 10

Photophysical Properties of RDPs

Figure 19A:
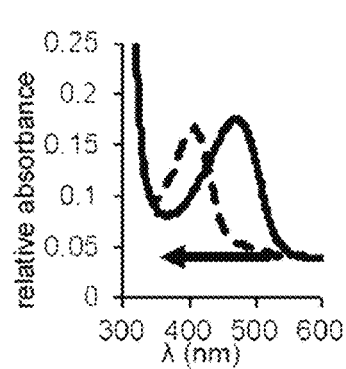
FIG. 19A is a graph showing the ultraviolet-visible (UV-Vis) absorption spectra of ratiometric depalmitoylation probe 1 (RDP-1; 15 micromolar (μM), solid line) and of its deacylated form (dotted line) at pH 7.4.
Figure 19B:
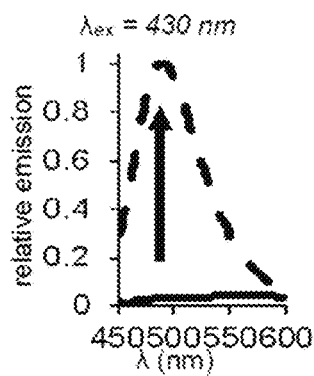
FIG. 19B is a graph showing the fluorescence emission spectra of ratiometric depalmitoylation probe 1 (RDP-1; 5 micromolar (μM), solid line) and of its deacylated form (dotted line) at pH 7.4 at an excitation wavelength ($\lambda_{ex}$) of 430 nanometers (nm).
Figure 19C:
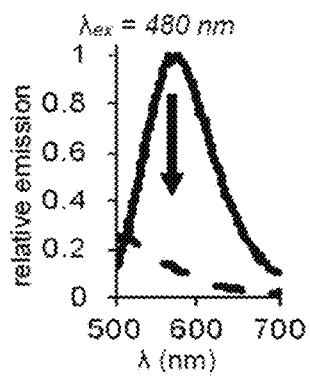
FIG. 19C is a graph showing the fluorescence emission spectra of ratiometric depalmitoylation probe 1 (RDP-1, 15 micromolar (μM), solid line) and of its deacylated form (dotted line) at pH 7.4 at an excitation wavelength ($\lambda_{ex}$) of 480 nanometers (nm).
Figure 19D:
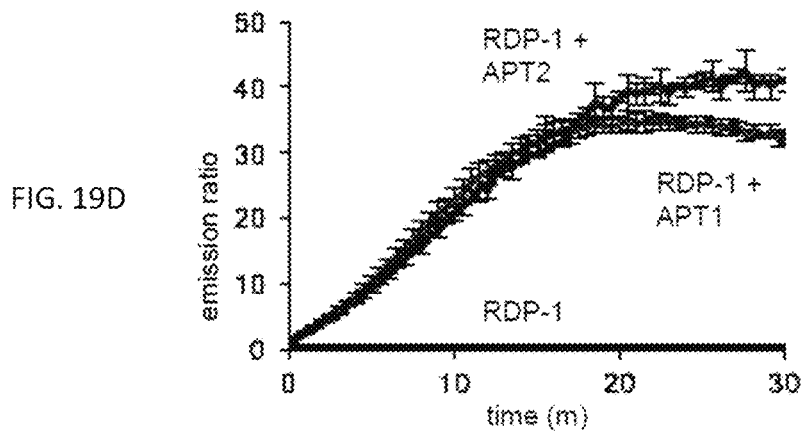
FIG. 19D is a graph showing the ratiometric response of 1 micromolar (μM) ratiometric depalmitoylation probe-1 (RDP-1) to 200 nanomolar (nM) acyl protein thioesterase 1 (APT1) or 200 nM acyl protein thioesterase 2 (APT2). Data is shown as the ratio of the emission of RDP-1 divided by the emission of its deacylated form. Error bars are ±standard deviation. For comparison the response of RDP-1 with no enzyme is also shown.
Figure 21A:
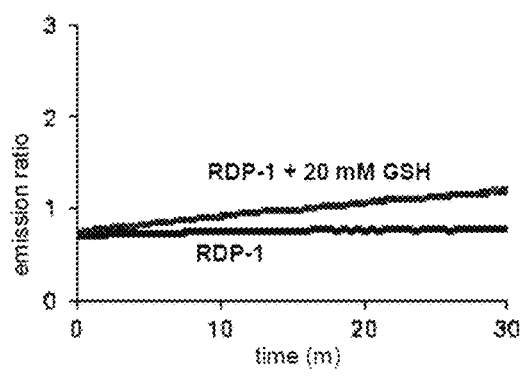
FIG. 21A is a graph showing the response of 1 micromolar (μM) ratiometric depalmitoylation probe 1 (RDP-1) to 20 millimolar (mM) glutathione (GSH) in pH 7.4 buffer. Data is also shown for RDP-1 in the absence of GSH. Error bars are ±standard deviation (n=3).
Figure 21B:
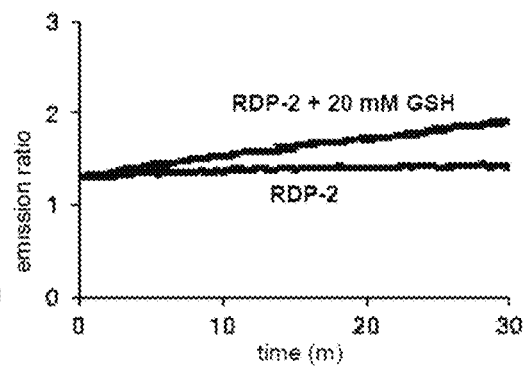
FIG. 21B is a graph showing the response of 1 micromolar (μM) ratiometric depalmitoylation probe 2 (RDP-2) to 20 millimolar (mM) glutathione (GSH) in pH 7.4 buffer. Data is also shown for RDP-2 in the absence of GSH. Error bars are ±standard deviation (n=3).

The photophysical properties of RDP-1 and RDP-2 were tested in vitro. RDP-1 and RDP-2 have absorbance maxima at 470 nm and 473 nm, respectively. See FIGS. 19A and 20A. Upon deacylation, the absorbance maxima dramatically shift to 406 nm and 407 nm, respectively, indicating that the Michael addition is occurring as designed. See FIG. 2. Illumination with either 430 or 480 nm light permits selective excitation of the two forms of the probe, with the fluorescence emission upon 430 nm excitation increasing upon deacylation (see FIG. 19B for RDP-1) and the fluorescence emission upon 480 nm excitation decreasing upon deacylation. See FIG. 19C for RDP-1. These ratiometric fluorescence responses were used to monitor enzymatic activity of RDP-1 and RDP-2 with purified human APT1 and APT2, incubation 1 μM probe with 200 nM enzyme results in a rapid change in the ratiometric response, with a ratio change from 0.7 to 34 for RDP-1 (see FIG. 19D) and 1.9 to 16 for RDP-2 after just 20 min. See FIG. 20B. Neither RDP-1 nor RDP-2 responds to catalytically inactive APTs or 20 mM glutathione. See FIGS. 21A and 21B.

Example 11

Measurement of APT Activity in Live Cells with RDPs

Figure 22:
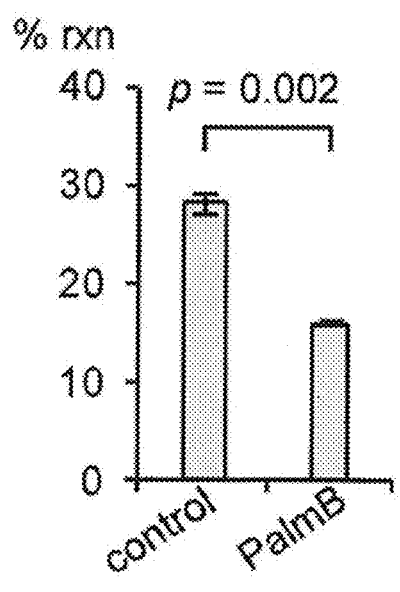
FIG. 22 is a graph showing the quantification of the ratiometric response of ratiometric depalmitoylation probe 1 (RDP-1) in live human embryonic kidney (HEK293T) cells with and without inhibition by palmostatin B (PalmB). The cells were loaded with 1 micromolar (μM) RDP-1 for 10 minutes after treatment with either dimethylsulfoxide (control) or 20 μM PalmB for 30 minutes and then analyzed by fluorescence microscopy. "Blue" fluorescence was measured at an excitation wavelength ($\lambda_{ex}$) of 430 nanometers (nm) and an emission wavelength ($\lambda_{em}$) of 470 nm. "Green" fluorescence was measured at $\lambda_{ex}$ of 480 nm and $\lambda_{em}$ of 575 nm. Ratiometric images were generated by dividing the green channel by the blue channel. p=0.002. Error bars are±standard deviation (n=3).
Figure 23:
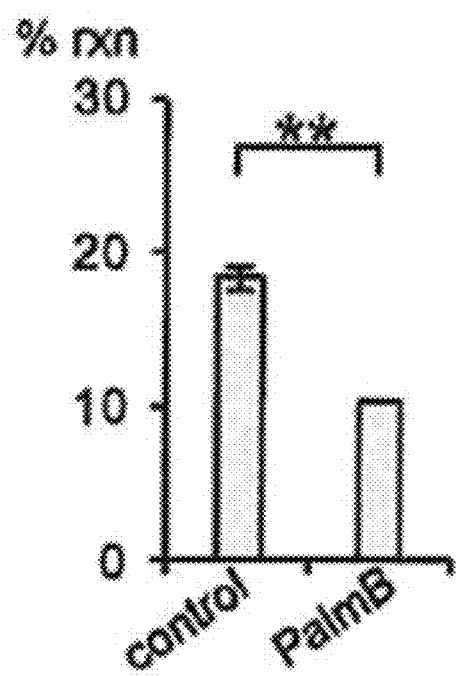
FIG. 23 is a graph showing the quantification of the ratiometric response of ratiometric depalmitoylation probe 2 (RDP-2) in live human embryonic kidney (HEK293T) cells with and without inhibition by palmostatin B (PalmB). The cells were loaded with 1 micromolar (μM) RDP-2 for 10 minutes after treatment with either dimethylsulfoxide (control) or 20 μM PalmB for 30 minutes and then analyzed by fluorescence microscopy. "Blue" fluorescence was measured at an excitation wavelength ($\lambda_{ex}$) of 430 nanometers (nm) and an emission wavelength ($\lambda_{em}$) of 470 nm. "Green" fluorescence was measured at $\lambda_{ex}$ of 480 nm and $\lambda_{em}$ of 575 nm. Ratiometric images were generated by dividing the green channel by the blue channel. **p<0.005. Error bars are±standard deviation (n=3).
Figure 24:
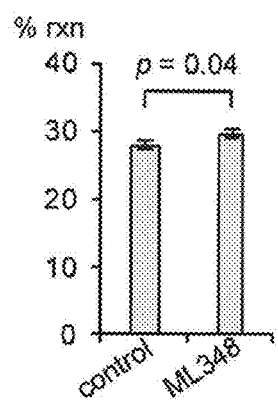
FIG. 24 is a graph showing the quantification of the ratiometric response of ratiometric depalmitoylation probe 1 (RDP-1) in live human embryonic kidney (HEK293T) cells with and without inhibition by acyl protein thioesterase 1 (APT1)-specific inhibitor ML348. The cells were loaded with 1 micromolar (μM) RDP-1 for 10 minutes after treatment with either dimethylsulfoxide (control) or 10 μM ML348 for 30 minutes, and then analyzed by fluorescence microscopy. "Blue" fluorescence was measured at an excitation wavelength ($\lambda_{ex}$) of 430 nanometers (nm) and an emission wavelength ($\lambda_{em}$) of 470 nm. "Green" fluorescence was measured at $\lambda_{ex}$ of 480 nm and $\lambda_{em}$ of 575 nm. Ratiometric images were generated by dividing the green channel by the blue channel. p=0.04. Error bars are ±standard deviation (n=3).
Figure 25:
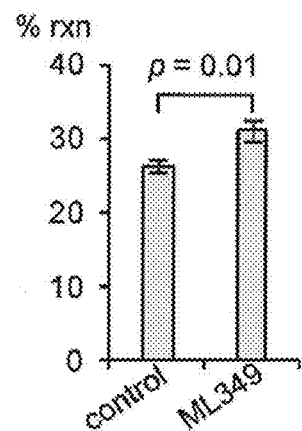
FIG. 25 is a graph showing the quantification of the ratiometric response of ratiometric depalmitoylation probe 1 (RDP-1) in live human embroyonic kidney (HEK293T) cells with and without inhibition by acyl protein thioesterase 2 (APT2)-specific inhibitor ML349. The cells were loaded with 1 micromolar (μM) RDP-1 for 10 minutes after treatment with either dimethylsulfoxide (control) or 10 μM 349 for 30 minutes, and then analyzed by fluorescence microscopy. "Blue" fluorescence was measured at an excitation wavelength ($\lambda_{ex}$) of 430 nanometers (nm) and an emission wavelength ($\lambda_{em}$) of 470 nm. "Green" fluorescence was measured at $\lambda_{ex}$ of 480 nm and $\lambda_{em}$ of 575 nm. Ratiometric images were generated by dividing the green channel by the blue channel. p=0.01. Error bars are ±standard deviation (n=3).
Figure 26A:
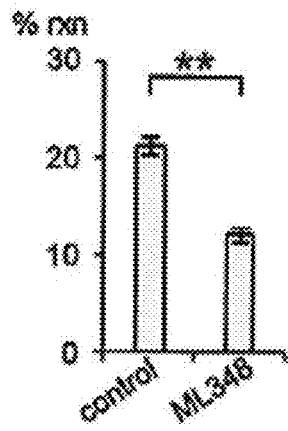
FIG. 26A is a graph showing the quantification of the ratiometric response of ratiometric depalmitoylation probe 2 (RDP-2) in live human embroyonic kidney (HEK293T) cells with and without inhibition by acyl protein thioesterase 1 (APT1)-specific inhibitor ML348. The cells were loaded with 1 micromolar (μM) RDP-2 for 10 minutes after treatment with either dimethylsulfoxide (control) or 5 μM ML348 for 30 minutes, and then analyzed by fluorescence microscopy. "Blue" fluorescence was measured at an excitation wavelength ($\lambda_{ex}$) of 430 nanometers (nm) and an emission wavelength ($\lambda_{em}$) of 470 nm. "Green" fluorescence was measured at $\lambda_{ex}$ of 480 nm and $\lambda_{em}$ of 575 nm. Ratiometric images were generated by dividing the green channel by the blue channel. **p<0.005. Error bars are ±standard deviation (n=3).
Figure 26B:
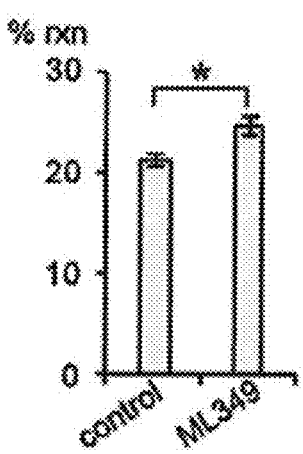
FIG. 26B is a graph showing the quantification of the ratiometric response of ratiometric depalmitoylation probe 2 (RDP-2) in live human embroyonic kidney (HEK293T) cells with and without inhibition by acyl protein thioesterase 2 (APT2)-specific inhibitor ML349. The cells were loaded with 1 micromolar (μM) RDP-2 for 10 minutes after treatment with either dimethylsulfoxide (control) or 5 μM 349 for 30 minutes and then analyzed by fluorescence microscopy. "Blue" fluorescence was measured at an excitation wavelength ($\lambda_{ex}$) of 430 nanometers (nm) and an emission wavelength ($\lambda_{em}$) of 470 nm. "Green" fluorescence was measured at $\lambda_{ex}$ of 480 nm and $\lambda_{em}$ of 575 nm. Ratiometric images were generated by dividing the green channel by the blue channel. *p<0.03. Error bars are ±standard deviation (n=3).

The ability of the RDPs to visualize endogenous S-depalmitoylase activity in living cells was evaluated using fluorescence spectroscopy. Similar to the in vitro ratiometric fluorescence studies, the redder emission (480/20 nm, excitation, 575/40 nm emission) and bluer emission (430/24 nm excitation, 470/24 nm emission) were monitored simultaneously, and the intensities were divided at both wavelengths to generate ratiometric images. The percent deprotected dye was estimated by assuming a linear relationship between the acylated (0%) and deacylated dye (100%). Treating data in this way has the benefit of allowing for the comparison of the probes in situations where there are differences in microscope settings day to day or between different cell or tissue types. Treatment of HEK293T cells with 1 μM RDP-1 or RDP-2 for 10 min results in about 28% and 18% depalmitoylation, respectively. See FIGS. 22 and 23. Pretreatment of the cells with the non-specific S-depalmitoylase inhibitor PalmB decreased the measured depalmitoylation activity almost in half for RDP-1 and RDP-2. See FIGS. 22 and 23. Treating cells with either ATP1 or APT2-selective inhibitor, ML348 and ML349, respectively, resulted in a slight increase in depalmitoylation activity from RDP-1. See FIGS. 24 and 25. Without being bound to any one theory, this observation was attributed to possible compensatory mechanisms, including changes in localization of other APTs that mask effects for the pan-depalmitoylase probe, RDP-1. In contrast, RDP-2 showed an about 30% decrease in depalmitoylation activity in ML348-treated HEK293T cells and an increase by about 12% upon ML349 treatment. See FIGS. 26A and 26B.

Figure 27:
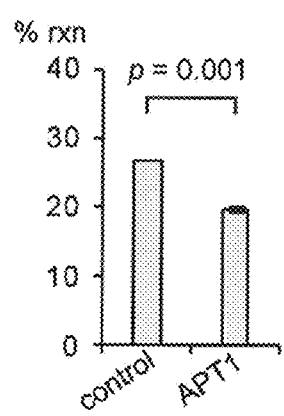
FIG. 27 is a graph showing the quantification of the ratiometric response of ratiometric depalmitoylation probe 2 (RDP-2) in live human embroyonic kidney (HEK293T) cells with and without knockdown of acyl protein thioesterase 1 (APT1). The cells were transfected with either a control short hairpin ribonucleic acid (shRNA) vector (control) or a vector generating shRNA targeting APT1 (APT1) for 48 hours and then loaded with 1 micromolar (μM) RDP-2 for 10 minutes and analyzed by fluorescence microscopy. "Blue" fluorescence was measured at an excitation wavelength ($\lambda_{ex}$) of 430 nanometers (nm) and an emission wavelength ($\lambda_{em}$) of 470 nm. "Green" fluorescence was measured at $\lambda_{ex}$ of 480 nm and $\lambda_{em}$ of 575 nm. Ratiometric images were generated by dividing the green channel by the blue channel. p=0.001. Error bars are ±standard deviation (n=3).
Figure 28:
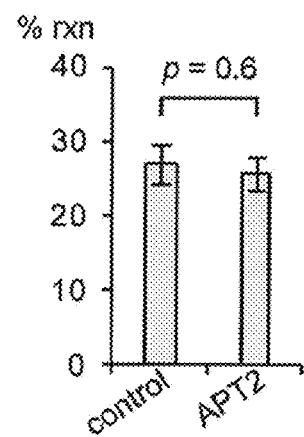
FIG. 28 is a graph showing the quantification of the ratiometric response of ratiometric depalmitoylation probe 2 (RDP-2) in live human embroyonic kidney (HEK293T) cells with and without knockdown of acyl protein thioesterase 2 (APT2). The cells were transfected with either a control short hairpin ribonucleic acid (shRNA) vector (control) or a vector generating shRNA targeting APT2 (APT2) for 48 hours and then loaded with 1 micromolar (μM) RDP-2 for 10 minutes and analyzed by fluorescence microscopy. "Blue" fluorescence was measured at an excitation wavelength ($\lambda_{ex}$) of 430 nanometers (nm) and an emission wavelength ($\lambda_{em}$) of 470 nm. "Green" fluorescence was measured at $\lambda_{ex}$ of 480 nm and $\lambda_{em}$ of 575 nm. Ratiometric images were generated by dividing the green channel by the blue channel. p=0.6. Error bars are ±standard deviation (n=3).

Without being bound to any one theory, the increase in RDP-2 signal upon APT2 inhibition is believed to be attributable to APT1 activation or change in localization to compensate for the loss of APT2, suggesting that RDP-2, which includes a lysine residue, is more sensitive to changes in APT1 activity, further illustrating why the unselective probe, RDP-1, shows increased activity with selective inhibitors. APT2 knockdown experiments with RDP-2 reveal that the compensatory APT activity only occurs with transient inhibition of APT2, while knocking down APT1 decreases RDP-2 deacylation similar to the levels with ML348. See FIGS. 27 and 28.

Example 12

Measurement of APT Activity in Organoids with RDPs

Figure 29:
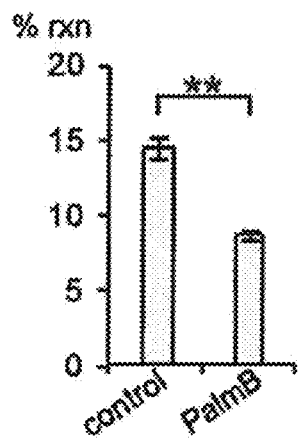
FIG. 29 is a graph showing the quantification of the ratiometric response of ratiometric depalmitoylation probe 2 (RDP-2) in human colon organoids with and without inhibition by palmostatin B (PalmB). The organoids were treated with dimethylsulfoxide (control) or 40 micromolar (μM) PalmB for 30 minutes and then loaded with 5 μM RDP-2 for 10 minutes and analyzed by fluorescence microscopy. "Blue" fluorescence was measured at an excitation wavelength ($\lambda_{ex}$) of 430 nanometers (nm) and an emission wavelength ($\lambda_{em}$) of 470 nm. "Green" fluorescence was measured at $\lambda_{ex}$ of 480 nm and $\lambda_{em}$ of 575 nm. Ratiometric images were generated by dividing the green channel by the blue channel. **p<0.005. Error bars are ±standard deviation (n=3).
Figure 30:
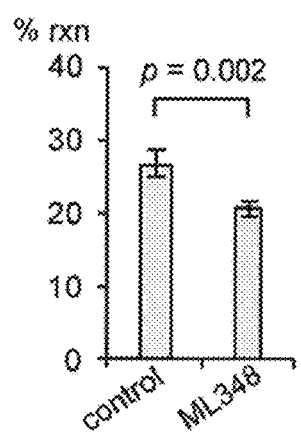
FIG. 30 is a graph showing the quantification of the ratiometric response of ratiometric depalmitoylation probe 2 (RDP-2) in human colon organoids with and without inhibition by acyl protein thioesterase 1 (APT1)-specific inhibitor ML348. The organoids were treated with dimethylsulfoxide (control) or 40 micromolar (μM) ML348 for 30 minutes and then loaded with 5 μM RDP-2 for 10 minutes and analyzed by fluorescence microscopy. "Blue" fluorescence was measured at an excitation wavelength ($\lambda_{ex}$) of 430 nanometers (nm) and an emission wavelength ($\lambda_{em}$) of 470 nm. "Green" fluorescence was measured at $\lambda_{ex}$ of 480 nm and $\lambda_{em}$ of 575 nm. Ratiometric images were generated by dividing the green channel by the blue channel. p=0.002. Error bars are ±standard deviation (n=3).

To determine the ability of RDPs to measure enzymatic activity in heterogenous primary tissue samples, human colon organoids were selected as an exemplary model in which to detect endogenous S-depalmitoylases and human metabolism. Imaging organoids can be challenging due to the high level of heterogeneity inherent to the tissue, and therefore, provides a challenging testbed to assay the presently disclosed probes. Colon organoids loaded with RDP-2 confirm that these human tissues have S-depalmitoyase activity. See FIG. 29. Pretreating the organoids with PalmB inhibited the measured S-depalmitoylation by about 50%. Furthermore, an about 20% decrease in S-depalmitoylase activity was observed when the organoids were treated with ML348, suggesting that APT1-like activity is present in the human colon. See FIG. 30. Accordingly, these studies show that RDPs can monitor endogenous APTs in primary tissue samples. A high degree of structural heterogeneity was observed between the organoids, substantiating the usefulness of the ratiometric nature of the RDP probes.

Example 13

Measurement of APT Activity Changes with RDPs During Lipid Stress

RDPs were tested for their ability to measure subtle changes to endogenous S-depalmitoylases during lipid stress conditions. Dysregulated fatty acid synthesis and stress has been observed in several diseases including cancer and non-alcoholic fatty liver disease. See Rohrig and Schulze, Nat. Rev. Cancer, 2016, 16, 732-749; Zhang et al., Lipids Health Dis., 2012, 11, 1; and Nissar et al., Toxicol. Res. (Bamb), 2015, 4, 1344-1358. As the liver is a major center of production of fatty acids, HEPG2 cells were chosen for study as they should be particularly sensitive to changes in fatty acid pools. See Rohrig and Schulze, Nat. Rev. Cancer, 2016, 16, 732-749. Additionally, treatment of HEPG2 with palmitate has been previously demonstrated to alter lipid metabolism and cause ER stress. Zhang et al., Lipids Health Dis., 2012, 11, 1; and Nissar et al., Toxicol. Res. (Bamb), 2015, 4, 1344-1358.

Figure 31:
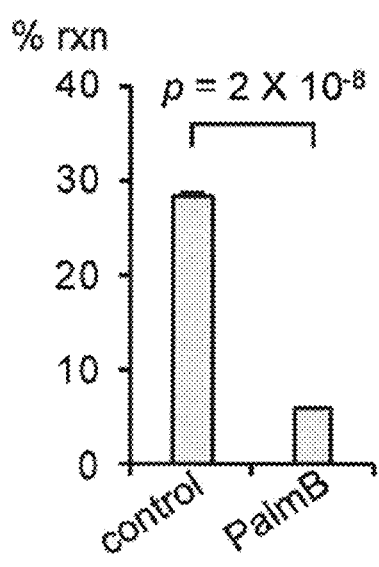
FIG. 31 is a graph showing the quantification of the ratiometric response of ratiometric depalmitoylation probe 1 (RDP-1) in human liver carcinoma (HEPG2) cells with and without inhibition by palmostatin B (PalmB). The cells were treated with dimethylsulfoxide (control) or 40 micromolar (μM) PalmB for 30 minutes and then loaded with 1 μM RDP-1 for 10 minutes and analyzed by fluorescence microscopy. "Blue" fluorescence was measured at an excitation wavelength ($\lambda_{ex}$) of 430 nanometers (nm) and an emission wavelength ($\lambda_{em}$) of 470 nm. "Green" fluorescence was measured at $\lambda_{ex}$ of 480 nm and $\lambda_{em}$ of 575 nm. Ratiometric images were generated by dividing the green channel by the blue channel. p=2×10$^{-8}$. Error bars are ±standard deviation (n=3).
Figure 32:
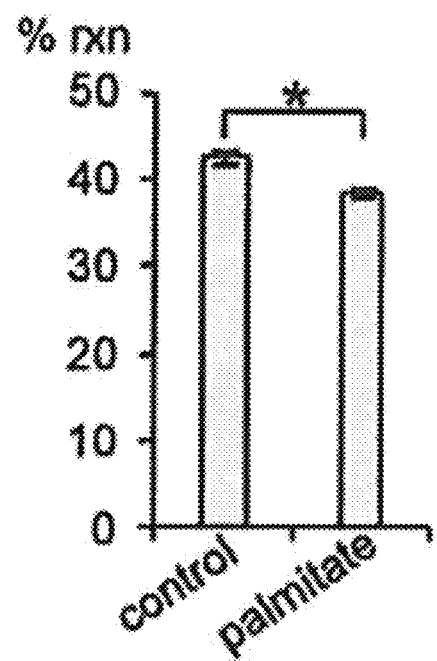
FIG. 32 is a graph showing the quantification of the ratiometric response of ratiometric depalmitoylation probe 2 (RDP-2) in human liver carcinoma (HEPG2) cells with and without inhibition by palmitate. The cells were treated with 1% bovine serum albumin (BSA, control) or 1 micromolar (μM) palmitate in 1% BSA for 6 hours and then loaded with 1 μM RDP-2 for 10 minutes and analyzed by fluorescence microscopy. "Blue" fluorescence was measured at an excitation wavelength ($\lambda_{ex}$) of 430 nanometers (nm) and an emission wavelength ($\lambda_{em}$) of 470 nm. "Green" fluorescence was measured at $\lambda_{ex}$ of 480 nm and $\lambda_{em}$ of 575 nm. Ratiometric images were generated by dividing the green channel by the blue channel. *p<0.03. Error bars are±standard deviation (n=3).

PalmB treatment of HEPG2 cells displayed an about 60% decrease in deacylation of RDP-1, confirming that the present probes can monitor APT activity in HEPG2 cells. See FIG. 31. Pretreatment of HEPG2 cells with palmitate for 6 hours resulted in a decrease in APT activity, as measured by RDP-1. See FIG. 32. Thus, the present study appears to validate the presence of a link between cellular lipid status and S-depalmitoylation activity.

Example 14

Methods and Materials for Examples 15-18

Dulbecco's Modified Eagle Medium (DMEM) Glutamax (10569-010, Gibco, Gaithersburg, Md., United States of America), fetal bovine serum (FBS, Qualified US origin; Gibco, Gaithersburg, Md., United States of America), Live Cell Imaging Solution (A14291DJ, Molecular Probes, Eugene, Oreg., United States of America), Opti-MEM (31985-070, Gibco, Gaithersburg, Md., United States of America), and Hoechst 33342 (Fisher, Hampton, N.H., United States of America), were purchased as mentioned in parenthesis. Silica gel P60 (SiliCycle Inc. Quebec City Canada; 40-63 µm, 230-400 mesh) was used for column chromatography. Analytical thin layer chromatography was performed using SiliCycle 60 F254 silica gel (precoated sheets, 0.25 mm thick; SiliCycle Inc., Quebec City, Canada). All chemicals for synthesis were purchased from Sigma-Aldrich (St. Louis, Mo., United States of America) or Fisher Scientific (Pittsburgh, Pa., United States of America) and used as received. $^1$H NMR and $^{13}$C NMR spectra were collected in NMR solvents $CDCl_3$ (Sigma-Aldrich, St. Louis, Mo., United States of America) at 25° C. using a 500 MHz Bruker Avance II+ spectrometer (Bruker Corporation, Billerica, Mass., United States of America) with 5 mm QNP probe or 400 MHz Bruker DRX400 spectrometer (Bruker Corporation, Billerica, Mass., United States of America). $^1$H-NMR chemical shifts are reported in parts per million (ppm) relative to the peak of residual proton signals from ($CDCl_3$ 7.26 ppm). Multiplicities are given as: s (singlet), d (doublet), t (triplet), q (quartet), dd (doublet of doublets), m (multiplet). $^{13}$C-NMR chemical shifts are reported in parts per million (ppm) relative to the peak of residual proton signals from (CDCl3 77.16 ppm). Analysis of NMR was done in iNMR version 5.5.1. and NMR plots were obtained from Topspin 2.1. High resolution mass was obtained from Agilent 6224 time-of-flight (TOF) High Resolution Accurate Mass Spectrometer (HRA-MS) (Agilent Technologies, Santa Clara, Calif., United States of America) using combination of APCI and ESI. Low resolution mass spectral analyses and liquid chromatography analysis were carried out on an Advion Expression-L mass spectrometer (Adivon, Ithaca, N.Y., United States of America) coupled with an Agilent 1220 Infinity LC System (Agilent Technologies, Santa Clara, Calif., United States of America). In vitro biochemical assays with purified APT1/APT2 enzymes were performed on Biotek synergy Neo2 plate reader (BioTek, Winooski, Vt., United States of America).

In Vitro Kinetic Assays and Emission Spectra of DPP-1, DPP-4, and DPP-5.

150 µL of 2 µM DPP-1, DPP4 or DPP-5 in HEPES (20 mM, pH=7.4, 150 mM NaCl) were added to a 96-well optical bottom plate (Nunc 265301, Fisher Scientific, Pittsburgh, Pa., United States of America) at room temperature. 150 µL of either HEPES buffer alone or HEPES buffer containing 100 nM APT1 or APT2 (purification using previous methods), was added using a multi-channel pipette, resulting in a final concentration of 1 µM DPP-1/DPP4/DPP-5 and 50 nM APT1 or APT2. Fluorescence intensities ($\lambda_{ex}$ 490/20 nm, $\lambda_{em}$ 545/20 nm, Gain 80, read from bottom with height 4.5 mm, and sweep method) were measured at 15 s time intervals for 30 min at 37° C. Following the 30 min kinetic run, emission spectra were obtained ($\lambda_{ex}$ 480/20 nm, $\lambda_{em}$ 515-700 nm, Gain 80, read from bottom with height 4.5 mm, and sweep method).

Enzyme Kinetics Analysis of DPP-5.

150 µL of 1 M DTT in HEPES buffer was added to different concentrations of 150 µL DPP-5 and then the stable fluorescence intensities of totally deacylated product were measured by the methods described above. Fluorescence intensity of per molar deacylated-product was then calculated by linear least-squares fitting of plots of fluorescence vs. concentration. For Michaelis-Menten constant, in vitro kinetics curves were obtained for different final concentrations of DPP-5 in HEPES with 50 nM APT1 or APT2. The fluorescence intensities measured were then normalized to the concentrations of product by fluorescence-intensity-permolar-product. A Lineweaver-Burk plot was used to calculate the Michaelis constant, $K_M$, and the maximum velocity, $V_{max}$, which is proportional to kcat by concentration of APT1 or APT2. All fits have $R^2$ values of >0.99.

Log P Analysis of DPP-1/4/5.

2 µL of 1 mM of DPP-1/4/5 was dissolved in 500 µL of Hepes buffer in two 1.5 mL tubes. To one tube, 500 µL of 1-octanol was added and the tube was shaken for 10 min followed by keeping it undisturbed for 10 min. Then, 10 µL of aqueous phase from each tube was placed in a 96 well plate reader. To this, 190 µL of 1M NaOH was added and fluorescence intensities ($\lambda_{ex}$ 490/20 nm, $\lambda_{em}$ 545/20 nm, Gain 80, read from bottom with height 4.5 mm, and sweep method) were measured at 15 second time intervals for 1 hr at room temperature. The fluorescence read out at saturation was used to calculate Log P values by following equation:

$$\log P = \log(F_{oct}/F_{aq})$$

$$F_{oct} = F\text{total} - F_{aq}$$

where: $F_{oct}$=Fluorescence of 1-octanol fraction; Faq=Fluorescence of the aqueous fraction after treatment with 1-octanol, and $F_{total}$=Fluorescence of the aqueous fraction with no treatment with 1-octanol.

Cell Culture and Maintenance.

HEK293T, HeLa cells, and HepG2 cells were obtained and maintained as described in Example 1.

Epifluorescent Imaging of DPP-5 with PalmB.

250,000 HEK293T cells/well, 120,000 HeLa cells/well, or 100,000 HepG2 cells/well were plated in 700 µL DMEM glutamax (10% FBS+1% P/S) into 4-well chambered imaging dish (D35C4-20-1.5-N, Cellvis, Mountain View, Calif., United States of America), which were precoated with 5 µg Poly-D-lysine (30-70 KDa, Alfa Aesar, Haverhill, Mass., United States of America) for 2 h. After 20-24 h, the media was replaced by 1 µM Hoechst 33342 and DMSO/5 µM PalmB in 400 µL DMEM glutamax. After 30 min of incubation at 37° C., the cells were washed with 400 µL of Live Cell Imaging Solution and replaced by 1 µM DPP-5 with DMSO or 5 µM of PalmB in Live Cell Imaging Solution. After 20 min of incubation at 37° C., images were obtained on an inverted epifluorescence microscope (Olympus IX83; Olympus Corporation, Tokyo, Japan) attached with EMCCD camera (Photometrics EVOLVE™ Delta, Photometrics, Tucson, Ariz., United States of America) with 40× oil objective (N/A 1.3) for DPP-5 (excitation filter 500/20, dichroic chroma 89007, emission filter 535/30), Hoechst 33342 (excitation filter 402/15, emission filter 455/50, dichroic chroma 89013), and brightfield. Analyses were performed in ImageJ. For data analysis, the average fluorescence intensity per image in each experimental condition was obtained by selecting ROI in Brightfield and applying that to the corresponding DPP-5 image, average background fluorescence intensity was subtracted and data was normalized to the average fluorescence intensity of the DMSO control. Each experiment was repeated in at least two biological replicates with identical results.

Epifluorescent Imaging of DPP-5 with ML348 and ML349.

16,000 HepG2 cells/well were plated in 100 µL DMEM glutamax (10% fetal bovine serum (FBS)) into 4 wells of a 96-well chambered imaging dish (P96-1-N, Cellvis, Mountain View Calif., United States of America), which were precoated with 0.7 µg Poly-D-lysine (30-70 KDa, Alfa Aesar, Haverhill, Mass., United States of America) for 2 hrs. After 24 h, cells were washed with Live Cell Imaging Solution and replaced by 1 µM Hoechst 33342 and DMSO/ 10 µM ML348/10 µM ML349/10 µM of both ML348 and ML349 in 100 µL DMEM glutamax. After 30 min of incubation at 37° C., the cells were washed with 100 µL of Live Cell Imaging Solution and replaced by 1 µM DPP-5 in Live Cell Imaging Solution. After 20 min of incubation at 37° C., images were obtained on an inverted epifluorescence microscope (Leica DMi8; Leica Microsystems, Wetzlar, Germany) equipped with a camera (Hamamatsu Orca-Flash 4.0; Hamamatsu, Hamamatsu City, Japan) with 63× oil objective (N/A 1.4) and light source (Sutter Lamda XL, 300 W Xenon; Sutter Instrument, Novato, Calif., United States of America) for DPP-5 (YFP filter cube 1525306), Hoechst 33342 (DAPI filter cube), and brightfield using Leica LASX software (Leica Microsystems, Wetzlar, Germany). Analyses were performed in ImageJ. Each experiment was repeated in three biological replicates and 8-12 images were considered for plotting bar graphs for quantification. For detailed data analysis, the average fluorescence intensity per image in each experimental condition was obtained by selecting ROI in Brightfield and applying that to the corresponding DPP-5 image, average background fluorescence intensity was subtracted and data was normalized to the average fluorescence intensity of the control experiment. Epifluorescent imaging for comparing DPP-1, DPP-4 and DPP-5. 250,000 HEK293T cells/well were plated in 700 µL DMEM glutamax (10% FBS+1% P/S) into three wells of a 4-well chambered imaging dish (D35C4-20-1.5-N, Cellvis, Mountain View, Calif., United States of America), which were precoated with 5 µg Poly-Dlysine (30-70 KDa, Alfa Aesar, Haverhill, Mass., United States of America) for 2 h. After 18 h, the media was replaced by 1 µM Hoechst 33342 in 400 µL DMEM glutamax. After 30 min of incubation at 37° C., the cells were washed with 400 µL of Live Cell Imaging Solution and replaced by 1 µM DPP-1/DPP-4/ DPP-5 in Live Cell Imaging Solution. After 20 min of incubation at 37° C., images were obtained and analyzed as described above.

Epifluorescent Imaging of DPP-5 with Palmitate.

100,000 HepG2 cells/well were plated in 700 µL DMEM glutamax (10% FBS) into two wells of a 4-well chambered imaging dish (D35C4-20-1.5-N, Cellvis, Mountain View, Calif., United States of America), which were precoated with 5 µg Poly-D-lysine (30-70 KDa, Alfa Aesar, Haverhill, Mass., United States of America) for 2 hrs. After 18 h, media was replaced by 500 µL DMEM glutamax for starvation. After 6 h of starvation, cells were treated for another 6 h with 500 µL of 1% BSA±1 mM Palmitate made with DMEM glutamax. Then, 20 µL of 21 µM Hoechst 33342 in DMEM glutamax was added to each well such that final concentration of Hoechst 33342 is 1 µM. After 30 min of incubation at 37° C., the cells were washed with 400 µL of Live Cell Imaging Solution and replaced by 1 μM DPP-5 in Live Cell Imaging Solution. After 20 min of incubation at 37° C., images were obtained and analysis was performed as described above. Each experiment was repeated in two biological replicates with identical results.

Epifluorescent Imaging of DPP-5 with PalmB on Palmitate Treatment.

13,000 HepG2 cells/well were plated in 100 μL DMEM glutamax (10% FBS) into 4 wells of a 96-well chambered imaging dish (P96-1-N, Cellvis, Mountain View, Calif., United States of America). After 18 h, media was replaced by 100 μL DMEM glutamax for starvation. After 6 h of starvation, cells were treated for another 6 h with 100 μL of 1% BSA±1 mM Palmitate made with DMEM glutamax. Then, 100 μL of 1 μM Hoechst 33342 prepared in 1% BSA±1 mM Palmitate with DMSO/5 μM PalmB was added to respective wells. After 30 min of incubation at 37° C., the cells were washed with 100 μL of Live Cell Imaging Solution and replaced by 1 μM DPP-5 in Live Cell Imaging Solution. After 20 min of incubation at 37° C., images were obtained on Leica epifluorescent microscope (Leica Microsystems, Wetzlar, Germany) and analyzed as described above.

Epifluorescent Imaging of Diacetyl Rhodol on Palmitate Treatment.

13,000 HepG2 cells/well were plated in 100 μL DMEM glutamax (10% FBS) into 2 wells of a 96-well chambered imaging dish (P96-1-N, Cellvis, Mountain View, Calif., United States of America). After 18 h, media was replaced by 100 μL DMEM glutamax for starvation. After 6 h of starvation, cells were treated for another 6 h with 100 μL of 1% BSA±1 mM Palmitate made with DMEM glutamax. Then, 100 μL of 1 μM Hoechst 33342 prepared in 1% BSA±1 mM Palmitate was added to respective wells. After 30 min of incubation at 37° C., the cells were washed with 100 μL of Live Cell Imaging Solution and replaced by 1 μM diacetyl rhodol in Live Cell Imaging Solution. After 20 min of incubation at 37° C., images were obtained on Leica epifluorescent microscope (Leica Microsystems, Wetlar, Germany) and analyzed as described above.

Flexible Ligand-Rigid Receptor Molecular Docking.

Flexible ligand-rigid receptor molecular docking was performed with DPP-4 and DPP-5 using Autodock Vina 1.1.2 (exhaustiveness=1024) (see Trott and Olson (2010) J Comput Chem 31, 455-461) on a homebuilt server with an Intel Xeon E3-1220 V3 3.1 GHz Quad-Core Processor and 16 GB of ECC RAM running the latest stable release of Debian 8 Linux. Ligands were prepared in Avogadro 1.1.1 (see Hanwell et al. (2012) J Cheminform 4, 17) and MGL-Tools 1.5.7rcl (see Morris et al. (2009) J Comput Chem 30, 2785-2791) with energy minimization carried out using the MMFF94s forcefield as implemented in openbabel 2.3.2. See O'Boyle et al. (2011) J Cheminform 3, 33. Receptor structures PDB: 5SYM and 5SYN (see Won et al. (2016) ACS Chem Biol 11, 3374-3382) were prepared in PyMOL 1.7 (Schrodinger, LLC, New York, N.Y., United States of America). Existing hydrogens, where present, were removed and replaced using MolProbity 4.4 (see Chen et al. (2010) Acta Crystallogr D Biol Crystallogr 66, 12-21) to ensure the structure properly modeled protonation at pH 7.4. Grid volumes were set to enclose the active site. Analysis of the lowest five energy confirmations and generation of figures were performed using PyMOL.

Example 15

Synthesis of DPP-4 and DPP-5

Scheme 6. Synthesis of Compound 17.

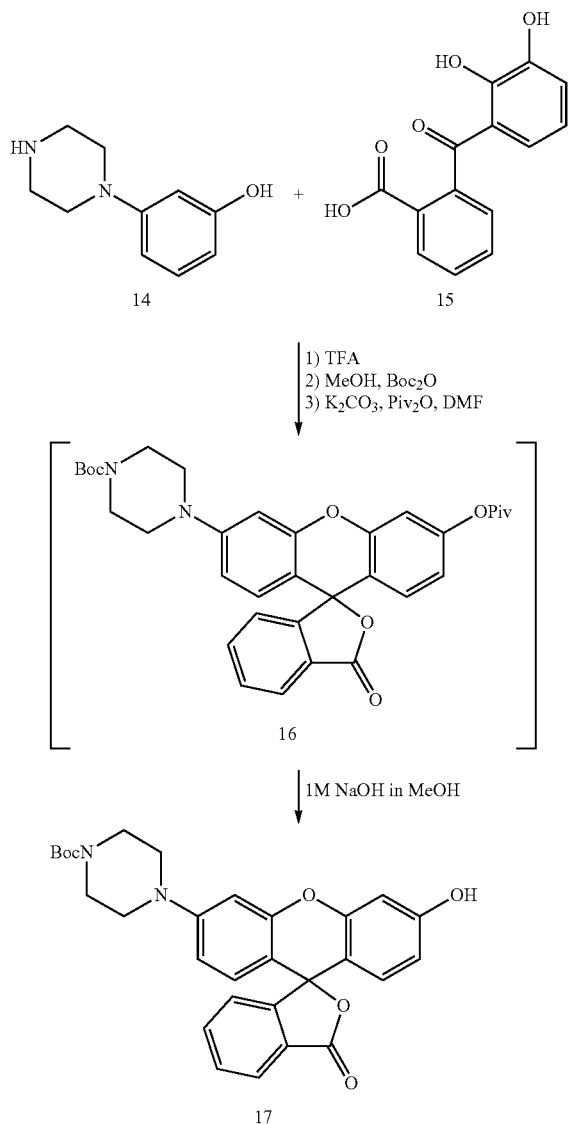

The synthesis of intermediate Boc-protected rhodol (compound 17) used in the preparation of additional DPPs comprising piperizine-based fluorophore substitutions was performed as shown above in Scheme 6 via a route adapted from the literature. See Dickinson and Chang (2008) J Am Chem Soc 130, 9638-9639.

Briefly, to a mixture of 14 (2.143 g, 1.0 eq, 12.02 mmol) and 15 (see Smith et al. (1993) J Chem Soc, Perkin Trans 2, 1195-1204) (3.053 g, 1.0 eq, 11.82 mmol) in a pressure flask, TFA (5 mL) was added, and the resulting reaction mixture was stirred at 95° C. for 9 h. The reaction mixture was diluted 3× with 30 mL of DCM, followed by rotatory evaporation to remove the residual TFA. To the resultant crude material, Et$_3$N (7.2 mL, 5 eq, 51.7 mmol) and MeOH (25 mL) were added. After stirring for 5 min, Boc$_2$O (2.106 g, 0.93 eq, 9.6 mmol) was added. After stirring the resultant reaction mixture overnight at room temperature, the MeOH was removed by rotatory evaporation. To the crude mixture, K$_2$CO$_3$ (4.287 g, 3.0 eq, 31.0 mmol), pivalic anhydride (2.1 mL, 1.0 eq, 10.3 mmol) and DMF (15 mL) were added and the reaction stirred for 1 h. The reaction mixture was diluted with 30 mL DCM, filtered, and evaporated. The crude product was purified by column chromatography (Silica; 0-20% EtOAc:DCM) to yield 16. The combined fractions of 16 were evaporated and dissolved in MeOH (60 mL), to which 3 M NaOH (30 mL) was added, and reaction mixture stirred for 30 min at room temperature. The reaction mixture was then evaporated by rotatory evaporation, the crude product was diluted by DCM (50 mL), and then washed by aq. HCl (pH~3-4). The aqueous layer was further extracted by DCM 2×30 mL, the combined organic layer was dried over $Na_2SO_4$, and then evaporated to give a crude product. Purification by column chromatography (Silica; 0-5% MeOH:DCM) yielded 17 (3.892 g, 65%). Rf: 0.41 (Silica; 5% MeOH:DCM). $^1$H-NMR (500 MHz; $CDCl_3$): δ 9.04-8.92 (b, 1H), 8.02 (dd, J=6.4, 1.9 Hz, 1H), 7.61-7.55 (m, 2H), 7.10-7.09 (m, 1H), 6.73 (d, J=8.8 Hz, 1H), 6.67-6.64 (m, 2H), 6.60-6.52 (m, 3H), 3.51 (d, J=4.7 Hz, 4H), 3.21 (s, 4H), 1.46 (s, 9H). $^{13}$C-NMR (126 MHz; $CDCl_3$): 170.3, 162.1, 154.9, 153.8, 153.5, 148.6, 134.0, 129.8, 129.6, 129.5, 129.2, 126.2, 125.2, 114.3, 112.5, 111.3, 110.7, 103.1, 80.6, 53.5, 52.4, 49.2, 47.7, 28.5, 27.2, 27.1. HRA-MS(+): Calculated for $C_{29}H_{28}N_2O_6$ [M+] 500.1947; found 500.1953.

Scheme 7. Synthesis of DPP-4 and DPP-5

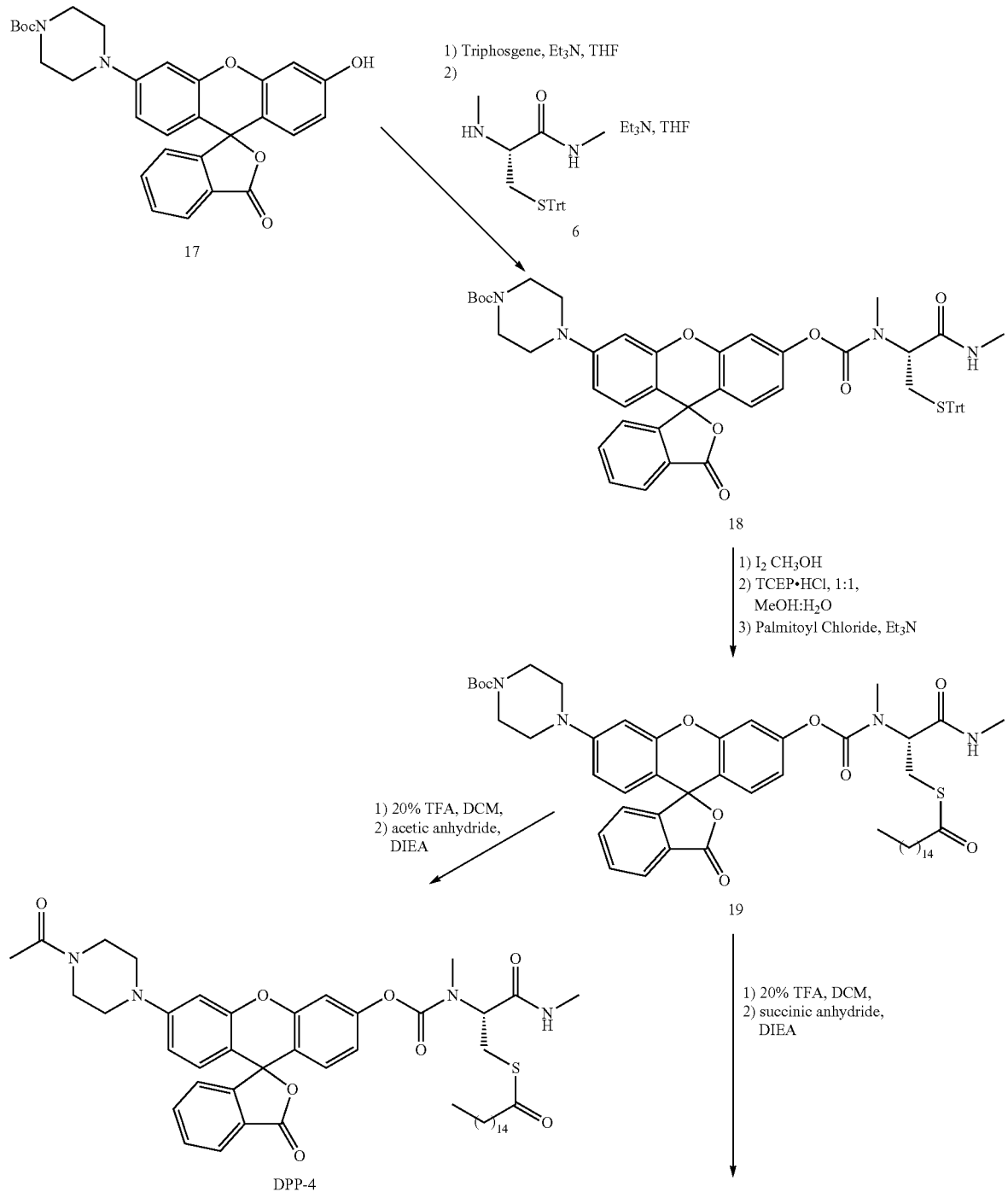

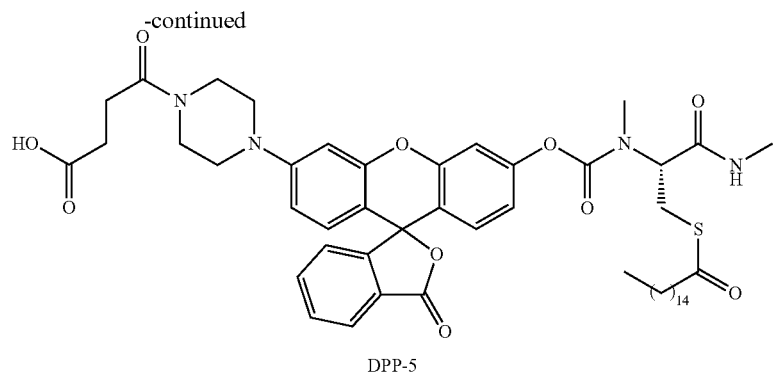

DPP-5

The synthesis of additional DPPs was then performed as shown in Scheme 7, above, using intermediate Boc-protected rhodol 17 and compound 6 described above in Example 2.

Synthesis of 18.

To a solution of 17 (306.4 mg, 0.612 mmol, 1.0 eq) in dry THF (7 mL) Et$_3$N (0.8 M, 0.77 mL, 0.613 mmol, 1.0 eq) was added. The resultant solution was added dropwise over 15 min to a solution of triphosgene (181.6 mg, 0.612 mmol, 1.0 eq) in dry THF (5 mL) in an ice bath. After 5 min, the ice bath was replaced by a 40° C. water bath and N$_2$ flushed through the reaction mixture to evaporate the solvent completely. Then, the 40° C. water bath was removed and the crude product was suspended in dry THF (4 mL). To this reaction mixture, 6 (0.32 M, 1.88 mL, 0.609 mmol, 1.0 eq), followed by Et$_3$N (0.8 M, 0.77 mL, 0.613 mmol, 1.0 eq), were added dropwise. After 15 min of stirring, the reaction mixture was quenched by five drops of 1M HCl and the solvent evaporated by rotary evaporation. The crude reaction crude was purified by column chromatography (Silica; 5-25% EtOAc:DCM) to yield 18 (259.8 mg; 46%). Rf: 0.39 (Silica; 15% EtOAc:DCM). $^1$H-NMR (500 MHz; CDCl3): δ 8.05 (t, J=6.5 Hz, 1H), 7.70-7.62 (m, 2H), 7.50-7.45 (m, 6H), 7.33-7.09 (m, 11H), 6.84-6.63 (m, 5H), 6.15-6.07 (m, 1H), 4.35 (m, 4.9 Hz, 1H), 3.61 (t, J=4.8 Hz, 4H), 3.25 (d, J=4.5 Hz, 4H), 2.90 (d, J=0.8 Hz, 2H), 2.83-2.68 (m, 5H), 1.53 (s, 10H). $^{13}$C-NMR (126 MHz; CDCl$_3$): δ 169.4, 169.1, 169.1, 155.0, 154.6, 153.0, 153.0, 152.9, 152.8, 152.4, 152.2, 151.9, 151.9, 144.4, 135.1, 129.8, 129.6, 129.5, 128.9, 128.8, 128.0, 126.8, 126.6, 125.0, 124.0, 123.9, 117.3, 117.3, 116.5, 116.4, 112.3, 110.3, 110.2, 109.1, 102.2, 82.8, 82.7, 80.1, 67.2, 67.1, 67.1, 67.0, 58.5, 48.1, 31.3, 30.8, 30.7, 30.3, 28.4, 26.3, 26.1. HRA-MS(+): Calculated for C$_{54}$H$_{52}$N$_4$O$_8$S [M+] 916.3506; found 916.3508.

Synthesis of 19.

To a solution of 18 (408 mg, 0.445 mmol, 1.0 eq) in MeOH (10 mL), I$_2$ (226 mg in 4 mL MeOH; 0.890 mmol, 2.0 eq) was added dropwise over 5 min. The reaction mixture was quenched with a solution of 0.2 M sodium citrate and 0.2 M sodium ascorbate at pH ~3-4 until the yellow color disappeared. The quenched reaction mix was diluted with DCM (25 mL) and washed with brine (25 mL). The aqueous layer was washed again with DCM (25 mL). The combined organic layers were dried over Na$_2$SO$_4$ and evaporated by rotary evaporation. The resultant crude containing the disulfide product was suspended with 1 mL H$_2$O and dissolved with minimal amount of MeOH. Then TCEP.HCl (638 mg, 2.23 mmol, 5.0 eq) was added. The reaction mixture was stirred at room temperature until no starting material was observed by LC-MS. The reaction was treated with 20 mL 0.1 M HCl and extracted with 25 mL DCM. The aqueous layer was washed again with DCM (25 mL). The combined organic layers were dried over Na$_2$SO$_4$ and evaporated by rotary evaporation. The resultant crude containing the free thiol product was dissolved with 4 mL DCM and added into palmitoyl chloride (405 µL, 1.335 mmol, 3.0 eq). The red solution was treated with Et$_3$N dropwise until no starting material was observed by LC-MS. The resulting reaction mixture was diluted with DCM (25 mL) and washed with concentrated NaHCO$_3$ followed by brine (20 mL). The aqueous layer was washed again with DCM (20 mL) and the combined organic layers were dried over Na$_2$SO$_4$ and evaporated by rotary evaporation. Purification by column chromatography (Silica; 0-100% Ethyl acetate in Hexane plus 2% MeOH) afforded 19 as light red oil (240.4 mg, 59.2%). Purity was assayed by LC/MS. R$_f$: 0.53 (Silica; 1:2 EtOAc:DCM). $^1$H-NMR (500 MHz; CDCl$_3$): δ 8.03 (d, J=7.5 Hz, 1H), 7.69-7.61 (m, 2H), 7.16-7.10 (m, 2H), 6.83-6.77 (m, 2H), 6.70-6.61 (m, 3H), 6.26 (m, 1H), 4.83-4.71 (m, 1H), 3.59 (s, 4H), 3.48 (dd, J=14.2, 5.9 Hz, 1H), 3.37-3.31 (m, 1H), 3.23 (s, 4H), 3.06 (s, 2H), 2.95 (s, 1H), 2.87 (t, J=4.7 Hz, 1H), 2.81 (t, J=4.2 Hz, 2H), 2.56 (m, 2H), 1.65 (dt, J=14.9, 7.5 Hz, 3H), 1.27 (s, 32H), 0.89 (t, J=6.9 Hz, 3H). $^{13}$C-NMR (126 MHz; CDCl$_3$): δ 198.6, 169.3, 169.2, 155.1, 154.6, 152.8, 152.3, 152.2, 151.9, 135.1, 129.8, 128.9, 126.6, 125.2, 80.1, 44.1, 31.9, 29.6, 29.5, 29.4, 29.3, 29.2, 29.1, 28.9, 28.4, 27.3, 25.5, 22.6, 14.1. HRA-MS(+): Calculated for C$_{51}$H$_{68}$N$_4$O$_9$S [M+] 912.4707; found 912.4720.

Synthesis of DPP-4. A solution of 19 (61.0 mg, 66.8 µmol, 1.0 eq) in 20% TFA:DCM (5 mL) was stirred for 30 min at room temperature, followed by dilution with DCM (3×20 mL) and evaporation by rotary evaporation. The resulting crude was suspended in DCM (5 mL) and acetic anhydride (51 µL, 0.540 mmol, 8.0 eq) was added followed by slowly addition of DIEA until reaction was completed. The reaction mix was diluted with DCM (20 mL) then washed with concentrated NaHCO$_3$ followed by brine (20 mL). The aqueous layer was washed again with DCM (20 mL) and the combined organic layers were dried over Na$_2$SO$_4$ and evaporated by rotary evaporation.

Purification by column chromatography (Silica; 50% DCM in ethyl acetate with 0-5% MeOH) afforded DPP-4 as colorless oil (35.0 mg, 61.4%). R$_f$: 0.2 (Silica; 1:1 EtOAc:DCM). $^1$H-NMR (500 MHz; CDCl3): δ 8.03 (s, 1H), 7.69-7.62 (m, 2H), 7.17-7.10 (m, 2H), 6.85-6.77 (m, 2H), 6.70-6.67 (m, 2H), 6.62 (dd, J=8.9, 2.2 Hz, 1H), 6.25 (br, 1H), 4.82-4.70 (m, 1H), 3.79-3.74 (m, 2H), 3.63 (t, J=4.9 Hz, 2H), 3.48 (dd, J=14.1, 5.9 Hz, 1H), 3.37-3.24 (m, 5H), 3.06 (s, 2H), 2.96 (s, 1H), 2.88 (t, J=3.7 Hz, 1H), 2.83 (t, J=3.8 Hz, 2H), 2.56 (m, 2H), 1.66 (m, 2H), 1.27 (m, 27H), 0.89 (t, J=7.0 Hz, 3H). $^{13}$C-NMR (126 MHz; CDCl$_3$): δ 198.8, 171.3, 169.5, 169.3, 169.2, 155.3, 153.1, 152.6, 152.5, 152.3, 152.0, 135.2, 129.9, 129.0, 128.9, 126.7, 125.2, 124.1, 117.4, 116.7, 112.5, 110.3, 109.6, 102.5, 82.7, 60.5, 58.8, 48.5, 48.2, 46.0, 44.2, 41.1, 32.0, 31.2, 29.8, 29.7, 29.5, 29.3, 29.0, 27.4, 26.4, 25.7, 22.8, 21.4, 21.2, 14.3, 14.2. HRA-MS(+): Calculated for C$_{48}$H$_{62}$N$_4$O$_8$S [M+] 854.4288; found 854.4261.

Synthesis of DPP-5.

A solution of 19 (63.4 mg, 69.4 μmol, 1.0 eq) in 20% TFA:DCM (5 mL) was stirred for 30 min at room temperature, followed by dilution with DCM (3×20 mL) and evaporation by rotary evaporation. The resulting crude was suspended in DCM (5 mL) and succinic anhydride (55.6 mg, 0.555 mmol, 8.0 eq) was added followed by slowly addition of DIEA until reaction was completed. The reaction mix was acidified with 10 mL 1M HCl and diluted with DCM (20 mL) then washed with brine (20 mL). The aqueous layer was washed again with DCM (20 mL) and the combined organic layers were dried over Na$_2$SO$_4$ and evaporated by rotary evaporation. Purification by column chromatography (Silica; 0-10% MeOH in DCM) afforded DPP-5 as a pink solid (43.8 mg, 69.1%). R$_f$: 0.33 (Silica; 5% MeOH:DCM). $^1$H-NMR (500 MHz; CDCl$_3$): δ 8.03 (d, J=7.5 Hz, 1H), 7.69-7.62 (m, 2H), 7.16-7.09 (m, 2H), 6.85-6.76 (m, 2H), 6.67 (dd, J=7.8, 4.9 Hz, 2H), 6.60 (dd, J=8.9, 2.0 Hz, 1H), 6.44 (d, J=4.8 Hz, 1H), 4.81-4.71 (m, 1H), 3.76 (s, 2H), 3.70 (s, 2H), 3.64 (s, 1H), 3.47 (dd, J=14.1, 6.1 Hz, 1H), 3.35-3.23 (m, 4H), 3.06 (s, 2H), 2.95 (s, 1H), 2.87 (t, J=4.1 Hz, 1H), 2.81 (dd, J=4.7, 2.8 Hz, 2H), 2.72-2.65 (m, 4H), 2.57 (q, J=7.2 Hz, 2H), 1.67-1.60 (m, 2H), 1.25 (d, J=7.0 Hz, 24H), 0.89 (t, J=6.9 Hz, 3H). $^{13}$C-NMR (126 MHz; CDCl$_3$): δ 198.9, 176.6, 170.4, 169.5, 169.4, 155.3, 153.1, 152.5, 152.3, 152.0, 135.2, 130.0, 129.0, 128.9, 126.6, 125.2, 124.1, 117.4, 116.6, 112.4, 110.3, 109.5, 102.4, 82.8, 48.2, 48.0, 45.0, 44.2, 41.5, 32.0, 31.2, 31.1, 29.8, 29.7, 29.5, 29.4, 29.3, 29.0, 28.8, 28.0, 27.4, 26.6, 26.5, 25.6, 22.8, 14.2. HRA-MS(+): Calculated for C$_{50}$H$_{64}$N$_4$O$_{10}$S [M$^+$]912.4343; found 912.4344.

Example 16

Characterization and In Vitro Activity of DPP-4 and DPP-5

The rhodol-based scaffold of the presently disclosed DPPs offers several synthetically tractable positions at which to install solubilizing groups. For example, in DPP-4 and DPP-5, a piperazine moiety was covalently attached to the xanthene portion of the rhodol scaffold, in a similar strategy to that previously used to make modified fluorescent probes. See Dickinson and Chang (2008) J Am Chem Soc 130, 9638-9639. DPP-4 has an acetyl amide modification on the piperazine, while DPP-5 has a succinylated amide and, thus, includes a carboxylic acid. These modifications are not located at or near the substrate recognition portion of the probe (i.e., the palmitoylated cysteine residue), and, therefore, should have minimal interference with enzymatic activity by S-depalmitoylases reacting at the substrate recognition portion of the probe. Molecular modeling appeared to confirm this lack of interference.

Figure 33A:
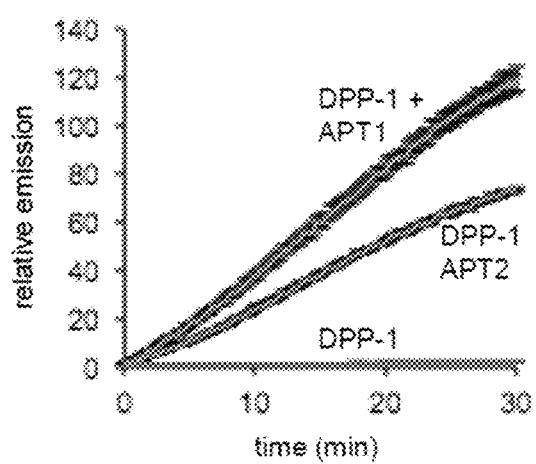
FIG. 33A is a graph showing an in vitro fluorescence assay of 1 micromolar (μM) depalmitoylation probe 1 (DPP-1). The assay was performed with either 50 nanomolar (nM) purified acyl protein thioesterase 1 (APT1) or acyl protein thioesterase 2 (APT2). Fluorescence is normalized based on the fluorescence of the probe in the absence of enzyme. The excitation wavelength ($\lambda_{ex}$) was 490/9 nanometers (nm) and the emission wavelength ($\lambda_{em}$) was 545/20 nm. Error bars are standard deviation of the mean (n=4).
Figure 33B:
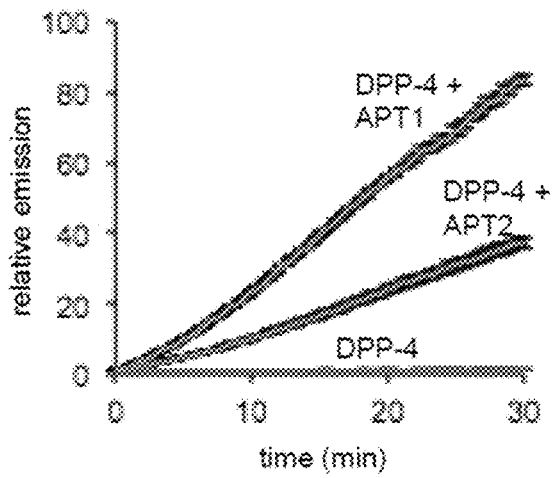
FIG. 33B is a graph showing an in vitro fluorescence assay of 1 micromolar (μM) depalmitoylation probe 4 (DPP-4). The assay was performed with either 50 nanomolar (nM) purified acyl protein thioesterase 1 (APT1) or acyl protein thioesterase 2 (APT2). Fluorescence is normalized based on the fluorescence of the probe in the absence of enzyme. The excitation wavelength ($\lambda_{ex}$) was 490/9 nanometers (nm) and the emission wavelength ($\lambda_{em}$) was 545/20 nm. Error bars are standard deviation of the mean (n=4).
Figure 33C:
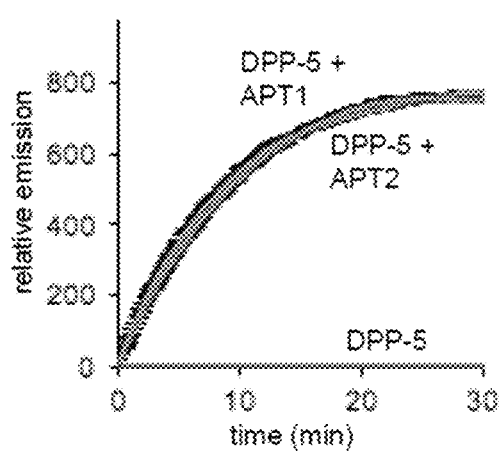
FIG. 33C is a graph showing an in vitro fluorescence assay of 1 micromolar (μM) depalmitoylation probe 5 (DPP-5). The assay was performed with either 50 nanomolar (nM) purified acyl protein thioesterase 1 (APT1) or acyl protein thioesterase 2 (APT2). Fluorescence is normalized based on the fluorescence of the probe in the absence of enzyme. The excitation wavelength ($\lambda_{ex}$) was 490/9 nanometers (nm) and the emission wavelength ($\lambda_{em}$) was 545/20 nm. Error bars are standard deviation of the mean (n=4).
Figure 33D:
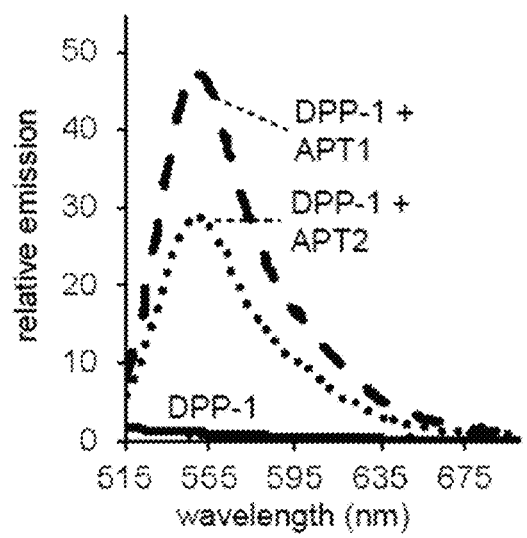
FIG. 33D is a graph showing a fluorescence emission spectrum of a depalmitoylation probe 1 (DPP-1) in 4-(2-hydroxyethyl)-1-piperazine-ethanesulfonic acid (HEPES) buffer (20 millimolar mM, at pH 7.4, 150 mM sodium chloride (NaCl)), as well as the emission spectra after treatment of DPP-1 with either 50 nanomolar (nM) acyl protein thioesterase 1 (APT1, dashed line) or 50 nM acyl protein thioesterase 2 (APT2, dotted line) for 20 minutes. The emission wavelength ($\lambda_{em}$) is 485 nanometers (nm). Data is normalized to the background of the probe alone (solid line).
Figure 33E:
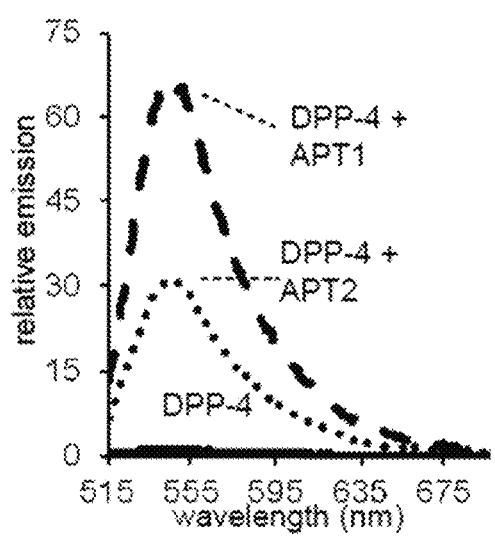
FIG. 33E is a graph showing a fluorescence emission spectra of depalmitoylation probe 4 (DPP-4) in 4-(2-hydroxyethyl)-1-piperazineethanesulfonic acid (HEPES) buffer (20 millimolar mM, at pH 7.4, 150 mM sodium chloride (NaCl)), as well as the emission spectra after treatment of DPP-4 with either 50 nanomolar (nM) acyl protein thioesterase 1 (APT1, dashed line) or 50 nM acyl protein thioesterase 2 (APT2, dotted line) for 20 minutes. The emission wavelength ($\lambda_{em}$) is 485 nanometers (nm). Data is normalized to the background of the probe alone (solid line).
Figure 33F:
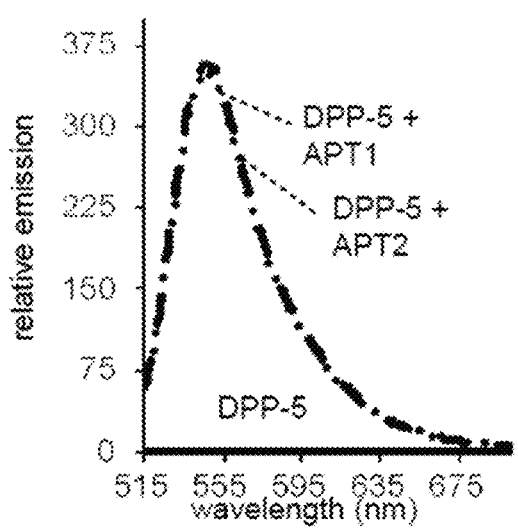
FIG. 33F is a graph showing a fluorescence emission spectra of depalmitoylation probe 5 (DPP-5) in 4-(2-hydroxyethyl)-1-piperazineethanesulfonic acid (HEPES) buffer (20 millimolar mM, at pH 7.4, 150 mM sodium chloride (NaCl)), as well as the emission spectra after treatment of DPP-5 with either 50 nanomolar (nM) acyl protein thioesterase 1 (APT1, dashed line) or 50 nM acyl protein thioesterase 2 (APT2, dotted line) for 20 minutes. The emission wavelength ($\lambda_{em}$) is 485 nanometers (nm). Data is normalized to the background of the probe alone (solid line).

In vitro kinetics of DPP-4 and DPP-5 with recombinantly expressed APT1 and APT2 were compared to those of DPP-1. Both DPP-1 (see FIG. 33A) and DPP-4 (see FIG. 33B) display relatively slow kinetics with APT1 and APT2 in the absence of detergents. After incubation for 30 minutes with 1 μM probe and 50 nM APT1 or APT2, DPP-1 and DPP-4 showed only about 50- or 30-fold and 70- or 30-fold enhancement in the intensities of their fluorescence signals, respectively. See FIGS. 33D and 33E. DPP-5 showed a more rapid turn-on response to both APT1 and APT2 (see FIG. 33C), with a 350-fold increase in the intensity of the fluorescent signal with both enzymes. See FIG. 33F. Without being bound to any one theory, it is believed that the more rapid kinetics of DPP-5 is due to the enhanced water solubility afforded by the additional carboxylate group. Log P analysis of DPP-1, DPP-4, and DPP-5 appears to confirm the relatively higher water solubility of DDP-5 compared to the other two probes. See Table 2, below. Kinetic analysis (see Table 3, below) revealed that DPP-5 has kinetic parameters comparable to those of previously reported N-Ras-based semisynthetic substrates for APT1 and APT2. See Rusch et al. (2011) Angew Chem Int Ed 50, 9838-9842. Quantitative analysis of DPP-1 and DPP-4 could not be performed in view of their slow kinetics in the absence of detergents.

TABLE 2

LogP analysis of DPP probes.

| Probe | LogP |
| --- | --- |
| DPP-1 | 1.57 |
| DPP-4 | 1.74 |
| DPP-5 | 0.79 |

TABLE 3

Kinetic Parameters of APT1 and APT2 with DPP-5.

|  | $K_M$ (μM) | $K_{cat}$ (s$^{-1}$) | $K_{cat}/K_M$ (s$^{-1}$M$^{-1}$) |
| --- | --- | --- | --- |
| APT1 | 1.6 | 0.044 | $2.8 \times 10^4$ |
| APT2 | 2.1 | 0.066 | $3.1 \times 10^4$ |

Example 17

Live Cell Assays with DPP-5

Figure 34:
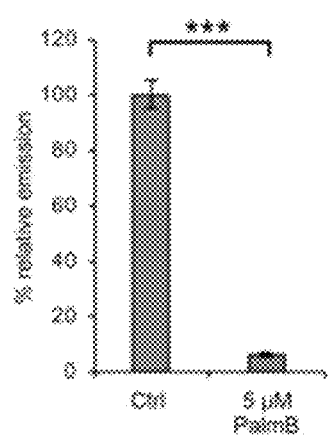
FIG. 34 is a graph showing the relative fluorescence response of depalmitoylation probe 5 (DPP-5) in human embryonic kidney (HEK293T) cells. One micromolar (μM) DPP-5 was loaded into HEK293T cells for 20 minutes with dimethylsulfoxide (DMSO, "Ctrl") and 5 μM inhibitor (palmostatin B (PalmB)) after a 30 minute treatment of the cells with either DMSO or 5 μM PalmB, and then analyzed by epifluorescence microscopy. ***p<0.005. Error bars are standard errors of the mean (n=3). Statistical analysis was performed with a two-tailed Student's t-test with unequal variance.

Human embryonic kidney (HEK293T) cells were loaded with 1 μM DPP-5 for 20 minutes and then analyzed by fluorescence microscopy. Cells loaded with DPP-5 displayed a bright, intracellular fluorescent signal. To determine whether the observed signal was due to endogenous S-depalmitoylases, palmostatin B (PalmB), a β-lactone-based pan-inhibitor of the S-depalmitoylases (see Dekker et al. (2010) Nat Chem Biol 6, 449-456) was also added to the cells. Pretreatment of the HEK293T cells with PalmB prior to the addition of DPP-5 abolished about 95% of the fluorescent signal. See FIG. 34.

Figure 35:
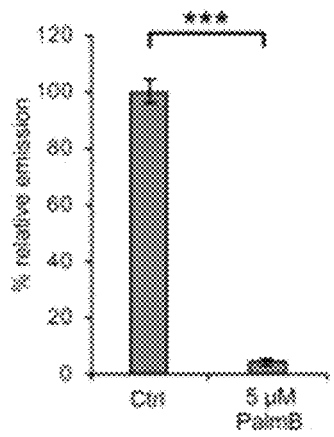
FIG. 35 is a graph showing the relative fluorescence response of depalmitoylation probe 5 (DPP-5) in human liver carcinoma (HepG2) cells. One micromolar (μM) DPP-5 was loaded into HepG2 cells for 20 minutes with dimethylsulfoxide (DMSO, "Ctrl") and 5 μM inhibitor (palmostatin B (PalmB)) after a 30 minute treatment of the cells with either DMSO or 5 μM PalmB, and then analyzed by epifluorescence microscopy. ***p<0.005. Error bars are standard errors of the mean (n=3). Statistical analysis was performed with a two-tailed Student's t-test with unequal variance.
Figure 36:
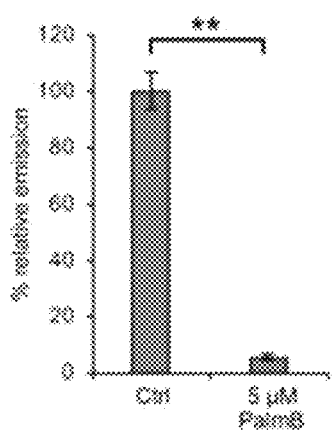
FIG. 36 is a graph showing the relative fluorescence response of depalmitoylation probe (DPP-5) in human cervical cancer (HeLa) cells. One micromolar (μM) DPP-5 was loaded into HeLa cells for 20 minutes with dimethylsulfoxide (DMSO, "Ctrl") and 5 μM inhibitor (palmostatin B (PalmB)) after a 30 minute treatment of the cells with either DMSO or 5 μM PalmB, and then analyzed by epifluorescence microscopy. **p<0.01. Error bars are standard errors of the mean (n=3). Statistical analysis was performed with a two-tailed Student's t-test with unequal variance.
Figure 37:
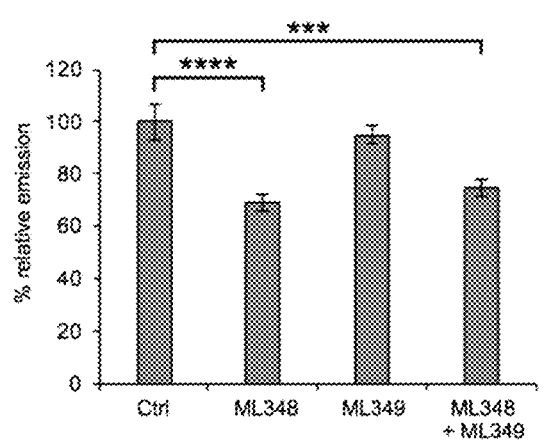
FIG. 37 is a graph showing the quantification of live cell imaging of depalmitoylation probe 5 (DPP-5) in human liver carcinoma (HepG2) cells with or without selective inhibitors of acyl protein thioesterase 1 (APT1) or acyl protein thioesterase 2 (APT2). HepG2 cells were treated for 30 minutes with 1 micromolar (μM) Hoechst 33342, and either dimethylsulfoxide (DMSO, "Ctrl") 10 μM of the APT1-specific inhibitor ML348, 10 μM of the APT2-specific inhibitor ML349, or 10 μM of each of ML348 and 349. Then the cells were washed, loaded with 1 μM DPP-5 for 20 minutes, and analyzed by epifluorescence microscopy. Error bars are standard errors of the mean (n=12). Statistical analysis was performed with a two-tailed Student's t-test with unequal variance. *P value<0.005, **P value<0.0008.

The activity of DPP-5 was also assayed in other cell lines. The PalmB imaging studies were repeated in human liver carcinoma (HepG2) cells and human cervical cancer (HeLa) cells. See FIGS. 35 and 36. Treatment of both cell lines with 1 μM probe for 20 minutes resulted in a robust intracellular fluorescent signal. Pretreatment of the cells with 5 μM PalmB blocked more than about 95% of the turn-on response, indicating that DPP-5 is measuring endogenous enzyme-mediated S-depalmitoylation. Additionally, 10 μM ML348, an APT1-specific inhibitor, decreased the intensity of the signal from DPP-5 by about 30% in HepG2 cells, while 10 μM ML349, an APT2-specific inhibitor, resulted in no change in signal. See FIG. 37. Further, treating the cells with both inhibitors affects DPP-5 to levels similar to that seen with the APT1 inhibitor alone. See FIG. 37. The differential reduction in the intensity of the DPP-5 signal with PalmB and ML348 reinforces the general reactivity of DPP-5 with all possible S-depalmitoylases and suggests that enzyme-targeted analogues of DPP-5 would be useful additions to the S-depalmitoylation toolbox. To compare the signal obtained with DPP-5 to DPP-1 and DPP-4, imaging experiments were conducted in HEK293T cells with identical concentrations of each probe and identical microscope settings. While DPP-5 treatment resulted in a robust fluorescent signal, DPP-1 and DPP-4 displayed relatively low levels of fluorescence, further confirming the advantage of adding a carboxylate group to the probe structure.

Example 18

Study of Palmitate Effects on Lipid Stress with DPP-5

Figure 38:
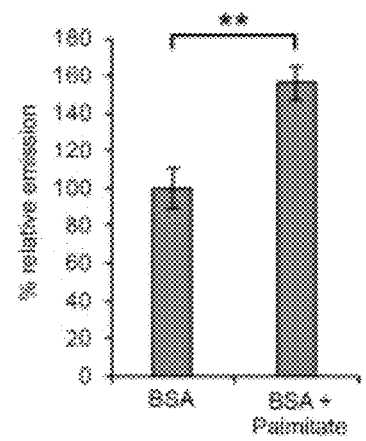
FIG. 38 is a graph showing the quantification of the relative fluorescence emission of depalmitoylation probe 5 (DPP-5) in human liver carcinoma (HepG2) cells treated with or without exogenous palmitate. HepG2 cells were treated with 1% bovine serum albumin (BSA) or with 1% BSA and 1 millimolar (mM) palmitate for 6 hours post-starvation, washed, loaded with 1 micromolar (μM) DPP-5 for 20 minutes, and imaged by epifluorescence microscopy. Error bars are standard errors of the mean (n=3). Statistical analysis was performed with a two-tailed Student's t-test with unequal variance. **P value<0.02.

Endogenous palmitate has been shown to cause ER stress and affect 3-cell viability. See Baldwin et al. (2012) Am J Physiol Endocrinol Metab 302, E1390-1398; and Cunha (2008) J Cell Sci 121, 2308-2318. Aberrant S-depalmitoylation has been demonstrated to be one of the mechanisms by which excess palmitate induces ER stress (see Baldwin et al. (2012) Am J Physiol Endocrinol Metab 302, E1390-1398), but the role of S-depalmitoylation dynamics in this process is largely unexplored. To test whether lipid stress through palmitate treatment causes a response from the S-depalmitoylyases, a study was performed to determine if DPP-5 could detect dynamic alterations in the S-depalmitoylases caused by exogenous palmitate treatment. Pretreatment of HepG2 cells with 1 mM palmitate for 6 hours post-starvation resulted in about a 50% increase in the intensity of the S-depalmitoylase signal as measured by DPP-5. See FIG. 38. Further, pretreatment of HepG2 cells with PalmB reduces the intensity of the DPP-5 signal, indicating that palmitate induces activation of S-depalmitoylase activity at the location at which DPP-5 is measuring the signal. See FIG. 39.

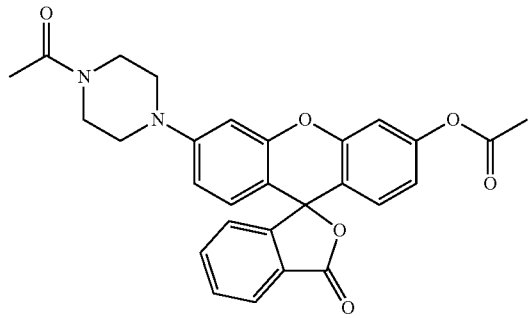

Scheme 8. Structure of Diacetyl rhodol.

To rule out the possibility that the changes in fluorescence signal are due to differential accumulation of DPP-5 in cells upon palmitate treatment, imaging was performed with a control probe, diacetyl rhodol (see Scheme 8, above) which maintains the pro-fluorophore core. Once it enters cells, the diacetyl rhodol probe is rapidly activated by intracellular esterases, thereby allowing the measurement of cell permeability and update of a related, non-APT-active compound. No measurable effect was seen on the fluorescence signal from HepG2 cells loaded with 1 μM diacetyl rhodol with 1 mM palmitate addition in the cells. See FIG. 40. Collectively, these data suggest that the S-depalmitoylases respond to local lipid homeostatic levels. These data further suggest that caution should be taken when adding exogenous lipids to metabolically label the proteome with lipids, as the lipid changes could cause alterations in the activities of the S-depalmitoylases, perturbing the system. Different responses to palmitate stress were also observed with RDP-type probes. Without being bound to any one theory, differential response could be due to differences in subcellular localization or APT preference.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A compound having a structure of Formula (Ia):

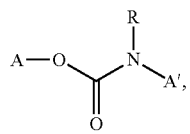

wherein:
  A is a residue of a compound A-OH, wherein A-OH is a fluorescent compound, a bio-luminescent compound, or a magnetic resonance imaging (MRI)-detectable compound, wherein said fluorescent compound is selected from the group consisting of a xanthene derivative, a rhodol derivative, and a fluorescein derivative;
  R is selected from the group consisting of H, alkyl, substituted alkyl, aralkyl, substituted aralkyl, aryl, and substituted aryl; and
  A' is selected from the group consisting of:

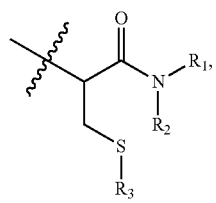 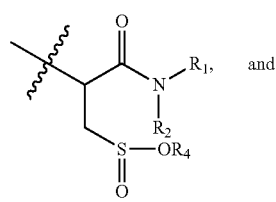 and

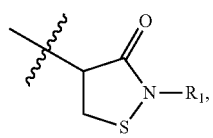

wherein:
  $R_1$ is selected from the group consisting of H, alkyl, substituted alkyl, aralkyl, substituted aralkyl, aryl, and substituted aryl; and
  $R_2$ is selected from the group consisting of H, alkyl, substituted alkyl, aralkyl, substituted aralkyl, aryl, and substituted aryl; or
  wherein $R_1$ and $R_2$ together with the nitrogen atom to which they are attached form an amino acid or peptidyl residue;
  $R_3$ is selected from the group consisting of alkyl, substituted alkyl, aralkyl, substituted aralkyl, aryl, substituted aryl, S(=O)$R_5$, —SH, —N(=O), S-glutathione, and —C(=O)$R_5$;
  $R_4$ is selected from H and $R_5$; and
  $R_5$ is selected from the group consisting of alkyl, substituted alkyl, aralkyl, and substituted aralkyl; or a pharmaceutically acceptable salt thereof.

2. The compound of claim 1, wherein A' is

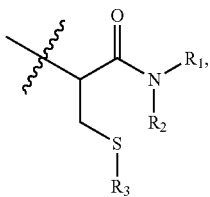

wherein R₁, R₂, and R₃ are as defined in claim 1.

3. The compound of claim 2, wherein the compound has a structure of Formula (IIa):

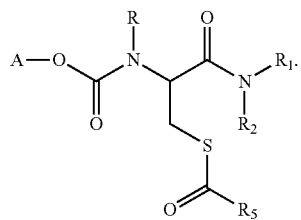

(IIa)

4. The compound of claim 3, wherein R₅ is —(CH₂)$_n$CH₃ wherein n is 1-18.

5. The compound of claim 1, wherein R₁ and R₂ together with the nitrogen atom to which they are attached form an amino acid or peptidyl residue and further wherein the amino acid or peptidyl residue comprises a positively charged amino acid residue.

6. The compound of claim 1, wherein the compound has a structure of Formula (Ia) wherein A is a residue of a compound A-OH, wherein A-OH is a or fluorescent compound and wherein the OH of the compound A-OH is a phenolic group.

7. A compound having a structure:

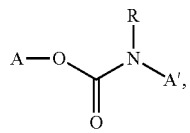

wherein:

A is a residue of a compound A-OH, wherein A-OH is a rhodol or a fluorescein derivative;

R is selected from the group consisting of H, alkyl, substituted alkyl, aralkyl, substituted aralkyl, aryl, and substituted aryl; and A' is selected from the group consisting of:

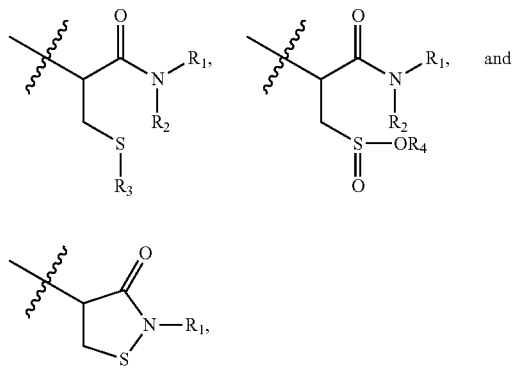

wherein:

R₁ is selected from the group consisting of H, alkyl, substituted alkyl, aralkyl, substituted aralkyl, aryl, and substituted aryl; and R₂ is selected from the group consisting of H, alkyl, substituted alkyl, aralkyl, substituted aralkyl, aryl, and substituted aryl; or wherein R₁ and R₂ together with the nitrogen atom to which they are attached form an amino acid or peptidyl residue;

R₃ is selected from the group consisting of alkyl, substituted alkyl, aralkyl, substituted aralkyl, aryl, substituted aryl, —S(=O)R₅, —SH, —N(=O), S-glutathione, and —C(=O)R₅;

R₄ is selected from H and R₅; and

R₅ is selected from the group consisting of alkyl, substituted alkyl, aralkyl, and substituted aralkyl; or a pharmaceutically acceptable salt thereof.

8. The compound of claim 1, wherein the compound is selected from the group consisting of:

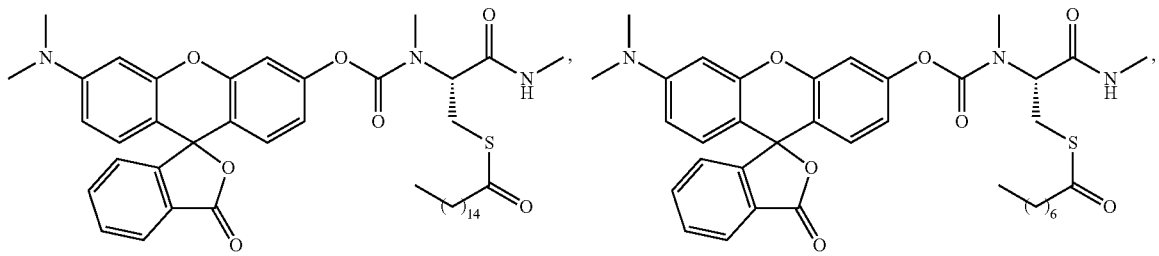

-continued

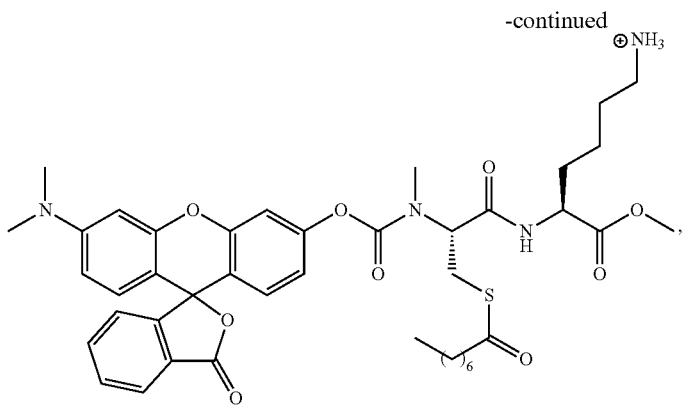

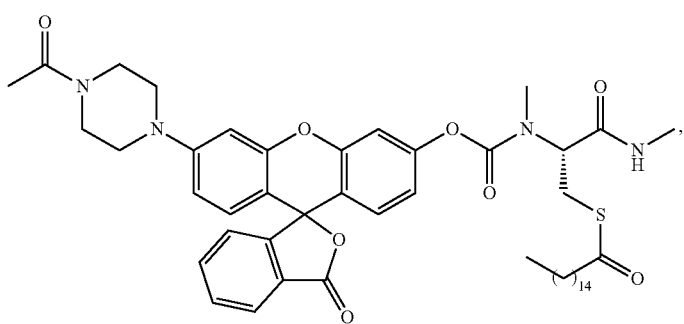

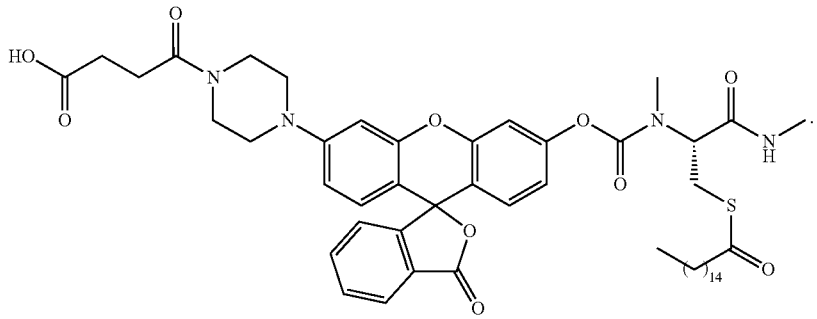

9. A method of detecting enzymatic activity in a sample, the method comprising:
contacting the sample with a compound of Formula (Ia):

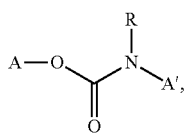
(Ia)

wherein:
A is a residue of a compound A-OH, wherein A-OH is a fluorescent compound selected from the group consisting of a xanthene derivative, a rhodol derivative, and a fluorescein derivative;
R is selected from the group consisting of H, alkyl, substituted alkyl, aralkyl, substituted aralkyl, aryl, and substituted aryl; and A' is selected from the group consisting of:

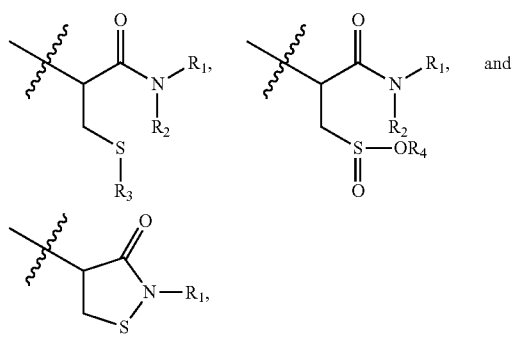

wherein:
$R_1$ is selected from the group consisting of H, alkyl, substituted alkyl, aralkyl, substituted aralkyl, aryl, and substituted aryl; and $R_2$ is selected from the group consisting of H, alkyl, substituted alkyl, aralkyl, substituted aralkyl, aryl, and substituted aryl; or wherein $R_1$ and $R_2$ together with the nitrogen atom to which they are attached form an amino acid or peptidyl residue;

$R_3$ is selected from the group consisting of alkyl, substituted alkyl, aralkyl, substituted aralkyl, aryl, substituted aryl, —S(=O)$R_5$, —SH, —N(=O), S-glutathione, and —C(=O)$R_5$;

$R_4$ is selected from H and $R_5$; and $R_5$ is selected from the group consisting of alkyl, substituted alkyl, aralkyl, and substituted aralkyl; or a pharmaceutically acceptable salt thereof; and detecting one or more fluorescence signals in the sample, wherein detecting the one or more fluorescence signals detects the presence and/or amount of enzymatic activity of an enzyme in the sample that catalyzes a reaction of a modified cysteine substrate.

10. The method of claim 9, wherein the enzyme is a thioesterase, an abhydrolyase domain containing 17A (ABHD17) protein, or a thioetherase.

11. The method of claim 9, wherein the sample is an in vitro sample.

12. The method of claim 9, wherein the sample comprises a live cell, tissue, or organ.

13. The method of claim 9, wherein the sample is a subject or a cell, tissue, or fluid obtained from a subject and wherein detecting enzymatic activity further detects a disease state associated with increased or decreased activity of an enzyme that catalyzes a reaction of a modified cysteine substrate.

* * * * *

```
                        SEQUENCE LISTING

<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: synthetic sequence

<400> SEQUENCE: 1
cggtggtgct aatagagata t                                          21

<210> SEQ ID NO 2
<211> LENGTH: 21
<212> TYPE: DNA
<213> ORGANISM: Artificial Sequence
<220> FEATURE:
<223> OTHER INFORMATION: synthetic sequence
```

```
<400> SEQUENCE: 2
ctatgccttc atggtttgat a                                        21

<210> SEQ ID NO 3
<211> LENGTH: 20
<212> TYPE: DNA
<213> ORGANISM: Artificial Sequence
<220> FEATURE:
<223> OTHER INFORMATION: synthetic sequence

<400> SEQUENCE: 3
caggaaatga tggatgtcaa                                          20

<210> SEQ ID NO 4
<211> LENGTH: 21
<212> TYPE: DNA
<213> ORGANISM: Artificial Sequence
<220> FEATURE:
<223> OTHER INFORMATION: synthetic sequence

<400> SEQUENCE: 4
ggctgctttc ttatccattt c                                        21

<210> SEQ ID NO 5
<211> LENGTH: 21
<212> TYPE: DNA
<213> ORGANISM: Artificial Sequence
<220> FEATURE:
<223> OTHER INFORMATION: synthetic sequence

<400> SEQUENCE: 5
gcagctgtga aggaatttct t                                        21
```